(12) United States Patent
Xu et al.

(10) Patent No.: US 8,236,802 B2
(45) Date of Patent: Aug. 7, 2012

(54) PARP INHIBITOR COMPOUNDS, COMPOSITIONS AND METHODS OF USE

(75) Inventors: Weizheng Xu, Ellicott City, MD (US); Greg Delahanty, Nottingham, MD (US); Ling Wei, Lutherville, MD (US); Jie Zhang, Ellicott City, MD (US)

(73) Assignee: Eisai Inc., Woodcliff Lake, NJ (US)

( * ) Notice: Subject to any disclaimer, the term of this patent is extended or adjusted under 35 U.S.C. 154(b) by 869 days.

(21) Appl. No.: 12/244,399

(22) Filed: Oct. 2, 2008

(65) Prior Publication Data

US 2009/0098084 A1    Apr. 16, 2009

Related U.S. Application Data

(60) Provisional application No. 60/977,115, filed on Oct. 3, 2007.

(51) Int. Cl.
*A01N 43/58* (2006.01)
*A61K 31/50* (2006.01)
*C07D 491/00* (2006.01)

(52) U.S. Cl. ........................ 514/250; 544/250
(58) Field of Classification Search ................ 544/251; 514/250
See application file for complete search history.

(56) References Cited

U.S. PATENT DOCUMENTS

| | | | |
|---|---|---|---|
| 6,291,425 B1 | 9/2001 | Li et al. | |
| 7,268,138 B2 | 9/2007 | Kalish et al. | |
| 7,456,178 B2 | 11/2008 | Kalish et al. | |
| 7,601,719 B2 | 10/2009 | Kalish et al. | |
| 7,750,008 B2 | 7/2010 | Kalish et al. | |
| 2006/0142231 A1 | 6/2006 | Ashworth et al. | |
| 2010/0256095 A1 | 10/2010 | Kalish et al. | |

FOREIGN PATENT DOCUMENTS

| WO | 99/59975 | 11/1999 |
|---|---|---|
| WO | 00/42040 | 7/2000 |
| WO | 2004/105700 | 9/2004 |
| WO | WO-2004/105700 A2 | 12/2004 |
| WO | WO-2006/078711 A2 | 7/2006 |
| WO | 2009/046205 | 9/2009 |

OTHER PUBLICATIONS

Pinedo et al, "Translational Research . . . ", The Oncologist 2000; 5(suppl1); 1-2. [www.The Oncologist.com].*
McMahon, G., VEGF Receptor Signaling in Tumor Angiogenisis. The Oncologist 2000;5(suppl 1):3-10. [www.TheOncologist.com].*
Vippagunta et al.*
Kinoshita et al., "Inhibitor-Induced Structural Change of the Active Site of Human Poly(ADP-ibose)polymerase," FEBS Letters, 2004, vol. 556, pp. 43-47, p. 43, Figure 1; p. 43, col. 2, para. 2; p. 44, col. 2, para. 3; p. 45, col. 1, para 1.2; col. 2, para 1; Figure 3.
Chalmers (TiPS vol. 17, pp. 166-172, Apr. 1996.
Gagne et al., "Current Opinion in Cell Biology," 2006, 18:145-151.
Combs et al., "Journal of Heterocyclic Chemistry," 1989, vol. 26, 1885-1886.
E.S. Newlands, et al., "Temozolomide: A Review of its Discovery, Chemical Properties, Pre-Clinical Development and Clinical Trials," Cancer Treatment Reviews (1997) 23, pp. 35-61.
Search Report for WO/2004/105700, 2004.
Search Report for WO/2009/046205, 2009.

* cited by examiner

*Primary Examiner* — Paul V. Ward
(74) *Attorney, Agent, or Firm* — Lathrop & Gage LLP; Brian C. Trinque

(57) ABSTRACT

The present invention relates to tetraaza phenalen-3-one compounds which inhibit poly (ADP-ribose) polymerase (PARP) and are useful in the chemosensitization of cancer therapeutics. The induction of peripheral neuropathy is a common side-effect of many of the conventional and newer chemotherapies. The present invention further provides means to reliably prevent or cure chemotherapy-induced neuropathy. The invention also relates to the use of the disclosed PARP inhibitor compounds in enhancing the efficacy of chemotherapeutic agents such as temozolomide. The invention also relates to the use of the disclosed PARP inhibitor compounds to radiosensitize tumor cells to ionizing radiation. The invention also relates to the use of the disclosed PARP inhibitor compounds for treatment of cancers with DNA repair defects.

12 Claims, 6 Drawing Sheets

PARP INHIBITOR COMPOUNDS, COMPOSITIONS AND METHODS OF USE

This application claims the benefit of U.S. Provisional Application No. 60/977,115, filed Oct. 3, 2007, the entire contents of which are hereby incorporated by reference.

FIELD OF THE INVENTION

The present invention relates to tetraaza phenalen-3-one compounds which inhibit poly (ADP-ribose) polymerase (PARP).

BACKGROUND

The present invention relates to inhibitors of the nuclear enzyme poly(adenosine 5'-diphospho-ribose) polymerase ["poly(ADP-ribose) polymerase" or "PARP", which is also referred to as ADPRT (NAD:protein (ADP-ribosyl transferase (polymerising)) and PARS (poly(ADP-ribose) synthetase) and provides compounds and compositions containing the disclosed compounds. Moreover, the present invention provides methods of using the disclosed PARP inhibitors to treat cancer.

There is considerable interest in the development of PARP inhibitors as chemosensitizers for use in cancer therapy and to limit cellular damage after ischemia or endotoxic stress. In particular, potentiation of temozolomide cytotoxicity observed in preclinical studies with potent PARP-1 inhibitors reflects inhibition of base excision repair and subsequent cytotoxicity due to incomplete processing of $N^7$-methylguanine and $N^3$-methyladenine. There is now a body of preclinical data demonstrating that the cytotoxicity of temozolomide is potentiated by coadministration of a PARP inhibitor either in vitro or in vivo. Plummer, et al., Clin. Cancer Res., 11(9), 3402 (2005).

Temozolomide, a DNA methylating agent, induces DNA damage, which is repaired by $O^6$-alkylguanine alkyltransferase (ATase) and poly(ADP-ribose) polymerase-1 (PARP-1)-dependent base excision repair. Temozolomide is an orally available monofunctional DNA alkylating agent used to treat gliomas and malignant melanoma. Temozolomide is rapidly absorbed and undergoes spontaneous breakdown to form the active monomethyl triazene, 5-(3-methyl-1-triazeno)imidazole-4-carboxamide. Monomethyl triazene forms several DNA methylation products, the predominate species being $N^7$-methylguanine (70%), $N^3$-methyladenine (9%), and $O^6$-methylguanine (5%). Unless repaired by $O^6$-alkylguanine alkyltransferase, $O^6$-methylguanine is cytotoxic due to mispairing with thymine during DNA replication. This mispairing is recognized on the daughter strand by mismatch repair proteins and the thymine excised. However, unless the original $O^6$-methylguanine nucleotide in the parent strand is repaired by ATase-mediated removal of the methyl adduct, thymine can be reinserted. Repetitive futile rounds of thymine excision and incorporation opposite an unrepaired $O^6$-methylguanine nucleotide causes a state of persistent strand breakage and the MutS branch of mismatch repair system signals G2-M cell cycle arrest and the initiation of apoptosis. The quantitatively more important $N^7$-methylguanine and $N^3$-methyladenine nucleotide alkylation products formed by temozoloride are rapidly repaired by base excision repair. Plummer, et al., Clin. Cancer Res., 11(9), 3402 (2005).

Chemosensitization by PARP inhibitors is not limited to temozolomide. Cytotoxic drugs, generally, or radiation can induce activation of PARP-1, and it has been demonstrated that inhibitors of PARP-1 can potentiate the DNA damaging and cytotoxic effects of chemotherapy and irradiation. Kock, et al., 45 J Med. Chem. 4961 (2002). PARP-1 mediated DNA repair in response to DNA damaging agents represents a mechanism for drug resistance in tumors, and inhibition of this enzyme has been shown to enhance the activity of ionizing radiation and several cytotoxic antitumor agents, including temozolomide and topotecan. Suto et al, in U.S. Pat. No. 5,177,075, disclose several isoquinolines used for enhancing the lethal effects of ionizing radiation or chemotherapeutic agents on tumor cells. Weltin et al., "Effect of 6(5H)-Phenanthridinone, an Inhibitor of Poly(ADP-ribose) Polymerase, on Cultured Tumor Cells", Oncol Res., 6:9, 399-403 (1994) disclose the inhibition of PARP activity, reduced proliferation of tumor cells, and a marked synergistic effect when tumor cells are co-treated with an alkylating drug. PARP-1 is thus a potentially important therapeutic target for enhancing DNA-damaging cancer therapies.

PARP inhibitors can also inhibit the growth of cells having defects in the homologous recombination (HR) pathway of double-stranded DNA repair. See Bryant et al., "Specific killing of BRCA2-deficient tumours with inhibitors of poly (ADP-ribose) polymerase," Nature 434, 913 (2005); Farmer et al., "Targeting the DNA repair defect in BRCA mutant cells as a therapeutic strategy," Nature 434, 917 (2005). This effect operates without the presence of chemosensitizers. Id. Known states associated with HR defects include BRCA-1 defects, BRCA-2 defects, and Fanconi anemia-associated cancers. McCabe et al., "Deficiency in the Repair of DNA Damage by Homologous Recombination and Sensitivity to Poly(ADP-Ribose) Polymerase Inhibition," Cancer Res. 66. 8109 (2006). Proteins identified as associated with a Fanconi anemia include FANCA, FANCB, FANCC, FANCD2, FANCE, FANCF, FANCG, FANCL, and FANCM. Id. For reviews, see Zaremba et al., "PARP Inhibitor Development for Systemic Cancer Targeting," Anti-Cancer Agents in Medicinal Chemistry 7, 515 (2007) and Lewis et al., "Clinical poly(ADP-ribose) polymerase inhibitors for the treatment of cancer," Curr Opin. Investigational Drugs 8, 1061 (2007).

Large numbers of known PARP inhibitors have been described in Banasik et al., "Specific Inhibitors of Poly(ADP-Ribose) Synthetase and Mono(ADP-Ribosyl)-Transferase", J. Biol. Chem., 267:3, 1569-75 (1992), and in Banasik et al., "Inhibitors and Activators of ADP-Ribosylation Reactions", Molec. Cell. Biochem., 138, 185-97 (1994). However, effective use of these PARP inhibitors, in the ways discussed above, has been limited by the concurrent production of unwanted side-effects. See Milam et al., "Inhibitors of Poly (Adenosine Diphosphate-Ribose) Synthesis; Effect on Other Metabolic Processes," Science, 223, 589-91 (1984).

In addition to the above, PARP inhibitors have been disclosed and described in the following international patent applications: WO 00/42040; WO 00/39070; WO 00/39104; WO 99/11623; WO 99/11628; WO 99/11622; WO 99/59975; WO 99/11644; WO 99/11945; WO 99/11649; and WO 99/59973. A comprehensive review of the state of the art has been published by Li and Zhang in IDrugs 2001, 4(7): 804-812 (PharmaPress Ltd ISSN 1369-7056).

The ability of PARP-inhibitors to potentiate the lethality of cytotoxic agents by chemosensitizing tumor cells to the cytotoxic effects of chemotherapeutic agents has been reported in, inter alia, US 2002/0028815; US 2003/0134843; US 2004/0067949; White A W, et al., 14 Bioorg. and Med. Chem. Letts. 2433 (2004); Canon Koch S S, et al., 45 J. Med. Chem. 4961 (2002); Skalitsky D J, et al., 46 J. Med. Chem. 210 (2003); Farmer H, et al., 434 Nature 917 (14 Apr. 2005); Plummer E R, et al., 11(9) Clin. Cancer Res. 3402 (2005); Tikhe J G, et al., 47 J. Med. Chem. 5467 (2004); Griffin R. J., et al., WO 98/33802; and Helleday T, et al, WO 2005/012305.

The induction of peripheral neuropathy is a common factor in limiting therapy with chemotherapeutic drugs. Quasthoff and Hartung, *J. Neurology*, 249, 9-17 (2002). Chemotherapy induced neuropathy is a side-effect encountered following the use of many of the conventional (e.g., Taxol, vincritine, cisplatin) and newer chemotherapies (e.g. velcade, epothilone). Depending on the substance used, a pure sensory and painful neuropathy (with cisplatin, oxaliplatin, carboplatin) or a mixed sensorimotor neuropathy with or without involvement of the autonomic nervous system (with vincristine, taxol, suramin) can ensue. Neurotoxicity depends on the total cumulative dose and the type of drug used. In individual cases neuropathy can evolve even after a single drug application. The recovery from symptoms is often incomplete and a long period of regeneration is required to restore function. Up to now, few drugs are available to reliably prevent or cure chemotherapy-induced neuropathy.

There continues to be a need for effective and potent PARP inhibitors which enhance the lethal effects of chemotherapeutic agents on tumor cells while producing minimal side-effects.

In addition, PARP inhibitors have been reported to be effective in radiosensitizing hypoxic tumor cells and effective in preventing tumor cells from recovering from potentially lethal damage of DNA after radiation therapy, presumably by their ability to prevent DNA repair. U.S. Pat. Nos. 5,032,617; 5,215,738; and 5,041,653.

Recent publications suggest that PARP inhibitors kill breast cancer cells that are deficient in breast cancer associated gene-1 and -2 (BRCA1/2). These studies suggest that PARP inhibitors may be effective for treating BRCA1/2-associated breast cancers. [Farmer et al., Nature 2005, 434, 917; DeSoto and Deng, Intl. J. Med. Sci. 2006, 3, 117; Bryant et al., Nature, 2005, 434, 913.]

There continues to be a need for effective and potent PARP inhibitors which enhance the lethal effects of ionizing radiation and/or chemotherapeutic agents on tumor cells, or inhibit the growth of cells having defects in the homologous recombination (HR) pathway of double-stranded DNA repair, while producing minimal side-effects.

SUMMARY OF INVENTION

The present invention provides compounds described herein, derivatives thereof and their uses to inhibit poly(ADP-ribose) polymerase ("PARP"), compositions containing these compounds and methods for making and using these PARP inhibitors to treat the effects of the conditions described herein.

The present invention also provides a tetraaza phenalen-3-one compound of Formula (I), or a pharmaceutically acceptable salt thereof:

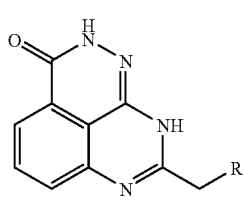

(I)

wherein R is (a) $NR^1R^2$, wherein $R^1$ is selected from the group consisting of hydrogen, $C_1$-$C_6$ straight or branched chain alkyl, $C_2$-$C_6$ straight or branched chain alkenyl, $C_3$-$C_8$ cycloalkyl, $C_1$-$C_6$ alkoxy, $C_2$-$C_6$ alkenyloxy, phenyl, phenoxy, benzyloxy, $NR^AR^B$ ($C_1$-$C_6$ straight or branched chain alkyl), $NR^AR^B$ ($C_2$-$C_6$ straight or branched chain alkenyl), ($C_1$-$C_6$ straight or branched chain alkyl)carbonyl, ($C_2$-$C_6$ straight or branched chain alkenyl)carbonyl, ($C_3$-$C_8$ cycloalkyl)carbonyl, ($C_1$-$C_6$ straight or branched chain alkyl)oxycarbonyl, ($C_2$-$C_6$ straight or branched chain alkenyl)oxycarbonyl, ($C_3$-$C_8$ cycloalkyl)oxycarbonyl, arylcarbonyl, sulfonyl, arylsulfonyl, aryl($C_1$-$C_6$ straight or branched chain alkyl), aryl($C_2$-$C_6$ straight or branched chain alkenyl), aryl($C_3$-$C_8$ cycloalkyl), ($C_1$-$C_6$ straight or branched chain alkyl)aryl, ($C_2$-$C_6$ straight or branched chain alkenyl)aryl, ($C_3$-$C_8$ cycloalkyl)aryl, aryl, heterocyclyl, heterocyclyl($C_1$-$C_6$ straight or branched chain alkyl), and heterocyclyl($C_2$-$C_6$ straight or branched chain alkenyl); wherein each heterocyclyl has between 1 and 7 heteroatoms independently selected from O, N, or S, and wherein each of $R^A$ and $R^B$ are independently selected from the group consisting of hydrogen, $C_1$-$C_6$ straight or branched chain alkyl, $C_2$-$C_6$ straight or branched chain alkenyl, and $C_3$-$C_8$ cycloalkyl;

and $R^2$ is selected from the group consisting of $C_1$-$C_6$ straight or branched chain alkyl, $C_2$-$C_6$ straight or branched chain alkenyl, $C_3$-$C_8$ cycloalkyl, $C_1$-$C_6$ alkoxy, $C_2$-$C_6$ alkenyloxy, phenyl, phenoxy, benzyloxy, $NR^XR^Y$ ($C_1$-$C_6$ straight or branched chain alkyl), $NR^XR^Y$ ($C_2$-$C_6$ straight or branched chain alkenyl), ($C_1$-$C_6$ straight or branched chain alkyl)carbonyl, ($C_2$-$C_6$ straight or branched chain alkenyl)carbonyl, ($C_3$-$C_8$ cycloalkyl)carbonyl, ($C_1$-$C_6$ straight or branched chain alkyl)oxycarbonyl, ($C_2$-$C_6$ straight or branched chain alkenyl)oxycarbonyl, ($C_3$-$C_8$ cycloalkyl)oxycarbonyl, arylcarbonyl, sulfonyl, arylsulfonyl, aryl($C_1$-$C_6$ straight or branched chain alkyl), aryl ($C_2$-$C_6$ straight or branched chain alkenyl), aryl($C_3$-$C_8$ cycloalkyl), ($C_1$-$C_6$ straight or branched chain alkyl)aryl, ($C_2$-$C_6$ straight or branched chain alkenyl)aryl, ($C_3$-$C_8$ cycloalkyl)aryl, aryl, heterocyclyl, heterocyclyl($C_1$-$C_6$ straight or branched chain alkyl), and heterocyclyl($C_2$-$C_6$ straight or branched chain alkenyl); wherein each heterocyclyl has between 1 and 7 heteroatoms independently selected from O, N, or S, and wherein each of $R^X$ and $R^Y$ are independently selected from the group consisting of hydrogen, $C_1$-$C_6$ straight or branched chain alkyl, $C_2$-$C_6$ straight or branched chain alkenyl, and $C_3$-$C_8$ cycloalkyl;

wherein $R^1$ and $R^2$ are independently substituted with between 0 and 4 substituents, each independently selected from halo, $C_1$-$C_6$ straight or branched chain alkyl, $C_2$-$C_6$ straight or branched chain alkenyl, $C_1$-$C_6$ alkoxy, trifluoromethyl, trifluoroethyl, and amino; and provided that $R^1$ and $R^2$ may not both be methyl, and $R^2$ may not be (phenyl)prop-1-yl when $R^1$ is hydrogen; or (b) aryloxy, substituted with between 0 and 4 substituents, each independently selected from the group consisting of halo, $C_1$-$C_6$ alkoxy, trifluoromethyl, trifluoroethyl, $C_1$-$C_6$ straight or branched chain alkyl, $C_2$-$C_6$ straight or branched chain alkenyl, $C_3$-$C_8$ cycloalkyl, $NR^CR^D$, $NR^CR^D$($C_1$-$C_6$ straight or branched chain alkyl), and $NR^CR^D$($C_2$-$C_6$ straight or branched chain alkenyl), wherein each of $R^C$ and $R^D$ is independently selected from the group consisting of hydrogen, $C_1$-$C_6$ straight or branched chain alkyl, $C_2$-$C_6$ straight or branched chain alkenyl, and $C_3$-$C_8$ cycloalkyl; and when more than one substituent is of the form $NR^CR^D$, each occurrence of $R^C$ and $R^D$ is independently selected from the group consisting of hydrogen, $C_1$-$C_6$ straight or branched chain alkyl, $C_2$-$C_6$ straight or branched chain alkenyl, and $C_3$-$C_8$ cycloalkyl; or (c) a heterocyclyl having between 1 and 7 heteroatoms independently selected from O, N, or S; and having between 0 and 4 substituents independently selected from the group consisting of halo, haloalkyl, hydroxyl, nitro, trifluoromethyl, trifluoroethyl, $C_1$-$C_6$ straight or branched chain alkyl, $C_2$-$C_6$ straight or branched chain alkenyl, $C_1$-$C_6$ alkoxy, $C_2$-$C_6$ alkenyloxy, phenyl, phenoxy, benzyloxy, amino, thiocarbonyl, cyano, imino, $NR^ER^F(C_1$-$C_6$ straight or branched chain alkyl), $NR^ER^F(C_2$-$C_6$ straight or branched chain alkenyl) sulflhydryl, thioalkyl, dioxa-spiroethyl, $(C_1$-$C_6$ straight or branched chain alkyl) carbonyl, $(C_2$-$C_6$ straight or branched chain alkenyl)carbonyl, $(C_1$-$C_6$ straight or branched chain alkyl)oxycarbonyl, $(C_2$-$C_6$ straight or branched chain alkenyl)oxycarbonyl, arylcarbonyl, sulfonyl, arylsulfonyl, aryl($C_1$-$C_6$ straight or branched chain alkyl), aryl($C_2$-$C_6$ straight or branched chain alkenyl), aryl($C_3$-$C_8$ cycloalkyl), $(C_1$-$C_6$ straight or branched chain alkyl)aryl, $(C_2$-$C_6$ straight or branched chain alkenyl)aryl, $(C_3$-$C_8$ cycloalkyl)aryl, aryl, heterocyclyl, heterocyclyl($C_1$-$C_6$ straight or branched chain alkyl), and heterocyclyl($C_2$-$C_6$ straight or branched chain alkenyl), wherein each heterocyclyl has between 1 and 7 heteroatoms independently selected from O, N, or S, wherein each of $R^E$ and $R^F$ is independently selected from the group consisting of hydrogen, $C_1$-$C_6$ straight or branched chain alkyl, $C_2$-$C_6$ straight or branched chain alkenyl, and $C_3$-$C_8$ cycloalkyl; and when more than one substituent is of the form $NR^ER^F$ each occurrence of $R^E$ and $R^F$ is independently selected from the group consisting of hydrogen, $C_1$-$C_6$ straight or branched chain alkyl, $C_2$-$C_6$ straight or branched chain alkenyl, and $C_3$-$C_8$ cycloalkyl; wherein each of said 0-4 substituents is independently substituted with between 0 and 4 further substituents, and each said further substituent is independently selected from halo, $C_1$-$C_6$ straight or branched chain alkyl, $C_2$-$C_6$ straight or branched chain alkenyl, $C_3$-$C_8$ cycloalkyl, $C_1$-$C_6$ alkoxy, trifluoromethyl, trifluoroethyl, and amino; provided that R has at least one substituent when R is an N-piperidinyl, N-pyrrolidinyl or an N-morpholinyl group.

In some embodiments each ring of each heterocyclyl of Formula (I) is independently 5-7 atoms in size.

Some embodiments include one, two or three nitrogen atoms in at least one ring of the heterocyclyl of Formula (I).

In some embodiments, the heterocyclyl of Formula (I) comprises 1-3 rings. In some embodiments, the heterocyclyl has 1-7 heteroatoms independently selected from O, N, and S. In some embodiments, the heterocyclyl comprises 1-2 rings. In some embodiments, the heterocyclyl comprises one ring. In some embodiments, the various occurrences of the heterocyclyl of Formula (I) each independently comprise 1-3 rings. In some embodiments, the various occurrences of the heterocyclyl of Formula (I) each independently comprise 1-2 rings. In some embodiments, the various occurrences of the heterocyclyl of Formula (I) each independently comprise one ring.

In some embodiments, the heterocyclyl of Formula (I) is selected from the group consisting of piperidinyl, piperazinyl, pyridazinyl, dihydropyridyl, tetrahydropyridyl, pyridinyl, pyrimidinyl, dihydropyrimidinyl, tetrahydrophyrimidinyl, hexahydropyrimidinyl, dihydropyrazinyl, tetrahydropyrazinyl, pyrrolidinyl, imidazolidinyl, pyrazolidinyl, pyrrolyl, dihydropyrolyl, imidazolyl, dihydroimidazoyl, pyrazolyl, dihydropyrazolyl, azepanyl, [1,2]diazepanyl, [1,3]diazepanyl, [1,4]diazepanyl, indolyl, dihydroindolyl, isoindolyl, dihydroisoindoly, dihydroquinolyl, tetrahydroquinolyl, dihydroisoquinolyl, and tetrahydroisoquinolyl; or subsets thereof.

The present invention also relates to a pharmaceutical composition comprising (i) a therapeutically amount of a compound of Formula (I) and (ii) a pharmaceutically acceptable carrier.

The present invention provides compounds which inhibit the in vitro and/or in vivo polymerase activity of poly(ADP-ribose) polymerase (PARP), and compositions containing the disclosed compounds.

The present invention provides methods to inhibit, limit and/or control the in vitro and/or in vivo polymerase activity of poly(ADP-ribose) polymerase (PARP) in solutions cells, tissues, organs or organ systems. In one embodiment, the present invention provides methods of limiting or inhibiting PARP activity in a mammal, such as a human, either locally or systemically.

In one embodiment, the invention provides a chemosensitization method for treating cancer comprising contacting the cancer cells with a cytotoxicity-potentiating tetraaza phenalen-3-one compound of Formula (I) or a pharmaceutically acceptable salt thereof and further contacting the tumor or cancer cells with an anticancer agent.

An embodiment of the present invention provides a chemosensitization method wherein a first dose of at least one compound of Formula (I) or a pharmaceutically acceptable salt thereof is administered singly or repeatedly to a patient in need thereof, and wherein subsequently a second dose of at least one chemotherapeutic agent is administered singly or repeatedly to said patient after a time period to provide an effective amount of chemosensitization.

An aspect of the present invention provides a pharmaceutical formulation comprising the compound of Formula (I) in a form selected from the group consisting of Non-limiting examples of such chemotherapeutic agents are recited below. pharmaceutically acceptable free bases, salts, hydrates, esters, solvates, stereoisomers, and mixtures thereof. According to a further aspect, the pharmaceutical formulation further comprises a pharmaceutically acceptable carrier and, optionally, a chemotherapeutic agent. The following embodiments are for illustrative purposes only and are not intended to limit in any way the scope of the present invention. In one embodiment, a pharmaceutical formulation of the invention comprises a compound of the invention in a pharmaceutically acceptable carrier. In another embodiment, a pharmaceutical formulation of the invention comprises a pharmaceutically acceptable salt of a compound of the invention in a pharmaceutically acceptable carrier. In another embodiment, a pharmaceutical formulation of the invention comprises a compound of the invention and one or more chemotherapeutic agents in a pharmaceutically acceptable carrier. In another embodiment, a pharmaceutical formulation of the invention comprises a pharmaceutically acceptable salt of a compound of the invention and one or more chemotherapeutic agents in a pharmaceutically acceptable carrier. Non-limiting examples of such chemotherapeutic agents are recited below.

According to additional aspects of the invention, the chemosensitizing compound and the chemotherapeutic agent are administered essentially simultaneously.

According to an aspect of the invention, the chemotherapeutic agent is selected from the group consisting of temozolomide, adriamycin, camptothecin, carboplatin, cisplatin, daunorubicin, docetaxel, doxorubicin, interferon-alpha, interferon-beta, interferon-gamma, interleukin 2, irinotecan, paclitaxel, a taxoid, dactinomycin, danorubicin, 4'-deoxydoxorubicin, bleomycin, pilcamycin, mitomycin, neomycin and gentamycin, etoposide, 4-OH cyclophosphamide, a platinum coordination complex, topotecan, therapeutically effective analogs and derivatives of the same, and mixtures thereof. According to a specific aspect, the chemotherapeutic agent is temozolomide.

In another embodiment, the present invention provides methods of treating the effect of cancer and/or to radiosensitize cancer cells to render the cancer cells more susceptible to radiation therapy and thereby to prevent the tumor cells from recovering from potentially lethal damage of DNA after radiation therapy, comprising administering to a subject an effective amount of a compound of Formula (I) or a pharmaceutically acceptable salt thereof. A method of this embodiment is directed to specifically and preferentially radiosensitizing cancer cells rendering the cancer cells more susceptible to radiation therapy than non-tumor cells.

The present invention also provides a method of treatment of cancer in a subject in need thereof comprising administering to the subject a therapeutically effective amount of a compound of Formula (I) or a pharmaceutically acceptable salt thereof, wherein the cancer cells have a defect in repair of double-stranded DNA scission. In one embodiment, the defect in repair of double-stranded DNA scission is a defect in homologous recombination. In one embodiment, the cancer cells have a phenotype selected from the group consisting of a BRCA-1 defect, a BRCA-2 defect, a BRCA-1 and BRCA-2 defect, and Fanconi anemia.

In another embodiment, the present invention provides methods of treating BRCA1/2-associated breast cancer comprising administering a compound of Formula (I) or a pharmaceutically acceptable salt thereof.

According to one embodiment of the invention, the compound for use in the chemosensitization method of the invention, the radiosensitization method of the invention, or the treatment of cancer wherein the cancer cells have a defect in repair of double-stranded DNA scission method of the invention, is a compound selected from Formula (I) or a pharmaceutically acceptable salt thereof. In another aspect, the compound is selected from the group consisting of

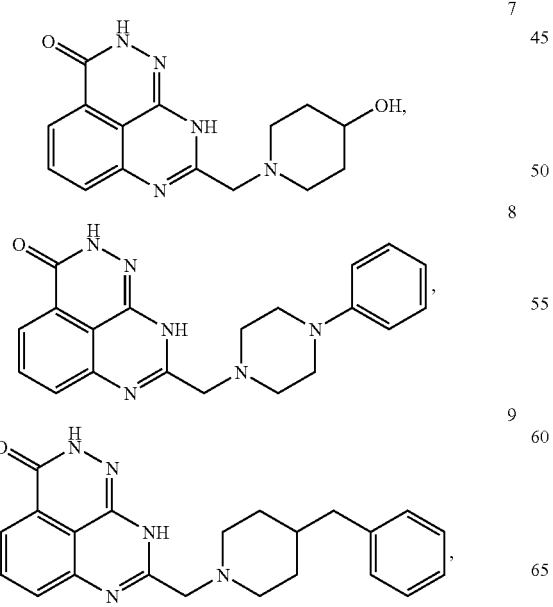

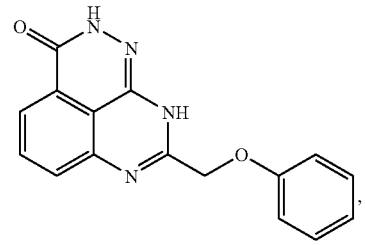

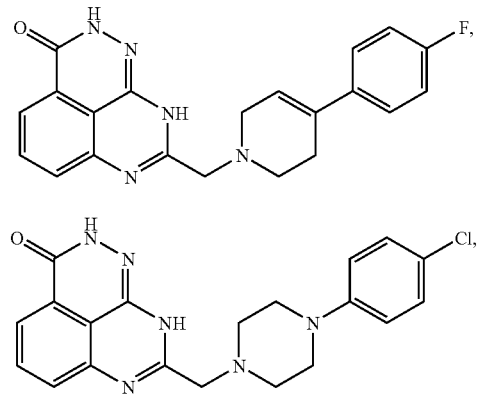

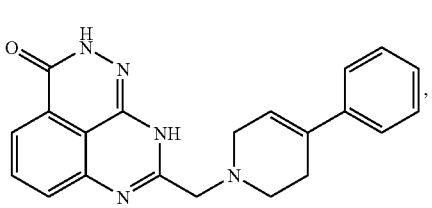

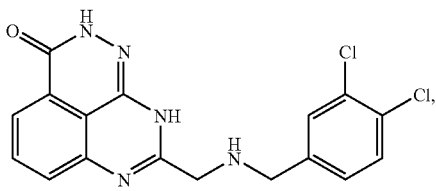

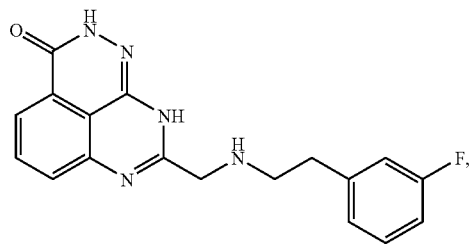

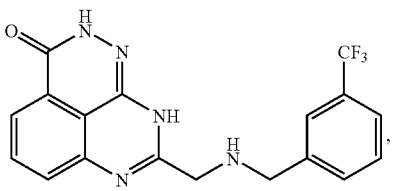

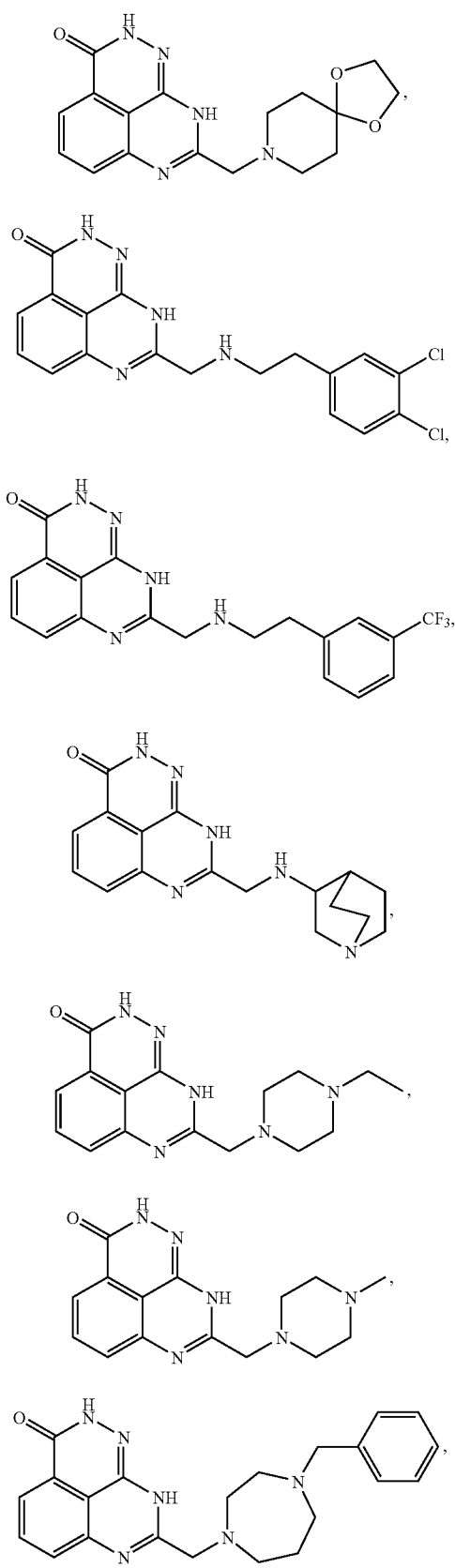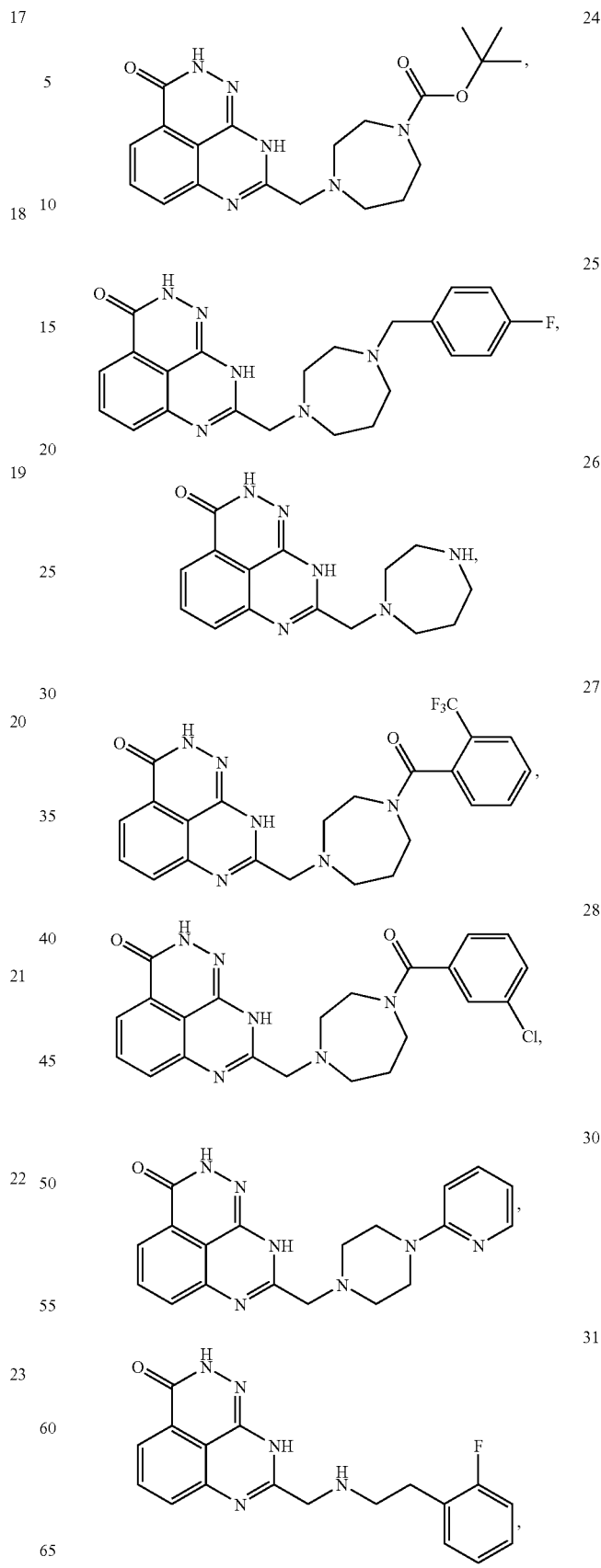

32
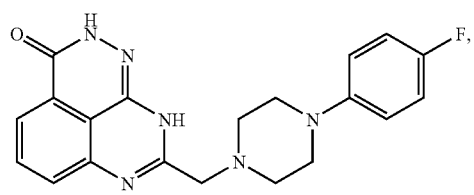
33
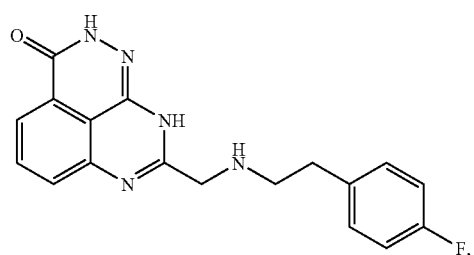
34
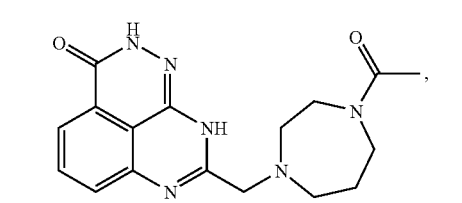
35
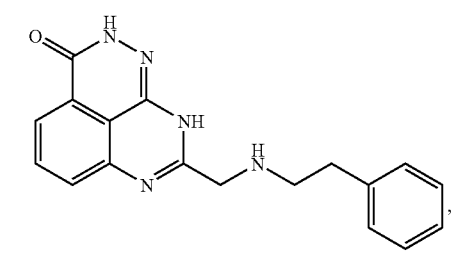
36
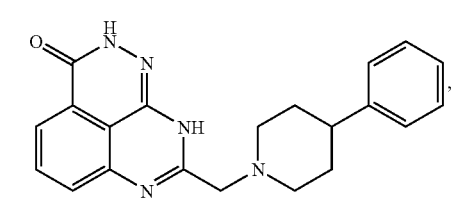
37
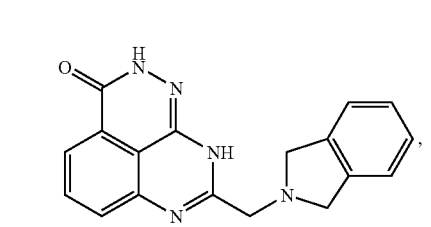
38
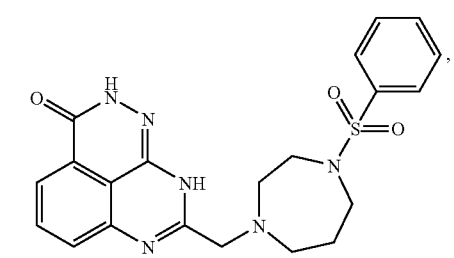
39
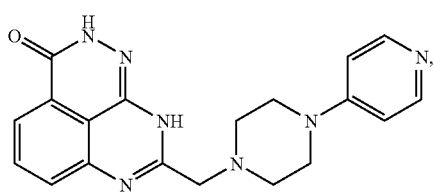
40
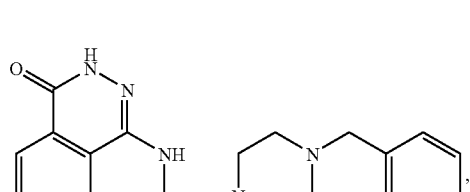
41
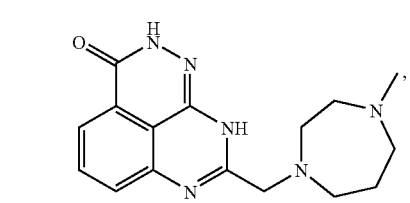
42
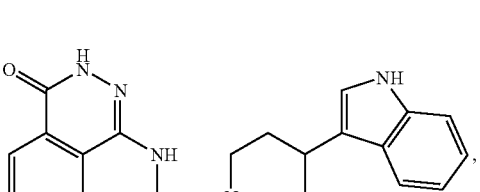
43
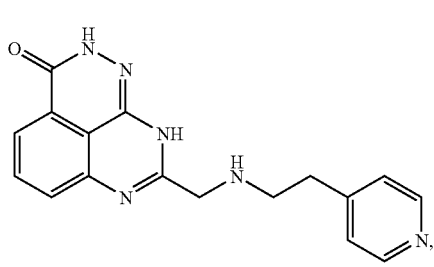
44
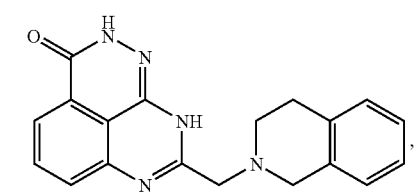
45
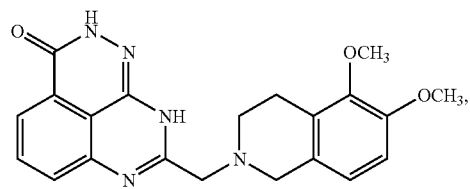

46
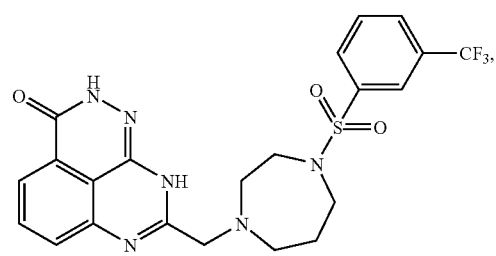
50
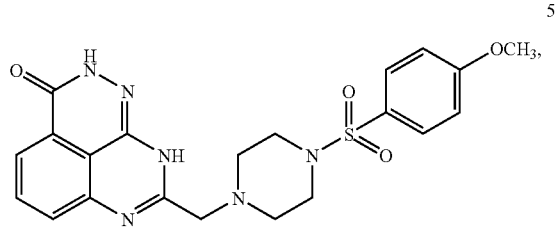
51
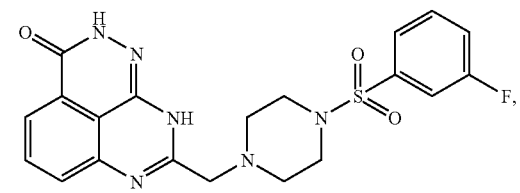
52
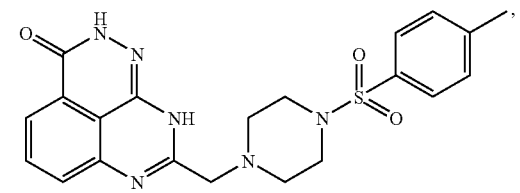
53
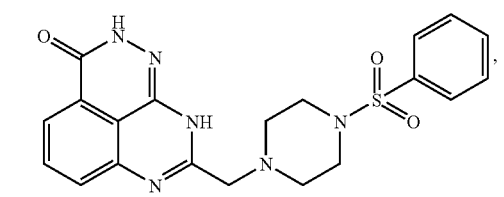
54
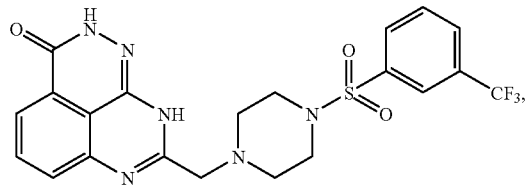
55
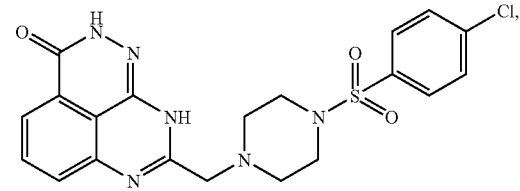
56
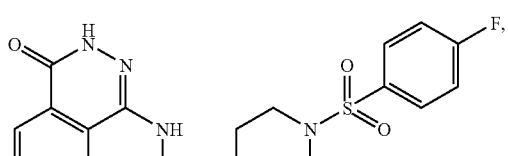
57
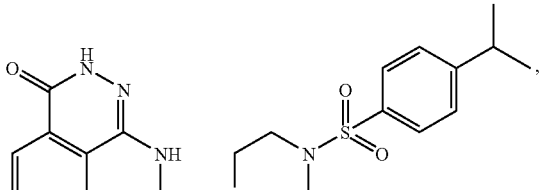
58
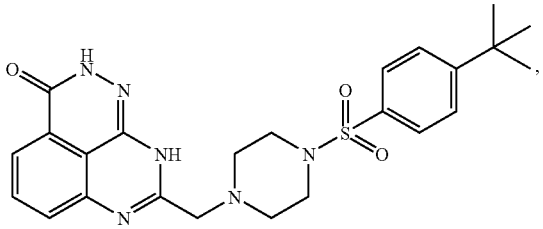
59
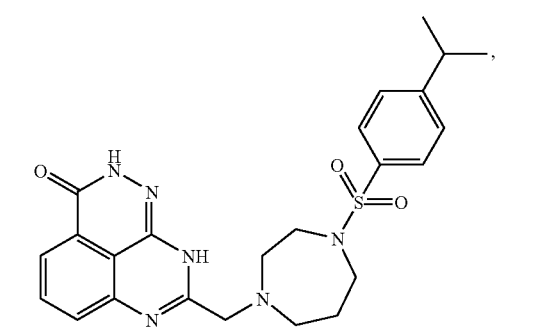
60
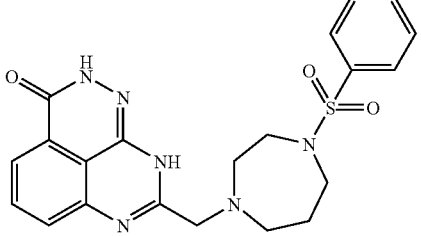
61
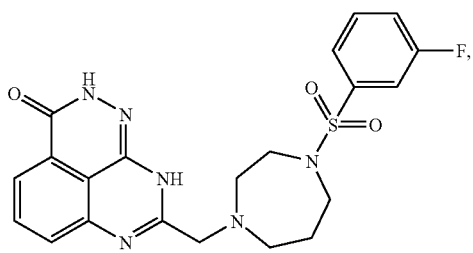

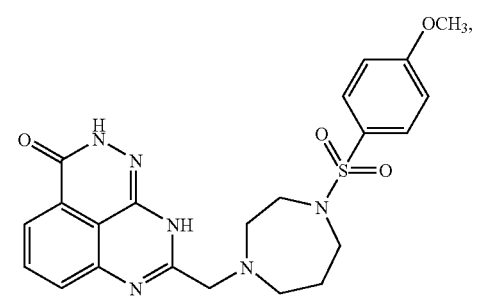

62

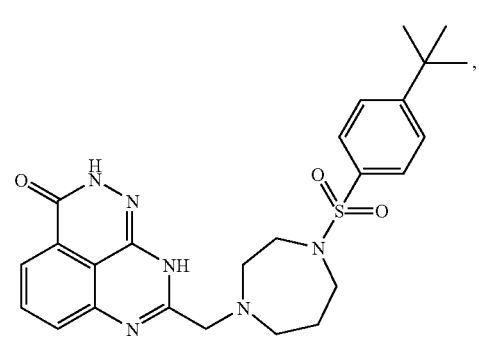

63

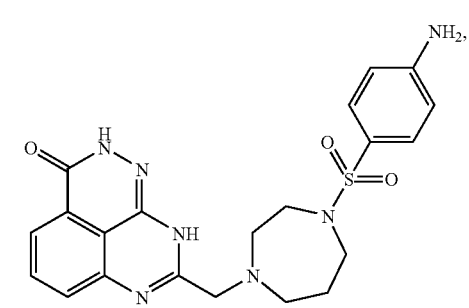

64

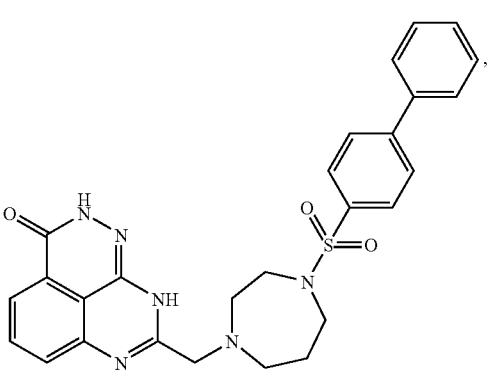

65

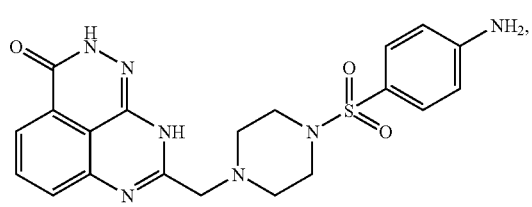

66

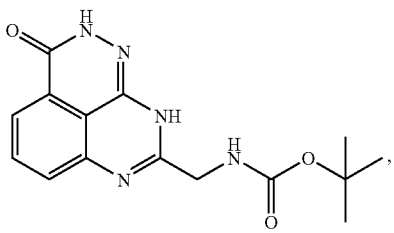

69

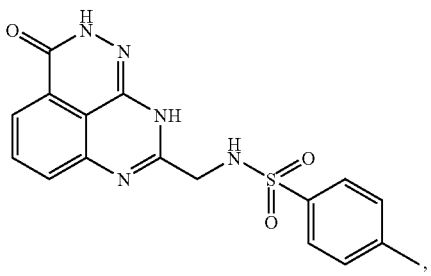

72

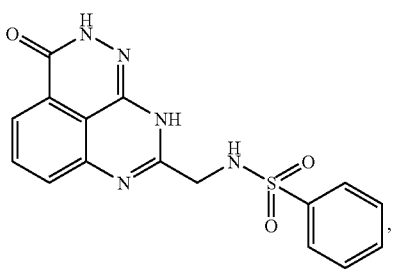

74

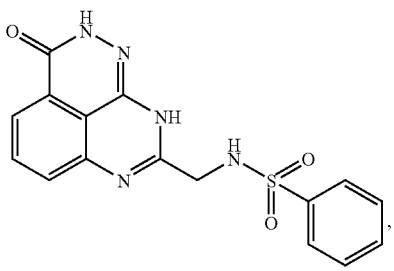

75

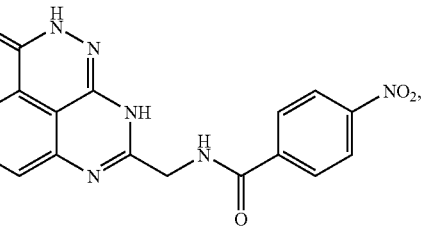

76 and pharmaceutically acceptable salts thereof.

The present invention also provides means to treat chemotherapy-induced peripheral neuropathy. According to an aspect of the invention, the compounds of the present invention are administered prior to, or together with, the administration of at least one chemotherapy agent to prevent the development of neuropathy symptoms or to mitigate the severity of such symptoms. According to a further aspect, the compounds of the present invention are administered after the administration of at least one chemotherapeutic agent to treat a patient for the symptoms of neuropathy or to mitigate the severity of such symptoms. In another aspect, the present invention provides a method to retard, delay, or arrest the growth of cancer cells in a mammal, comprising the administration of a chemotherapeutic agent, and further comprising the administration of a compound of Formula (I) or a pharmaceutically acceptable salt thereof in an amount sufficient to potentiate the anticancer activity of said chemotherapeutic agent.

Still other aspects and advantages of the present invention will become readily apparent by those skilled in the art from the following detailed description, wherein it is shown and described preferred embodiments of the invention, simply by way of illustration of the best mode contemplated of carrying out the invention. As will be realized the invention is capable of other and different embodiments, and its several details are capable of modifications in various obvious respects, without departing from the invention. Accordingly, the description is to be regarded as illustrative in nature and not as restrictive.

DETAILED DESCRIPTION OF THE INVENTION

Figure 1:
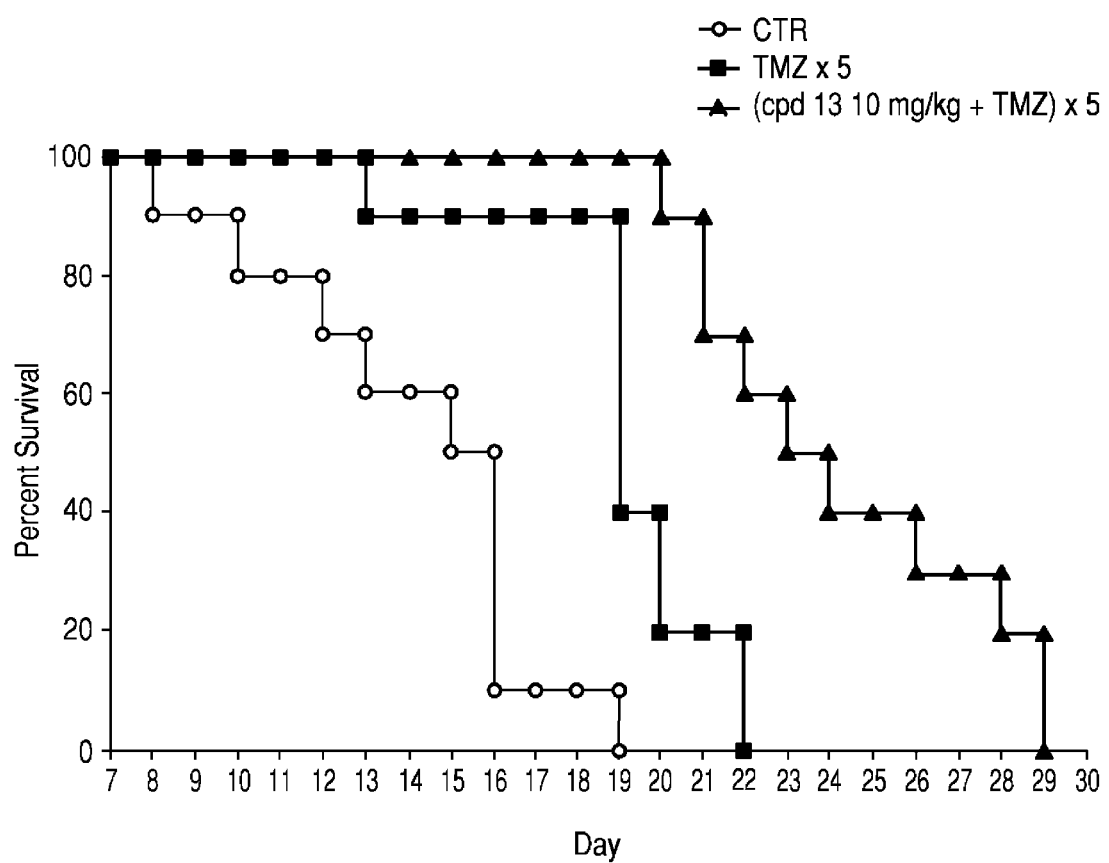
FIG. 1.—The oral administration of PARP-1 inhibitor Compound 13+TMZ demonstrating the enhance survival of mice bearing the B16 melanoma model.

The present invention provides compounds described herein, derivatives thereof and their uses to inhibit poly(ADP-ribose) polymerase ("PARP"), compositions containing these compounds and methods for making and using these compounds to treat, prevent and/or ameliorate the effects of cancers by potentiating the cytotoxic effects of ionizing radiation on tumor cells.

The present invention provides compounds described herein, derivatives thereof and their uses to inhibit poly(ADP-ribose) polymerase ("PARP"), compositions containing these compounds and methods for making and using these compounds to treat the effects of cancers by potentiating the cytotoxic effects of chemotherapeutic agents on tumor cells.

The present invention provides a chemosensitization method for treating tumor and/or cancer cells comprising contacting said cancer cells with a compound of Formula (I) and further contacting said cancer cells with an anticancer agent.

The present invention provides compounds described herein, derivatives thereof and their uses to inhibit poly(ADP-ribose) polymerase ("PARP"), compositions containing these compounds and methods for making and using these compounds to inhibit the growth of cells having defects in the homologous recombination (HR) pathway of double-stranded DNA repair.

The compounds and compositions of the present invention can be used in the presence or absence of radio- or chemo-sensitizers for the treatment of cancer. The compounds and compositions are preferably used in the absence of radio- or chemo-sensitizers where the cancer has a defect in the homologous recombination (HR) pathway of double-stranded DNA repair. Such defects are associated with, and have the phenotypes of, BRCA-1 defects, BRCA-2 defects, dual BRCA-1/BRCA-2 defects, and Fanconi anemia.

Fanconi anemia is a genetically heterogeneous disease and patients with Fanconi anemia have a greatly increased risk of cancer. Eleven proteins have been associated with Fanconi anemia. FANCA, FANCB, FANCC, FANCE, FANCF, FANCG, and FANCM form a nuclear core complex. The complex interacts with FANCL to incorporate ubiquinone of FANCD2. Modified FANCD2 is need for repair of DNA cross-links. FANCd2 accumulates at sites of DNA damage and associates with BRCA-1 and BRCA-2.

Exemplary cancers that can be associated with HR defects include breast cancer and ovarian cancer. Breast cancer for treatment by the methods of the invention can include all types of breast cancer and preferably includes invasive ductal carcinoma and invasive lobular carcinoma. Ovarian cancer for treatment by the methods of the invention include all types of ovarian cancer, preferably epithelial ovarian tumors, germ cell ovarian tumors, and sex cord stromal tumors.

The compounds of the present invention can be synthesized using the starting materials and methods disclosed in U.S. application Ser. No. 10/853,714, which is incorporated herein by reference in its entirety.

Typically, the compounds, such as those of Formula (I), used in the compositions of the invention will have an $IC_{50}$ for inhibiting poly(ADP-ribose) polymerase in vitro of about 20 μM or less, preferably less than about 10 μM, more preferably less than about 1 μM, or preferably less than about 0.1 μM, most preferably less than about 0.01 μM.

A convenient method to determine $IC_{50}$ of a PARP inhibitor compound is a PARP assay using purified recombinant human PARP from Trevigan (Gaithersburg, Md.), as follows: The PARP enzyme assay is set up on ice in a volume of 100 microliters consisting of 100 mM Tris-HCl (pH 8.0), 1 mM $MgCl_2$, 28 mM KCl, 28 mM NaCl, 3.0 μg/ml of DNase I-activated herring sperm DNA (Sigma, Mo.), 30 micromolar [$^3$H]nicotinamide adenine dinucleotide (62.5 mCi/mmole), 15 micrograms/ml PARP enzyme, and various concentrations of the compounds to be tested. The reaction is initiated by adding enzyme and incubating the mixture at 25° C. After 2 minutes of incubation, the reaction is terminated by adding 500 microliters of ice cold 30% (w/v) trichloroacetic acid. The precipitate formed is transferred onto a glass fiber filter (Packard Unifilter-GF/C) and washed three times with 70% ethanol. After the filter is dried, the radioactivity is determined by scintillation counting. The compounds of this invention were found to have potent enzymatic activity in the range of a few nanomolar to 20 micromolar in $IC_{50}$ in this inhibition assay.

As used herein, "alkyl" means a branched or unbranched saturated hydrocarbon chain comprising a designated number of carbon atoms. For example, $C_1$-$C_6$ straight or branched alkyl hydrocarbon chain contains 1 to 6 carbon atoms, and includes but is not limited to substituents such as methyl, ethyl, propyl, iso-propyl, butyl, iso-butyl, tert-butyl, n-pentyl, n-hexyl, and the like, unless otherwise indicated. In some embodiments, the alkyl chain is a $C_1$ to $C_6$ branched or unbranched carbon chain. In some embodiments, the alkyl chain is a $C_2$ to $C_5$ branched or unbranched carbon chain. In some embodiments, the alkyl chain is a $C_1$ to $C_4$ branched or unbranched carbon chain. In some embodiments, the alkyl chain is a $C_2$ to $C_4$ branched or unbranched carbon chain. In some embodiments, the alkyl chain is a $C_3$ to $C_5$ branched or unbranched carbon chain. In some embodiments, the alkyl chain is a $C_1$ to $C_2$ branched or unbranched carbon chain. In some embodiments, the alkyl chain is a $C_2$ to $C_3$ branched or unbranched carbon chain.

"Alkenyl" means a branched or unbranched unsaturated hydrocarbon chain comprising a designated number of carbon atoms. For example, $C_2$-$C_6$ straight or branched alkenyl hydrocarbon chain contains 2 to 6 carbon atoms having at least one double bond, and includes but is not limited to substituents such as ethenyl, propenyl, isopropenyl, butenyl, iso-butenyl, tert-butenyl, n-pentenyl, n-hexenyl, and the like, unless otherwise indicated. In some embodiments, the alkenyl chain is a $C_2$ to $C_6$ branched or unbranched carbon chain. In some embodiments, the alkenyl chain is a $C_2$ to $C_5$ branched or unbranched carbon chain. In some embodiments, the alkenyl chain is a $C_2$ to $C_4$ branched or unbranched carbon chain. In some embodiments, the alkenyl chain is a $C_3$ to $C_5$ branched or unbranched carbon chain.

"Alkoxy", means the group —OZ wherein Z is alkyl as herein defined. Z can also be a branched or unbranched saturated hydrocarbon chain containing 1 to 6 carbon atoms.

"Cyclo", used herein as a prefix, refers to a structure characterized by a closed ring.

"Halo" means at least one fluoro, chloro, bromo, or iodo moiety, unless otherwise indicated.

Each of "$NR^AR^B$", "$NR^XR^Y$", "$NR^CR^D$", and "$NR^ER^F$" as described herein independently encompass amino ($NH_2$) as well as substituted amino. For example, $NR^AR^B$ may be —$NH(CH_3)$, —$NH(cyclohexyl)$, and —$N(CH_2CH_3)(CH_3)$. When more than one substituent is of the form "$NR^AR^B$", "$NR^XR^Y$", "$NR^CR^D$", or "$NR^ER^F$", each occurrence of $R^A$, $R^B$, $R^C$, $R^D$, $R^X$, or $R^Y$ is independently selected from the group consisting of hydrogen, $C_1$-$C_6$ straight or branched chain alkyl, $C_2$-$C_6$ straight or branched chain alkenyl, and $C_3$-$C_8$ cycloalkyl. Such examples are for illustrative purposes only and are not intended to be limiting in any way.

"Arylcarbonyl" refers to a carbonyl radical substituted with aryl as described herein. Non-limiting examples include phenylcarbonyl and naphthylcarbonyl.

"Alkylcarbonyl" refers to a carbonyl radical substituted with alkyl as described herein. Non-limiting examples include acyl and propylcarbonyl.

"Alkoxycarbonyl" refers to a carbonyl radical substituted with alkoxy as described herein. Non-limiting examples include methoxycarbonyl and tert-butyloxycarbonyl.

"Ar" or "aryl" refer to an aromatic carbocyclic moiety having one or more closed rings. Examples include, without limitation, phenyl, naphthyl, anthracenyl, phenanthracenyl, biphenyl, and pyrenyl.

"Heterocyclyl" refers to a cyclic moiety having one or more closed rings, with one or more heteroatoms (for example, oxygen, nitrogen or sulfur) in at least one of the rings, and wherein the ring or rings may independently be aromatic, nonaromatic, fused, and/or bridged, Examples include without limation piperidinyl, piperazinyl, pyridazinyl, dihydropyridyl, tetrahydropyridyl, pyridinyl, pyrimidinyl, dihydropyrimidinyl, tetrahydrophyrimidinyl, hexahydropyrimidinyl, dihydropyrazinyl, tetrahydropyrazinyl, pyrrolidinyl, imidazolidinyl, pyrazolidinyl, pyrrolyl, dihydropyrolyl, imidazolyl, dihydroimidazoyl, pyrazolyl, dihydropyrazolyl, azepanyl, [1,2]diazepanyl, [1,3]diazepanyl, [1,4]diazepanyl, indolyl, dihydroindolyl, isoindolyl, dihydroisoindoly, dihydroquinolyl, tetrahydroquinolyl, dihydroisoquinolyl, and tetrahydroisoquinolyl.

"Arylalkyl" refers to an alkyl radical substituted with aryl. Non-limiting examples include benzyl, phenylethyl, and phenylpropyl.

"Alkylaryl" refers to an aryl radical substituted with alkyl. Non-limiting examples include tolyl and dimethylphenyl.

"Cycloalkyl" refers to a hydrocarbon cyclic moiety that is nonaromatic. Examples include without limitation cyclopropane, cyclobutane, cyclopentane, cyclohexane, cycloheptane, cyclooctane, cyclopentene, cyclohexene, cycloheptene, and cyclooctene.

The term "nervous insult" refers to any damage to nervous tissue and any disability or death resulting therefrom The cause of nervous insult may be metabolic, toxic, neurotoxic, iatrogenic, thermal or chemical, and includes without limitation, ischemia, hypoxia, cerebrovascular accident, trauma, surgery, pressure, mass effect, hemorrhage, radiation, vasospasm, neurodegenerative disease, infection, Parkinson's disease, amyotrophic lateral sclerosis (ALS), myelination/demyelination process, epilepsy, cognitive disorder, glutamate abnormality and secondary effects thereof.

The term "neuroprotective" refers to the effect of reducing, arresting or ameliorating nervous insult, and protecting, resuscitating, or reviving nervous tissue that has suffered nervous insult.

The term "preventing neurodegeneration" includes the ability to prevent a neurodegenerative disease or preventing further neurodegeneration in patients who are already suffering from or have symptoms of a neurodegenerative disease.

The term "treating" refers to:

(i) preventing a disease, disorder or condition from occurring in an animal that may be predisposed to the disease, disorder and/or condition, but has not yet been diagnosed as having it; and/or (ii) inhibiting the disease, disorder or condition, i.e., arresting its development; and/or (iii) relieving the disease, disorder or condition, i.e., causing regression of the disease, disorder and/or condition.

The term "chemosensitizer", as used herein, is defined as a molecule, such as a low molecular weight molecule, administered to animals in therapeutically effective amounts to potentiate the antitumoral activity of chemotherapeutic agents. Such chemosensitizers are useful, for example, to increase the tumor growth-retarding or -arresting effect of a given dose of a chemotherapeutic agent, or to improve the side-effect profile of a chemotherapeutic agent by allowing for reductions in its dose while maintaining its antitumoral efficacy.

The term "radiosensitizer", as used herein is defined as a molecule, such as a low molecular weight molecule, administered to animals in therapeutically effective amounts to increase the sensitivity of the cells to be radiosensitized to electromagnetic radiation and/or to promote the treatment of diseases which are treatable with electromagnetic radiation. Diseases which are treatable with electromagnetic radiation include neoplastic diseases, benign and malignant tumors, and cancerous cells. Electromagnetic radiation treatment of other diseases not listed herein is also contemplated.

"Effective amount" refers to the amount required to produce the desired effect.

"Substituted" means that at least one hydrogen on a designated group is replaced with another radical, provided that the designated group's normal valence is not exceeded. With respect to any group containing one or more substituents, such groups are not intended to introduce any substitution that is sterically impractical, synthetically non-feasible and/or inherently unstable. In some embodiments of the invention as described herein, a substituent may substitute a radical, which said radical is itself a substituent. For example, in the compound shown below for illustrative purposes only, the piperazinyl ring is a heterocyclyl, which may be substituted with 0-4 substituents as described herein. In the example compound, the piperazinyl ring is substituted with arylsulfonyl wherein aryl is phenyl, and wherein the arylsulfonyl may be further substituted 0-4 times as described herein. In the example compound, the phenylsulfonyl moiety is further substituted with tert-butyl. Such example is given for illustrative purposes only and is not intended to be limiting in any way.

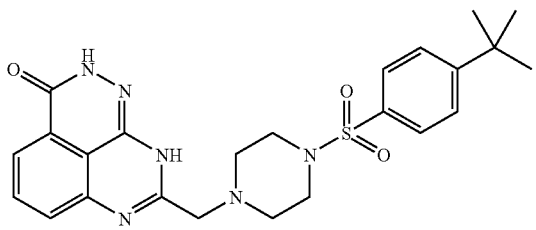

"Subject" refers to a cell or tissue, in vitro or in vivo, an animal or a human. An animal or human subject may also be referred to as a "patient."

"Animal" refers to a living organism having sensation and the power of voluntary movement, and which requires for its existence oxygen and organic food. Examples include, without limitation, members of the human, mammalian and primate species.

Broadly, the compounds and compositions of the present invention can be used to treat or prevent cell damage or death due to necrosis or apoptosis, cerebral ischemia and reperfusion injury or neurodegenerative diseases in an animal, such as a human. The compounds and compositions of the present invention can be used to extend the lifespan and proliferative capacity of cells and thus can be used to treat or prevent diseases associated therewith; they alter gene expression of senescent cells; and they radiosensitize hypoxic tumor cells. Preferably, the compounds and compositions of the invention can be used to treat or prevent tissue damage resulting from cell damage or death due to necrosis or apoptosis, and/or effect neuronal activity, either mediated or not mediated by NMDA toxicity. The compounds of the present invention are not limited to being useful in treating glutamate mediated neurotoxicity and/or NO-mediated biological pathways. Further, the compounds of the invention can be used to treat or prevent other tissue damage related to PARP activation, as described herein.

The present invention provides compounds which inhibit the in vitro and/or in vivo polymerase activity of poly(ADP-ribose) polymerase (PARP), and compositions containing the disclosed compounds.

The present invention provides methods to inhibit, limit and/or control the in vitro and/or in vivo polymerase activity of poly(ADP-ribose) polymerase (PARP) in any of solutions, cells, tissues, organs or organ systems. In one embodiment, the present invention provides methods of limiting or inhibiting PARP activity in a mammal, such as a human, either locally or systemically.

The compounds of the invention act as PARP inhibitors to treat or prevent cancers by chemopotentiating the cytotoxic effects of the chemotherapeutic agents. The compounds of the invention act as PARP inhibitors to treat or prevent cancers by sensitizing cells to the cytotoxic effects of radiation. The compounds of the invention act as PARP inhibitors to treat or prevent BRCA1/2-associated breast cancer.

The compounds of the present invention may possess one or more asymmetric center(s) and thus can be produced as mixtures (racemic and non-racemic) of stereoisomers, or as individual enantiomers or diastereomers. The individual stereoisomers may be obtained by using an optically active staring material, by resolving a racemic or non-racemic mixture of an intermediate at some appropriate stage of the synthesis, or by resolution of the compound of Formula (I). It is understood that the individual stereoisomers as well as mixtures (racemic and non-racemic) of stereoisomers are encompassed by the scope of the present invention.

The compounds of the invention are useful in a free base form, in the form of pharmaceutically acceptable salts, pharmaceutically acceptable hydrates, pharmaceutically acceptable esters, pharmaceutically acceptable solvates, pharmaceutically acceptable prodrugs, pharmaceutically acceptable metabolites, and in the form of pharmaceutically acceptable stereoisomers. These forms are all within the scope of the disclosure.

"Pharmaceutically acceptable salt", "hydrate", "ester" or "solvate" refers to a salt, hydrate, ester, or solvate of the inventive compounds which possesses the desired pharmacological activity and which is neither biologically nor otherwise undesirable. Organic acids can be used to produce salts, hydrates, esters, or solvates such as acetate, adipate, alginate, aspartate, benzoate, benzenesulfonate, p-toluenesulfonate, bisulfate, sulfamate, sulfate, naphthylate, butyrate, citrate, camphorate, camphorsulfonate, cyclopentane-propionate, digluconate, dodecylsulfate, ethanesulfonate, fumarate, glucoheptanoate, glycerophosphate, hemisulfate heptanoate, hexanoate, 2-hydroxyethanesulfonate, lactate, maleate, methanesulfonate, 2-naphthalenesulfonate, nicotinate, oxalate, tosylate and undecanoate. Inorganic acids can be used to produce salts, hydrates, esters, or solvates such as hydrochloride, hydrobromide, hydroiodide, and thiocyanate.

Examples of suitable base salts, hydrates, esters, or solvates include hydroxides, carbonates, and bicarbonates of ammonia, alkali metal salts such as sodium, lithium and potassium salts, alkaline earth metal salts such as calcium and magnesium salts, aluminum salts, and zinc salts.

Salts, hydrates, esters, or solvates may also be formed with organic bases. Organic bases suitable for the formation of pharmaceutically acceptable base addition salts, hydrates, esters, or solvates of the compounds of the present invention include those that are non-toxic and strong enough to form such salts, hydrates, esters, or solvates. For purposes of illustration, the class of such organic bases may include mono-, di-, and trialkylamines, such as methylamine, dimethylamine, triethylamine and dicyclohexylamine; mono-, di- or trihydroxyalkylamines, such as mono-, di-, and triethanolamine; amino acids, such as arginine and lysine; guanidine; N-methyl-glucosamine; N-methyl-glucamine; L-glutamine; N-methyl-piperazine; morpholine; ethylenediamine; N-benzyl-phenethylamine; (trihydroxy-methyl)aminoethane; and the like. See, for example, "Pharmaceutical Salts," J. Pharm. Sci., 66:1, 1-19 (1977). Accordingly, basic nitrogen-containing groups can be quaternized with agents including: lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

The acid addition salts, hydrates, esters, or solvates of the basic compounds may be prepared either by dissolving the free base of a compound of the present invention in an aqueous or an aqueous alcohol solution or other suitable solvent containing the appropriate acid or base, and isolating the salt by evaporating the solution. Alternatively, the free base of a compound of the present invention can be reacted with an acid, as well as reacting a compound of the present invention having an acid group thereon with a base, such that the reactions are in an organic solvent, in which case the salt separates directly or can be obtained by concentrating the solution.

"Pharmaceutically acceptable prodrug" refers to a derivative of the inventive compounds which undergoes biotransformation prior to exhibiting its pharmacological effect(s). The prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compounds using methods known in the art, such as those described by Burgers Medicinal Chemistry and Drug Chemistry, Fifth Ed, Vol. 1, pp. 172-178, 949-982 (1995). For example, the inventive compounds can be transformed into prodrugs by converting one or more of the hydroxy or carboxy groups into esters.

"Pharmaceutically acceptable metabolite" refers to drugs that have undergone a metabolic transformation. After entry into the body, most drugs are substrates for chemical reactions that may change their physical properties and biologic effects. These metabolic conversions, which usually affect the polarity of the compound, alter the way in which drugs are distributed in and excreted from the body. However, in some cases, metabolism of a drug is required for therapeutic effect. For example, anticancer drugs of the antimetabolite class must be converted to their active forms after they have been transported into a cancer cell. Since most drugs undergo metabolic transformation of some kind, the biochemical reactions that play a role in drug metabolism may be numerous and diverse. The main site of drug metabolism is the liver, although other tissues may also participate.

Further still, the methods of the invention can be used to treat cancer and to chemosensitize and radiosensitize cancer and/or tumor cells. The term "cancer," as used herein, is defined broadly. The compounds of the present invention can potentiate the effects of "anti-cancer agents," which term also encompasses "anti-tumor cell growth agents," "chemotherapeutic agents," "cytostatic agents," "cytotoxic agents," and "anti-neoplastic agents". The term "BRCA1/2-associated breast cancer" encompasses breast cancer in which the breast cancer cells are deficient in the breast cancer tumor suppressor genes BRCA1 and/or BRCA2.

For example, the methods of the invention are useful for treating cancers such as ACTH-producing tumors, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head and neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovarian cancer, ovary (germ cell) cancer, prostate cancer, pancreatic cancer, penile cancer, retinoblastoma, skin cancer, soft-tissue sarcoma, squamous cell carcinomas, stomach cancer, testicular cancer, thyroid cancer, trophoblastic neoplasms, uterine cancer, vaginal cancer, cancer of the vulva and Wilm's tumor.

In some non-limiting embodiments, the cancer and/or tumor cells are selected from the group consisting of brain cancer, melanoma, head and neck cancer, non small cell lung cancer, testicular cancer, ovarian cancer, colon cancer and rectal cancer.

The present invention also relates to a pharmaceutical composition comprising (i) a therapeutically effective amount of a compound of a compound of Formula (I) and (ii) a pharmaceutically acceptable carrier.

The above discussion relating to the preferred embodiments' utility and administration of the compounds of the present invention also applies to the pharmaceutical composition of the present invention.

The term "pharmaceutically acceptable carrier" as used herein refers to any carrier, diluent, excipient, suspending agent, lubricating agent, adjuvant, vehicle, delivery system emulsifier, disintegrant, absorbent, preservative, surfactant, colorant, flavorant, or sweetener.

For these purposes, the composition of the invention may be administered orally, parenterally, by inhalation spray, adsorption, absorption, topically, rectally, nasally, bucally, vaginally, intraventricularly, via an implanted reservoir in dosage formulations containing conventional non-toxic pharmaceutically-acceptable carriers, or by any other convenient dosage form The term parenteral as used herein includes subcutaneous, intravenous, intramuscular, intraperitoneal, intrathecal intraventricular, intrasternal, and intracranial injection or infusion techniques.

When administered parenterally, the composition will normally be in a unit dosage, sterile injectable form (solution, suspension or emulsion) which is preferably isotonic with the blood of the recipient with a pharmaceutically acceptable carrier. Examples of such sterile injectable forms are sterile injectable aqueous or oleaginous suspensions. These suspensions may be formulated according to techniques known in the art using suitable dispersing or wetting agents and suspending agents. The sterile injectable forms may also be sterile injectable solutions or suspensions in non-toxic parenterally-acceptable diluents or solvents, for example, as solutions in 1,3-butanediol. Among the acceptable vehicles and solvents that may be employed are water, saline, Ringer's solution, dextrose solution, isotonic sodium chloride solution, and Hanks' solution. In addition, sterile, fixed oils are conventionally employed as solvents or suspending mediums. For this purpose, any bland fixed oil may be employed including synthetic mono- or di-glycerides, corn, cottonseed, peanut, and sesame oil. Fatty acids such as ethyl oleate, isopropyl myristate, and oleic acid and its glyceride derivatives, including olive oil and castor oil, especially in their polyoxyethylated versions, are useful in the preparation of injectables. These oil solutions or suspensions may also contain long-chain alcohol diluents or dispersants.

Sterile saline is a preferred carrier, and the compounds are often sufficiently water soluble to be made up as a solution. The carrier may contain minor amounts of additives, such as substances that enhance solubility, isotonicity, and chemical stability, e.g., anti-oxidants, buffers and preservatives.

Formulations suitable for nasal or buccal administration (such as self-propelling powder dispensing formulations) may comprise about 0.1% to about 5% w/w, for example 1% w/w of active ingredient. The formulations for human medical use of the present invention comprise an active ingredient in association with a pharmaceutically acceptable carrier therefore and optionally other therapeutic ingredient(s).

When administered orally, the composition will usually be formulated into unit dosage forms such as tablets, cachets, powder, granules, beads, chewable lozenges, capsules, liquids, aqueous suspensions or solutions, or similar dosage forms, using conventional equipment and techniques known in the art. Such formulations typically include a solid, semisolid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, and the like.

The composition of the invention is preferably administered as a capsule or tablet containing a single or divided dose of the compound of Formula (I) or pharmaceutically acceptable salt thereof. The composition may be administered as a sterile solution, suspension, or emulsion, in a single or divided dose. Tablets may contain carriers such as lactose and corn starch, and/or lubricating agents such as magnesium stearate. Capsules may contain diluents including lactose and dried corn starch.

A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent Molded tablets may be made by molding in a suitable machine, a mixture of the powdered active ingredient and a suitable carrier moistened with an inert liquid diluent.

The compounds of this invention may also be administered rectally in the form of suppositories. These compositions can be prepared by mixing the drug with a suitable non-irritating excipient which is solid at room temperature, but liquid at rectal temperature, and, therefore, will melt in the rectum to release the drug. Such materials include cocoa butter, beeswax, and polyethylene glycols.

Compositions and methods of the invention also may utilize controlled release technology. Thus, for example, the disclosed compounds may be incorporated into a hydrophobic polymer matrix for controlled release over a period of days. The composition of the invention may then be molded into a solid implant, or externally applied patch, suitable for providing efficacious concentrations of the PARP inhibitors over a prolonged period of time without the need for frequent re-dosing. Such controlled release films are well known to the art. Particularly preferred are transdermal delivery systems. Other examples of polymers commonly employed for this purpose that may be used in the present invention include nondegradable ethylene-vinyl acetate copolymer a degradable lactic acid-glycolic acid copolymers which may be used externally or internally. Certain hydrogels such as poly(hydroxyethylmethacrylate) or poly(vinylalcohol) also may be useful, but for shorter release cycles than the other polymer release systems, such as those mentioned above.

In an embodiment, the carrier is a solid biodegradable polymer or mixture of biodegradable polymers with appropriate time release characteristics and release kinetics. The composition of the invention may then be molded into a solid implant suitable for providing efficacious concentrations of the compounds of the invention over a prolonged period of time without the need for frequent re-dosing. The composition of the present invention can be incorporated into the biodegradable polymer or polymer mixture in any suitable manner known to one of ordinary skill in the art and may form a homogeneous matrix with the biodegradable polymer, or may be encapsulated in some way within the polymer, or may be molded into a solid implant.

In one embodiment, the biodegradable polymer or polymer mixture is used to form a soft "depot" containing the pharmaceutical composition of the present invention that can be administered as a flowable liquid, for example, by injection, but which remains sufficiently viscous to maintain the pharmaceutical composition within the localized area around the injection site. The degradation time of the depot so formed can be varied from several days to a few years, depending upon the polymer selected and its molecular weight. By using a polymer composition in injectable form even the need to make an incision may be eliminated. In any event, a flexible or flowable delivery "depot" will adjust to the shape of the space it occupies with the body with a minimum of trauma to surrounding tissues. The pharmaceutical composition of the present invention is used in amounts that are therapeutically effective, and may depend upon the desired release profile, the concentration of the pharmaceutical composition required for the sensitizing effect, and the length of time that the pharmaceutical composition has to be released for treatment.

The compounds of the invention are used in the composition in amounts that are therapeutically effective. The compositions may be sterilized and/or contain adjuvants, such as preserving, stabilizing, welling, or emulsifying agents, solution promoters, salts for regulating the osmotic pressure, and/or buffers. In addition, they may also contain other therapeutically valuable substances, such as, without limitation, the specific chemotherapeutic agents recited herein. The compositions are prepared according to conventional mixing, granulating, or coating methods, and contain about 0.1 to 75% by weight, preferably about 1 to 50% by weight, of the compound of the invention.

To be effective therapeutically as central nervous system targets, the compounds of the present invention should readily penetrate the blood-brain barrier when peripherally administered. Compounds which cannot penetrate the blood-brain barrier can be effectively administered by an intraventricular route or other appropriate delivery system suitable for administration to the brain.

For medical use, the amount required of the active ingredient to achieve a therapeutic effect will vary with the particular compound, the route of administration, the mammal under treatment, and the particular disorder or disease being treated. A suitable systematic dose of a compound of the present invention or a pharmacologically acceptable salt thereof for a mammal suffering from or likely to suffer from, any of condition as described hereinbefore is in the range of about 0.1 mg/kg to about 100 mg/kg of the active ingredient compound, the typical dosage being about 1 to about 10 mg/kg.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

It is understood that the ordinarily skilled physician or veterinarian will readily determine and prescribe the effective amount of the compound for prophylactic or therapeutic treatment of the condition for which treatment is administered. In so proceeding, the physician or veterinarian can, for example, employ an intravenous bolus followed by an intravenous infusion and repeated administrations, parenterally or orally, as considered appropriate. While it is possible for an active ingredient to be administered alone, it is preferable to present it as a formulation.

When preparing dosage form incorporating the compositions of the invention, the compounds may also be blended with conventional excipients such as binders, including gelatin, pregelatinized starch, and the like; lubricants, such as hydrogenated vegetable oil, stearic acid, and the like; diluents, such as lactose, mannose, and sucrose; disintegrants, such as carboxymethylcellulose and sodium starch glycolate; suspending agents, such as povidone, polyvinyl alcohol, and the like; absorbants, such as silicon dioxide; preservatives, such as methylparaben, propylparaben, and sodium benzoate; surfactants, such as sodium lauryl sulfate, polysorbate 80, and the like; colorants; flavorants; and sweeteners. Pharmaceutically acceptable excipients are well known in the pharmaceutical arts and are described, for example, in Remington's Pharmaceutical Sciences, Mack Publishing Co., Easton, Pa. (e.g., 20$^{th}$ Ed., 2000), and Handbook of Pharmaceutical Excipients, American Pharmaceutical Association, Washington, D.C., (e.g., 1$^{st}$, 2$^{nd}$ and 3$^{rd}$ Eds., 1986, 1994, and 2000, respectively).

The present invention relates to the use of a compound of Formula (I) in the preparation of a medicament for the treatment of any disease or disorder in an animal described herein. In an embodiment, the compounds of the present invention are used to treat cancer. In a preferred embodiment, the compounds of the present invention are used to potentiate the cytotoxic effects of ionizing radiation. In such an embodiment, the compounds of the present invention act as a radiosensitizer. In an alternative preferred embodiment, the compounds of the present invention are used to potentiate the cytotoxic effects of chemotherapeutic agents. In such an embodiment, the compounds of the present invention act as a chemosensitizer. In another preferred embodiment, the compounds of the present invention are used to inhibit the growth of cells having defects in the homologous recombination (HR) pathway of double-stranded DNA repair.

Any pharmacologically-acceptable chemotherapeutic agent that acts by damaging DNA is suitable as the chemotherapeutic agent of the present invention. In particular, the present invention contemplates the use of a chemotherapeutically effective amount of at least one chemotherapeutic agent including, but not limited to: temozolomide, adriamycin, camptothecin, carboplatin, cisplatin, daunorubicin, docetaxel, doxorubicin, interferon-alpha, interferon-beta, interferon-gamma, interleukin 2, irinotecan, paclitaxel, topotecan, a taxoid, dactinomycin, danorubicin, 4'-deoxydoxorubicin, bleomycin, pilcamycin, mitomycin, neomycin, gentamycin, etoposide 4-OH cyclophosphamide, a platinum coordination complex, topotecan, and mixtures thereof. According to a preferred aspect, the chemotherapeutic agent is temozolomide.

The invention contained herein demonstrates the usefulness of the compounds and compositions of the present invention in treating and/or preventing cancer, such as by radiosensitizing and/or chemosensitizing tumor and/or cancer cells to chemotherapeutic agents, and to inhibit the growth of cells having defects in the homologous recombination (HR) pathway of double-stranded DNA repair.

The following examples are for illustrative purposes only and are not intended to limit the scope of the application.

In one embodiment, the present invention provides a tetraaza phenalen-3-one compound of Formula (I), or a pharmaceutically acceptable salt thereof:

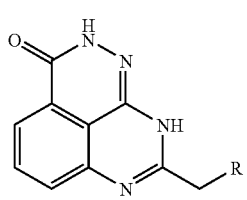

(I)

wherein R is
(a) $NR^1R^2$, wherein $R^1$ is selected from the group consisting of hydrogen, $C_1$-$C_6$ straight or branched chain alkyl, $C_2$-$C_6$ straight or branched chain alkenyl, $C_3$-$C_8$ cycloalkyl, $C_1$-$C_6$ alkoxy, $C_2$-$C_6$ alkenyloxy, phenyl, phenoxy, benzyloxy, $NR^AR^B$ ($C_1$-$C_6$ straight or branched chain alkyl), $NR^AR^B$ ($C_2$-$C_6$ straight or branched chain alkenyl), ($C_1$-$C_6$ straight or branched chain alkyl)carbonyl, ($C_2$-$C_6$ straight or branched chain alkenyl)carbonyl, ($C_3$-$C_8$ cycloalkyl)carbonyl, ($C_1$-$C_6$ straight or branched chain alkyl)oxycarbonyl, ($C_2$-$C_6$ straight or branched chain alkenyl)oxycarbonyl, ($C_3$-$C_8$ cycloalkyl)oxycarbonyl, arylcarbonyl, sulfonyl, arylsulfonyl, aryl($C_1$-$C_6$ straight or branched chain alkyl), aryl($C_2$-$C_6$ straight or branched chain alkenyl), aryl($C_3$-$C_8$ cycloalkyl), ($C_1$-$C_6$ straight or branched chain alkyl)aryl, ($C_2$-$C_6$ straight or branched chain alkenyl)aryl, ($C_3$-$C_8$ cycloalkyl)aryl, aryl, heterocyclyl, heterocyclyl($C_1$-$C_6$ straight or branched chain alkyl), and heterocyclyl($C_2$-$C_6$ straight or branched chain alkenyl); wherein each heterocyclyl has between 1 and 7 heteroatoms independently selected from O, N, or S, and wherein each of $R^A$ and $R^B$ are independently selected from the group consisting of hydrogen, $C_1$-$C_6$ straight or branched chain alkyl, $C_2$-$C_6$ straight or branched chain alkenyl, and $C_3$-$C_8$ cycloalkyl;

and $R^2$ is selected from the group consisting of $C_1$-$C_6$ straight or branched chain alkyl, $C_2$-$C_6$ straight or branched chain alkenyl, $C_3$-$C_8$ cycloalkyl, $C_1$-$C_6$ alkoxy, $C_2$-$C_6$ alkenyloxy, phenyl, phenoxy, benzyloxy, $NR^XR^Y$ ($C_1$-$C_6$ straight or branched chain alkyl), $NR^XR^Y$ ($C_2$-$C_6$ straight or branched chain alkenyl), ($C_1$-$C_6$ straight or branched chain alkyl)carbonyl, ($C_2$-$C_6$ straight or branched chain alkenyl)carbonyl, ($C_3$-$C_8$ cycloalkyl)carbonyl, ($C_1$-$C_6$ straight or branched chain alkyl)oxycarbonyl, ($C_2$-$C_6$ straight or branched chain alkenyl)oxycarbonyl, ($C_3$-$C_8$ cycloalkyl)oxycarbonyl, arylcarbonyl, sulfonyl, arylsulfonyl, aryl($C_1$-$C_6$ straight or branched chain alkyl), aryl ($C_2$-$C_6$ straight or branched chain alkenyl), aryl($C_3$-$C_8$ cycloalkyl), ($C_1$-$C_6$ straight or branched chain alkyl)aryl, ($C_2$-$C_6$ straight or branched chain alkenyl)aryl, ($C_3$-$C_8$ cycloalkyl)aryl, aryl, heterocyclyl, heterocyclyl($C_1$-$C_6$ straight or branched chain alkyl), and heterocyclyl($C_2$-$C_6$ straight or branched chain alkenyl); wherein each heterocyclyl has between 1 and 7 heteroatoms independently selected from O, N, or S, and wherein each of $R^X$ and $R^Y$ are independently selected from the group consisting of hydrogen, $C_1$-$C_6$ straight or branched chain alkyl, $C_2$-$C_6$ straight or branched chain alkenyl, and $C_3$-$C_8$ cycloalkyl;

wherein $R^1$ and $R^2$ are independently substituted with between 0 and 4 substituents, each independently selected from halo, $C_1$-$C_6$ straight or branched chain alkyl, $C_2$-$C_6$ straight or branched chain alkenyl, $C_1$-$C_6$ alkoxy, trifluoromethyl, trifluoroethyl, and amino; and provided that $R^1$ and $R^2$ may not both be methyl, and $R^2$ may not be (phenyl)prop-1-yl when $R^1$ is hydrogen; or (b) aryloxy, substituted with between 0 and 4 substituents, each independently selected from the group consisting of halo, $C_1$-$C_6$ alkoxy, trifluoromethyl, trifluoroethyl, $C_1$-$C_6$ straight or branched chain alkyl, $C_2$-$C_6$ straight or branched chain alkenyl, $C_3$-$C_8$ cycloalkyl, $NR^CR^D$, $NR^CR^D$($C_1$-$C_6$ straight or branched chain alkyl), and $NR^CR^D$($C_2$-$C_6$ straight or branched chain alkenyl), wherein each of $R^C$ and $R^D$ is independently selected from the group consisting of hydro gen, $C_1$-$C_6$ straight or branched chain alkyl, $C_2$-$C_6$ straight or branched chain alkenyl, and $C_3$-$C_8$ cycloalkyl; and when more than one substituent is of the form $NR^CR^D$, each occurrence of $R^C$ and $R^D$ is independently selected from the group consisting of hydrogen, $C_1$-$C_6$ straight or branched chain alkyl, $C_2$-$C_6$ straight or branched chain alkenyl, and $C_3$-$C_8$ cycloalkyl; or (c) a heterocyclyl having between 1 and 7 heteroatoms independently selected from O, N, or S; and having between 0 and 4 substituents independently selected from the group consisting of halo, haloalkyl, hydroxyl, nitro, trifluoromethyl, trifluoroethyl, $C_1$-$C_6$ straight or branched chain alkyl, $C_2$-$C_6$ straight or branched chain alkenyl, $C_1$-$C_6$ alkoxy, $C_2$-$C_6$ alkenyloxy, phenyl, phenoxy, benzyloxy, amino, thiocarbonyl, cyano, imino, $NR^ER^F$($C_1$-$C_6$ straight or branched chain alkyl), $NR^ER^F$($C_2$-$C_6$ straight or branched chain alkenyl) sulflhydryl, thioalkyl, dioxa-spiroethyl, ($C_1$-$C_6$ straight or branched chain alkyl) carbonyl, ($C_2$-$C_6$ straight or branched chain alkenyl)carbonyl, ($C_1$-$C_6$ straight or branched chain alkyl)oxycarbonyl, ($C_2$-$C_6$ straight or branched chain alkenyl)oxycarbonyl, arylcarbonyl, sulfonyl, arylsulfonyl, aryl($C_1$-$C_6$ straight or branched chain alkyl), aryl($C_2$-$C_6$ straight or branched chain alkenyl), aryl($C_3$-$C_8$ cycloalkyl), ($C_1$-$C_6$ straight or branched chain alkyl)aryl, ($C_2$-$C_6$ straight or branched chain alkenyl)aryl, ($C_3$-$C_8$ cycloalkyl)aryl, aryl, heterocyclyl, heterocyclyl($C_1$-$C_6$ straight or branched chain alkyl), and heterocyclyl($C_2$-$C_6$ straight or branched chain alkenyl), wherein each heterocyclyl has between 1 and 7 heteroatoms independently selected from O, N, or S, wherein each of $R^E$ and $R^F$ is independently selected from the group consisting of hydrogen, $C_1$-$C_6$ straight or branched chain alkyl, $C_2$-$C_6$ straight or branched chain alkenyl, and $C_3$-$C_8$ cycloalkyl; and when more than one substituent is of the form $NR^ER^F$ each occurrence of $R^E$ and $R^F$ is independently selected from the group consisting of hydrogen, $C_1$-$C_6$ straight or branched chain alkyl, $C_2$-$C_6$ straight or branched chain alkenyl, and $C_3$-$C_8$ cycloalkyl; wherein each of said 0-4 substituents is independently substituted with between 0 and 4 further substituents, and each said further substituent is independently selected from halo, $C_1$-$C_6$ straight or branched chain alkyl, $C_2$-$C_6$ straight or branched chain alkenyl, $C_3$-$C_8$ cycloalkyl, $C_1$-$C_6$ alkoxy, trifluoromethyl, trifluoroethyl, and amino; provided that R has at least one substituent when R is an N-piperidinyl, N-pyrrolidinyl or an N-morpholinyl group.

In some embodiments each ring of each heterocycle of Formula (I) is independently 5-7 atoms in size.

Some embodiments include one, two or three nitrogen atoms in at least one ring of the heterocycle of Formula (I).

In some embodiments, the heterocyclyl of Formula (I) comprises 1-3 rings. In some embodiments, the heterocyclyl has 1-7 heteroatoms independently selected from O, N, and S.

In some embodiments, the heterocyclyl of Formula (I) is selected from the group consisting of piperidinyl, piperazinyl, pyridazinyl, dihydropyridyl, tetrahydropyridyl, pyridinyl, pyrimidinyl, dihydropyrimidinyl, tetrahydrophyrimidinyl, hexahydropyrimidinyl, dihydropyrazinyl, tetrahydropyrazinyl, pyrrolidinyl, imidazolidinyl, pyrazolidinyl, pyrrolyl, dihydropyrolyl, imidazolyl, dihydroimidazoyl, pyrazolyl, dihydropyrazolyl, azepanyl, [1,2]diazepanyl, [1,3]diazepanyl, [1,4]diazepanyl, indolyl, dihydroindolyl, isoindolyl, dihydroisoindoly, dihydroquinolyl, tetrahydroquinolyl, dihydroisoquinolyl, and tetrahydroisoquinolyl.

In another embodiment, the present invention provides a compound selected from the group consisting of

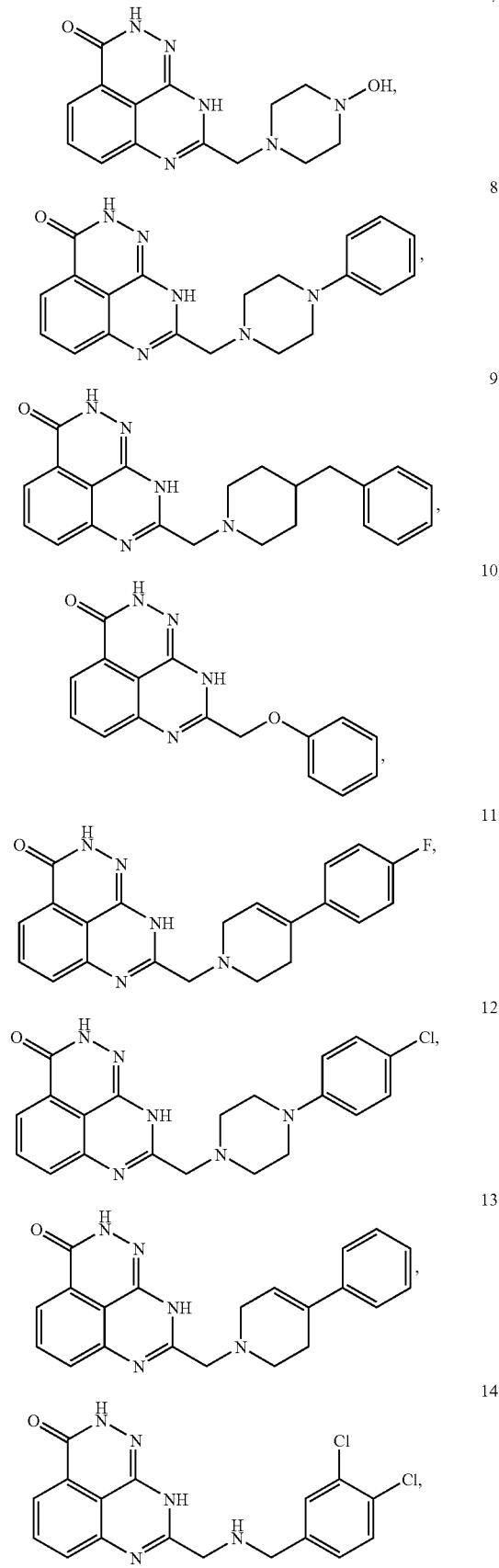

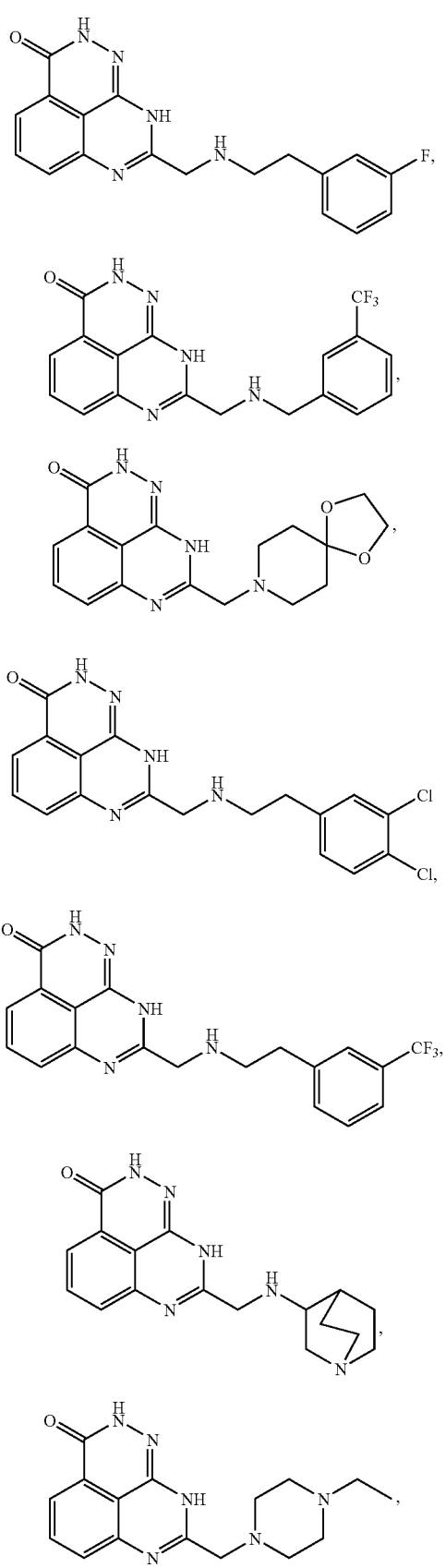
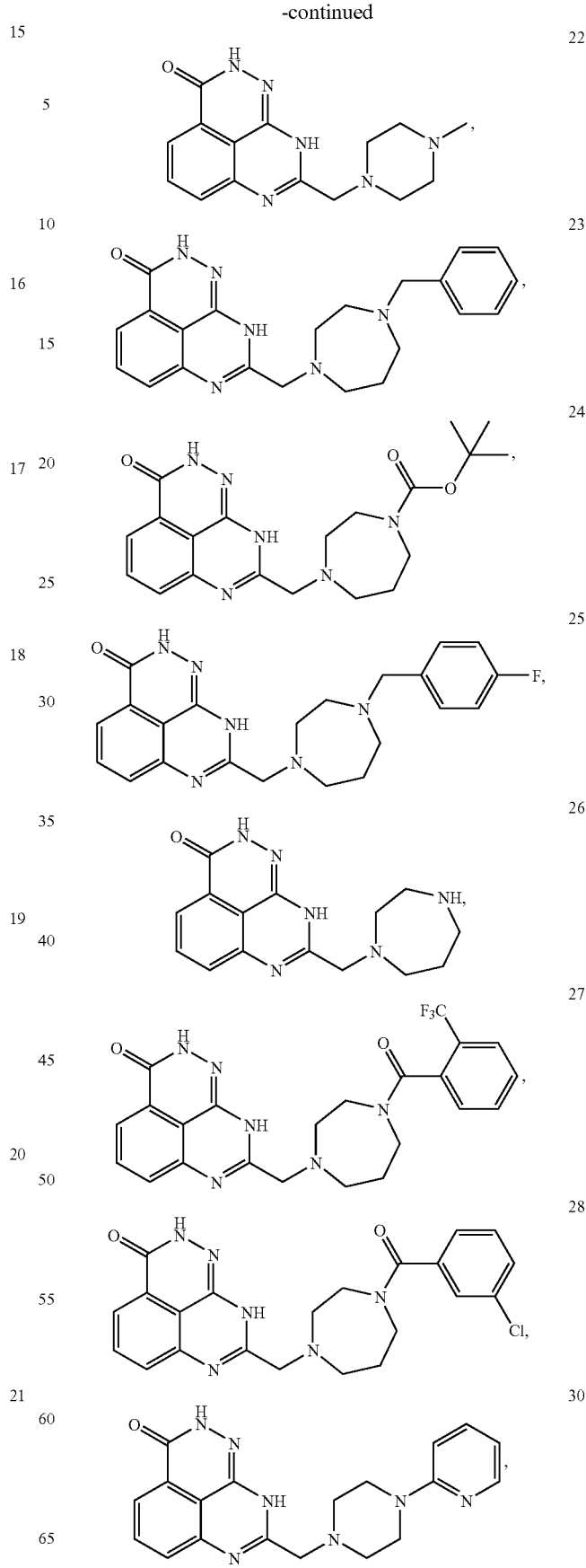

-continued

31

32

33

34

35

36

37

-continued

38

39

40

41

42

43

44

45
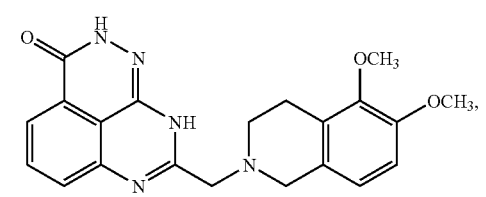
46
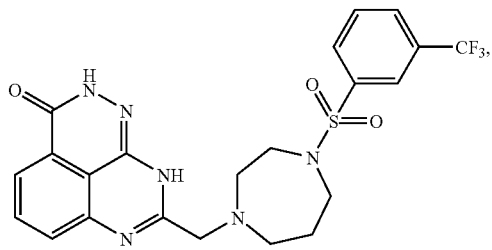
50
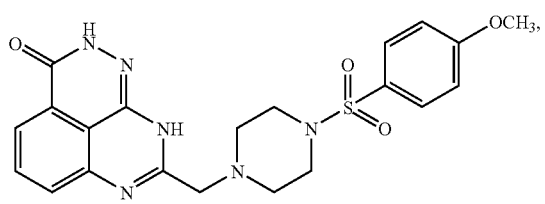
51
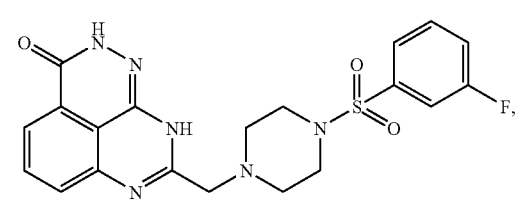
52
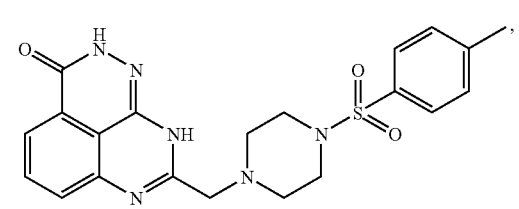
53
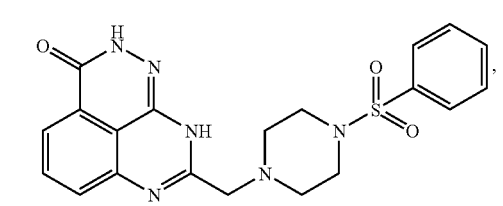
54
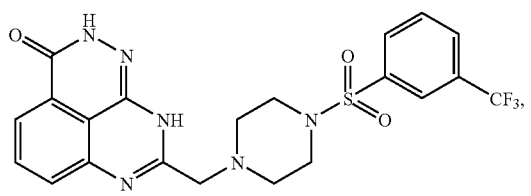
55
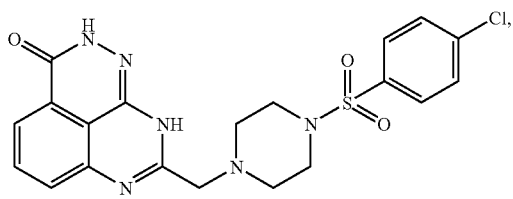
56
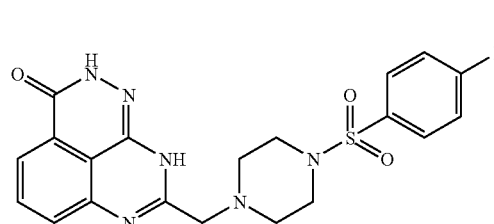
57
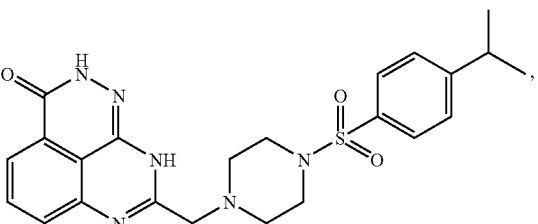
58
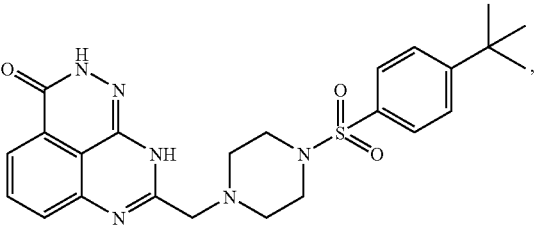
59
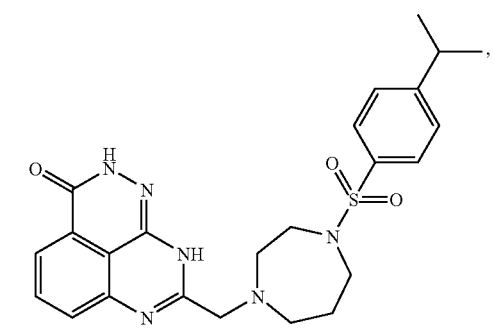
60
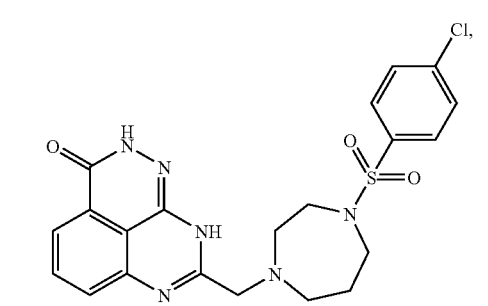

-continued
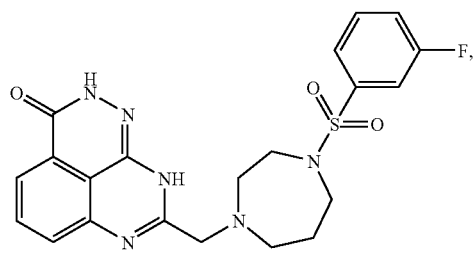
61
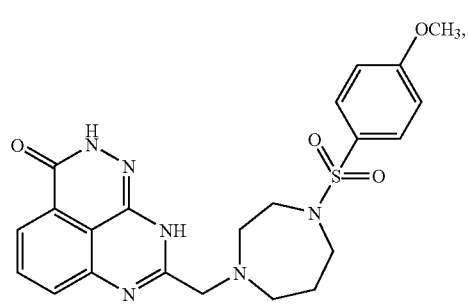
62
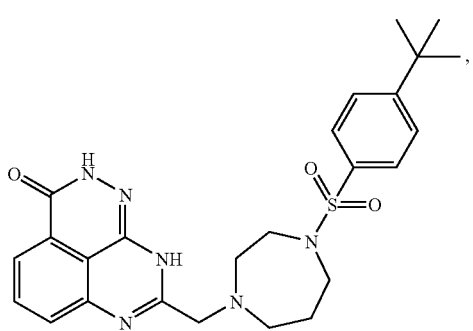
63
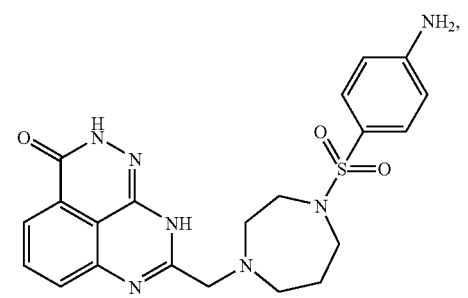
64
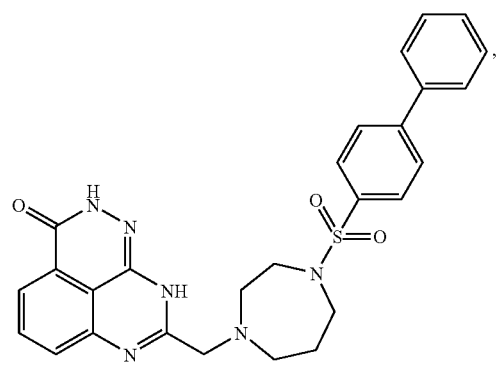
65
-continued
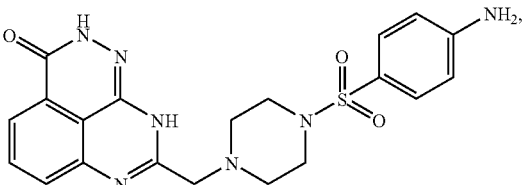
66
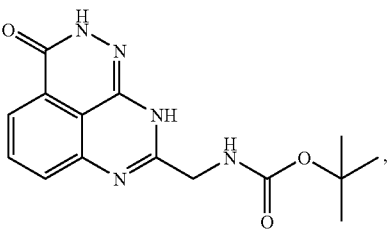
69
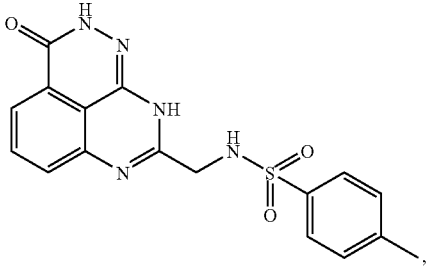
72
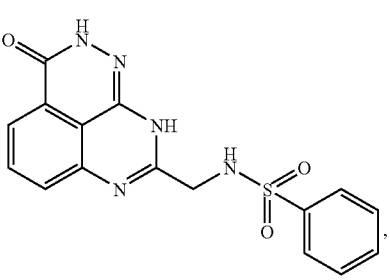
74
75
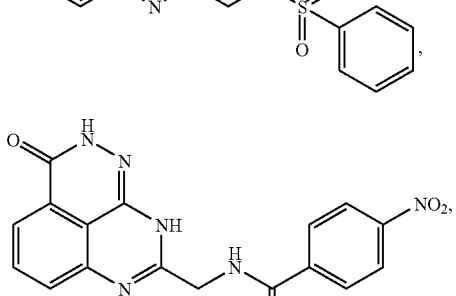
76
and pharmaceutically acceptable salts thereof.

In some embodiments the invention provides the compound which is

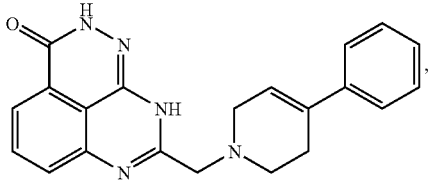

13 or a pharmaceutically acceptable salt thereof.

In some embodiments the invention provides the compound which is

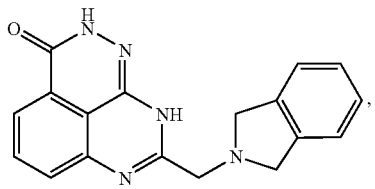

37 or a pharmaceutically acceptable salt thereof.

In some embodiments the present invention provides a method of chemosensitizing cancer cells in a mammal in need of chemotherapy, comprising administering to said mammal a compound of Formula (I) as described herein, or a pharmaceutically acceptable salt thereof. In some embodiments, said mammal is a human. In some embodiments, said administration is administration of a pharmaceutical composition comprising said compound and a pharmaceutically acceptable carrier. In some embodiments, the chemosensitization method further comprises administering to said mammal a chemotherapeutic agent. In some embodiments, said chemosensitizing compound and said chemotherapeutic agent are administered essentially simultaneously.

In some embodiments the present invention provides a method of chemosensitizing cancer cells in a mammal in need of chemotherapy, comprising administering to said mammal a compound selected from the group consisting of compounds 7-28, 30-46, 50-66, 69, 72, 74-76, and pharmaceutically acceptable salts thereof, as described herein. In some embodiments, said mammal is a human. In some embodiments, said administration is administration of a pharmaceutical composition comprising said compound and a pharmaceutically acceptable carrier. In some embodiments, the chemosensitization method further comprises administering to said mammal a chemotherapeutic agent. In some embodiments, said chemosensitizing compound and said chemotherapeutic agent are administered essentially simultaneously.

In some embodiments, the chemotherapeutic agent of the invention is selected is selected from the group consisting of temozolomide, adriamycin, camptothecin, carboplatin, cisplatin, daunorubicin, docetaxel, doxorubicin, interferon-alpha, interferon-beta, interferon-gamma, interleukin 2, irinotecan, paclitaxel, topotecan, a taxoid, dactinomycin, danorubicin, 4'-deoxydoxorubicindeoxydoxorubicin, bleomycin, pilcamycin, mitomycin, neomycin, gentamycin, etoposide, 4-OH cyclophosphamide, a platinum coordination complex, and mixtures thereof. In some embodiments, the chemotherapeutic agent is temozolomide or a salt thereof.

In some embodiments, the present invention provides a method of radiosensitizing cancer cells in a mammal in need of radiation therapy comprising administering to said mammal a compound of Formula (I) as described herein, or a pharmaceutically acceptable salt thereof. In some embodiments, said mammal is a human. In some embodiments, said administration is administration of a pharmaceutical composition comprising said compound and a pharmaceutically acceptable carrier.

In some embodiments, the present invention provides a method of radiosensitizing cancer cells in a mammal in need of radiation therapy comprising administering to said mammal a compound selected from the group consisting of compounds 7-28, 30-46, 50-66, 69, 72, 74-76, and pharmaceutically acceptable salts thereof, as described herein. In some embodiments, said mammal is a human. In some embodiments, said administration is administration of a pharmaceutical composition comprising said compound and a pharmaceutically acceptable carrier.

In some embodiments, the invention provides a pharmaceutical composition comprising a compound of Formula (I) as described herein, or a pharmaceutically acceptable salt thereof, and a pharmaceutically acceptable carrier. In some embodiments, the pharmaceutical composition further comprises a chemotherapeutic agent as described herein.

In some embodiments, the invention provides a pharmaceutical composition comprising a compound selected from the group consisting of compounds 7-28, 30-46, 50-66, 69, 72, 74-76, and pharmaceutically acceptable salts thereof, as described herein. In some embodiments, the pharmaceutical composition further comprises a chemotherapeutic agent as described herein.

In some embodiments, the cancer cells treated by the chemosensitizing and/or radiosensitizing methods of the invention are selected from the group consisting of ACTH-producing tumors, acute lymphocytic leukemia, acute non-lymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head and neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovarian cancer, ovary (germ cell) cancer, prostate cancer, pancreatic cancer, penile cancer, retinoblastoma, skin cancer, soft-tissue sarcoma, squamous cell carcinomas, stomach cancer, testicular cancer, thyroid cancer, trophoblastic neoplasms, uterine cancer, vaginal cancer, cancer of the vulva and Wilm's tumor. In some embodiments, the cancer cells treated by the chemosensitizing and/or radiosensitizing methods of the invention are selected from the group consisting of brain cancer, melanoma, head and neck cancer, testicular cancer, ovarian cancer, breast cancer, non small cell lung cancer, and rectal cancer.

In some embodiments, the invention provides a method of treating a mammal having a cancer characterized by having a defect in the homologous recombination (HR) pathway of double-stranded DNA repair, comprising administering to said mammal a compound of Formula (I) as described herein, or a pharmaceutically acceptable salt thereof. In some embodiments, said mammal is a human. In some embodiments, said administration is administration of a pharmaceutical composition comprising said compound and a pharmaceutically acceptable carrier. In some embodiments, the cancer cells have a phenotype selected from the group consisting of i) a BRCA-1 defect, ii) a BRCA-2 defect, iii) a BRCA-1 and BRCA-2 defect, and iv) Fanconi anemia. In some embodiments, the cancer cells are selected from breast cancer or ovarian cancer.

In some embodiments, the invention provides a method of treating a mammal having a cancer characterized by having a defect in the homologous recombination (HR) pathway of double-stranded DNA repair, comprising administering to said mammal a compound selected from the group consisting of compounds 7-28, 30-46, 50-66, 69, 72, 74-76, and pharmaceutically acceptable salts thereof, as described herein. In some embodiments, said mammal is a human. In some embodiments, said administration is administration of a pharmaceutical composition comprising said compound and a pharmaceutically acceptable carrier. In some embodiments, the cancer cells have a phenotype selected from the group consisting of i) a BRCA-1 defect, ii) a BRCA-2 defect, iii) a BRCA-1 and BRCA-2 defect, and iv) Fanconi anemia. In some embodiments, the cancer cells are selected from breast cancer or ovarian cancer.

Synthetic Procedures for the Disclosed Compounds

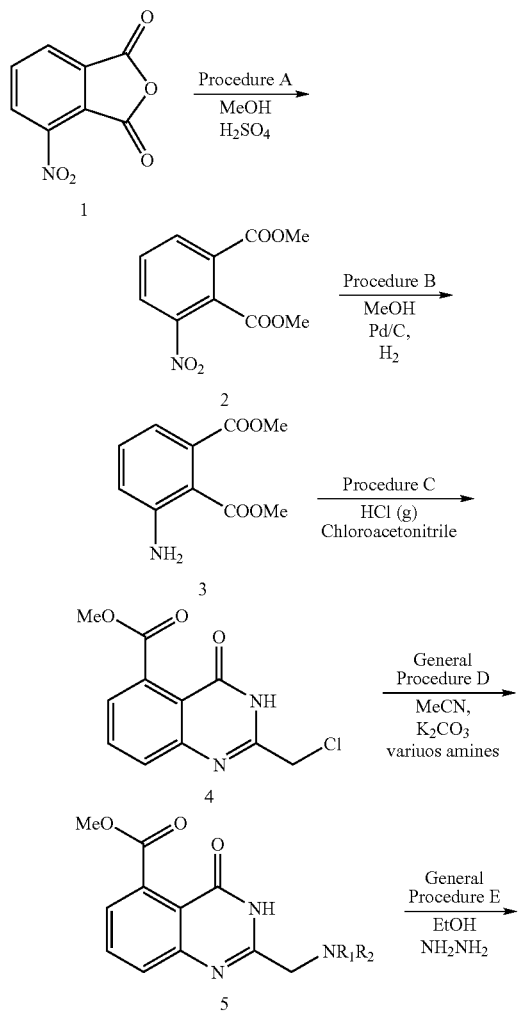

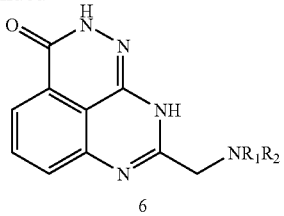

Procedure A: Preparation of 3-nitro-phthalic Acid Dimethyl Ester, 2

To a stirred solution of 4-nitro-isobenzofuran-1,3-dione (150 g, 0.78 mol), 1, in 2 L of MeOH was added 50 mL of concentrated sulfuric acid. The reaction was heated to reflux for 16 hours. The mixture solution was cooled to room temperature and then poured into 3 L of ice water and resulted in a heavy white precipitate. This was triturated for 15 minutes and the precipitated was filtered off and the solid was washed with water thoroughly and dried to afford 120 g of 3-nitro-phthalic acid dimethyl ester, 2, as a white solid (65%). $^1$H NMR (300 MHz, DMSO-$d_6$): 8.54 (d, J=7.25 Hz, 1H), 8.42 (d, J=7.82 Hz, 1H), 7.98 (t, J=8.20 Hz, 1H), 3.99 (s, 3H), 3.98 (s, 3H). $^{13}$C NMR: 52.03, 52.29, 111.02, 115.67, 119.08, 131.80, 133.68, 148.80, 167.64, 168.63.

Procedure B: Preparation of 3-amino-phthalic Acid Dimethyl Ester, 3

The compound 2 (205 g, 1.0 mol) was dissolved in 2 L of MeOH. Catalytic 10% Pd/C was added and the solution was hydrogenated under $H_2$ (45 psi) on a Parr hydrogenation apparatus at room temperature overnight. Filtered through celite and evaporated to give a quantitative yield of 3-amino-phthalic acid dimethyl ester, 3. $^1$H NMR (300 MHz, DMSO-$d_6$): 7.26 (t, J=7.33 Hz, 1H), 6.94 (d, J=8.34 Hz, 1H), 6.77 (d, J=8.33 Hz, 1H), 6.12 (s, 2H), 3.77 (s, 3H), 3.76 (s, 3H). $^{13}$C NMR: 51.51, 51.77, 110.50, 115.16, 118.56, 131.26, 133.16, 148.28, 167.12, 168.11.

Procedure C: Preparation of 2-chloromethyl-4-oxo-3,4-dihydro-quinazoline-5-carboxylic Acid Methyl Ester, 4

100 mL of chloroacetonitrile was set stirring in 130 mL of 1,4 dioxane at room temperature. Dry HCl gas was bubbled through the solution for thirty minutes followed by the addition of 30 g of 3-amino-1,2-phthalic acid dimethyl ester, 3. The reaction was refluxed for approximately three hours, resulting in a heavy white precipitate. The suspension was cooled with an ice bath, filtered and washed with pentane to remove any residual solvents. 30 g (83%) of an analytically pure white solid, 4, was isolated. $^1$H NMR (300 MHz, DMSO-$d_6$): 7.88 (t, J=8.33 Hz, 1H), 7.79 (d, J=7.08 Hz, 1H), 7.52 (d, J=7.33 Hz, 1H), 4.60 (s, 2H), 3.84 (s, 3H); $^{13}$C NMR: 42.21, 54.86, 119.95, 127.77, 130.86, 135.71, 136.78, 150.59, 155.70, 162.49, 171.24.

General Procedure D: Preparation of Compounds, 5

Displacement of the chloro group of compound 4 with nucleophiles such as amine using General procedure D provides the compounds 5. To a solution of the chloro compound 4 in dry DMF or MeCN is added potassium carbonate and a nucleophile such as an amine. The reaction mixture is heated to 70° C. for 12 hours and cooled to room temperature. Water is added to the reaction mixture, followed by ethyl acetate. The organic layer is collected, washed with water, brine and dried over sodium sulfate. The solvents are removed in vacuum. The residue is purified by column chromatography on silica gel using ethyl acetate/hexanes as eluent to give the products 5 in 50-95% yield. An example was given in the preparation of compound 7.

General Procedure E: Preparation of Compounds, 6

A 2,9-Dihydro-1,2,7,9-tetraaza-phenalen-3-one ring can be formed by condensation of the compounds 6 with hydrazine. To a solution of the compounds 6 in absolute ethanol is added excess anhydrous hydrazine at room temperature. The solution is refluxed for overnight and cooled to room temperature. Ice-cold water is added and white solid is separated. The solid is collected by vacuum filtration and washed with water and small amount of methanol to give white solid products 6 in 40-90% yield. An example was given in the preparation of compound 7.

Example 1

Preparation of 8-(4-hydroxy-piperidin-1-ylmethyl)-2,9-dihydro-1,2,7,9-tetraaza-phenalen-3-one, 7

Following the General Procedure D: A solution of MeCN (25 ml), 4-hydroxypiperidine (0.46 mg, 4.5 mmol), 4 (1.0 g, 3.9 mmol), and potassium carbonate (1 g, 7 mmol) was set refluxing under nitrogen and stirred overnight. Reaction mixture was evaporated to dryness and extracted with dichloromethane. Purified with a silica column using 9:1 dichloromethane/MeOH to afford 1.05 g (84%) of an off-white solid, 2-(4-Hydroxy-piperidin-1-ylmethyl)-4-oxo-3,4-dihydro-quinazoline-5-carboxylic acid methyl ester, 7a.

Following the General Procedure E: To a solution of compound 7a (1.0 g, 3.1 mmol) in EtOH (20 mL) when refluxing was added hydrazine monohydrate (7 mL, large excess) and heated overnight. Reaction was cooled to RT and $H_2O$ (15 mL) was added resulting in a heavy white precipitate. Filtered and washed with 1:1 $EtOH/H_2O$ to afford 0.6 g (64%) of an analytically pure white solid, 7. MP: 168-171° C.; MS (ES+): 300; $^1$H NMR (300 MHz, $CD_3OD$): 1.46-1.55 (m, 2H), 1.71-1.75 (m 2H) 2.15-2.23 (m 2H) 2.70-2.75 (m, 2H) 3.16-3.18 (m, 1H) 3.25 (s, 2H) 3.47-3.55 (m, 1H) 7.30-7.33 (m, 1H) 7.60-7.64 (m, 2H). Anal. Calcd. for $C_{15}H_{17}N_5O_2.1.7 H_2O$: C, 56.45; H, 6.06; N, 21.94; Found: C, 56.10; H, 6.00; N, 22.25.

The compound 7 can be formulated with an acid. For example: to a solution of 7 (0.6 g, 2.0 mmol) in 10 mL of 1,4 dioxane/DMF (9:1) at 90° C. was added MsOH (0.14 mL, 2.1 mmol) resulting in a heavy white precipitate. Filtered and triturated in diethyl ether to afford 0.5 g (63%) of an off-white solid, mesylate salt of 7. $^1$H NMR (300 MHz, DMSO-$d_6$): 1.55-1.58 (m 2H), 1.78-1.82 (m, 2H), 2.15 (s, 3H), 3.15-3.50 (m 4H), 3.63-3.65 (m, 1H), 4.04 (s, 2H), 7.24 (d, J=8.5 Hz, 1H), 7.51-7.66 (m 2H), 11.73 (s, 1H)

Anal. Calcd. for $C_{15}H_{17}N_5O_2.1CH_3SO_3H. 2H_2O$: C, 44.54; H, 5.84; N, 16.23, S, 7.43; Found: C, 44.48; H, 5.76; N, 16.27, S, 7.60.

The following compounds were synthesized from the similar procedures of preparation of compound 7, using the appropriate corresponding amines.

Preparation of 8-(4-phenyl-piperazin-1-ylmethyl)-2,9-dihydro-1,2,7,9-tetraaza-phenalen-3-one, 8

Synthesized using 1-phenylpiperazine for General Procedure D. 52% overall yield for last two steps. MS (ES+): 361; $^1$H NMR (300 MHz, DMSO-$d_6$): 2.65-2.68 (m, 4H), 3.19-3.22 (m, 4H) 3.39 (s, 2H); 6.78 (t, J=7.2 Hz, 1H); 6.95 (d, J=8.0 Hz, 2H), 7.19 (t, J=7.2 Hz, 2H), 7.48-7.51 (m, 1H), 7.62-7.64 (d, J=7.2 Hz, 1H), 7.75 (t, J=8.0 Hz, 1H), 11.23 (s, br, 1H), 11.78 (s, 1H); Anal. Calcd. for $C_{20}H_{20}N_6O_1.2.0H_2O$: C, 60.59; H, 6.10; N, 21.20; Found: C, 60.48; H, 6.05; N, 21.35.

Preparation of 8-(4-benzyl-piperidin-1-ylmethyl)-2,9-dihydro-1,2,7,9-tetraaza-phenalen-3-one, 9

Synthesized using 1-benzylpiperazine for General Procedure D. 20% overall yield for last two steps. MS (ES−): 372; $^1$H NMR (300 MHz, DMSO-$d_6$): 1.22-1.50 (m, 5H), 2.45-2.55 (m, 4H), 2.85 (d, 2H), 3.28 (s, 2H), 7.14-7.19 (m, 3H), 7.25-7.30 (m 2H), 7.50 (d, J=7.0 Hz, 1H), 7.62 (d, J=7.7 Hz, 1H), 7.75 (t, J=7.7 Hz, 1H), 11.25 (s, br, 1H), 11.76 (s, 1H); Anal. Calcd. for $C_{22}H_{23}N_5O_1$: C, 70.76; H, 6.21; N, 18.75; Found: C, 70.36; H, 6.18; N, 18.63.

Preparation of 8-phenoxymethyl-2,9-dihydro-1,2,7,9-tetraaza-phenalen-3-one, 10

Synthesized using phenol for General Procedure D. 60% overall yield for last two steps. MS (ES+): 293; $^1$H NMR (300 MHz, DMSO-$d_6$): 4.90 (s, br, 3H), 7.00 (t, J=6.6 Hz, 1H), 7.08 (d, J=8.2 Hz, 2H), 7.34 (t, J=7.7 Hz, 2H), 7.45 (d, J=7.7 Hz, 1H), 7.65 (d, J=7.7 Hz, 1H), 7.76 (t, J=7.2 Hz, 1H), 11.20 (s, br, 1H), 11.80 (s, 1H). Anal. Calcd. for $C_{16}H_{12}N_4O_2.0.75 H_2O. 0.25 N_2H_4$: C, 61.24; H, 4.66; N, 20.08; Found: C, 61.06; H, 4.27; N, 20.13;

Preparation of 8-(4-(4-fluoro-phenyl)-3,6-dihydro-2H-pyridin-1-ylmethyl)-2,9-dihydro-1,2,7,9-tetraaza-phenalen-3-one, 11

Synthesized using 4-(4-fluorophenyl)-1,2,3,6-tetrahydropyridine hydrochloride for General Procedure D. 24% overall yield for last two steps. MS (ES+): 376; $^1$H NMR (400 MHz, DMSO-$d_6$): 2.51-2.53 (s, br, 2H), 2.77 (t, J=5.4 Hz, 2H), 3.24 (s, br, 2H), 3.46 (s, 2H), 6.16 (m, 1H), 7.16 (t, J=8.8 Hz, 2H), 7.46-7.52 (m, 3H), 7.63 (d, J=7.8 Hz, 1H), 7.44 (t, J=7.8 Hz, 1H), 11.18 (s, br, 1H), 11.79 (s, 1H). A mesylate salt of 11 was prepared. $^1$H NMR (400 MHz, DMSO-$d_6$): 2.34 (s, 3H), 2.84 (bs, 2H), 3.66 (m 2H), 4.11 (m, 2H), 4.36 (s, 2H), 6.21 (m, 1H), 7.25 (t, J=8.8 Hz, 2H), 7.43 (d, J=7.4 Hz, 1H), 7.56-7.59 (m, 2H), 7.72 (d, J=7.4 Hz, 1H), 7.82 (t, J=7.5 Hz, 1H), 11.25 (s, br, 1H), 11.76 (s, 1H). Anal. Calcd. for $C_{21}H_{18}FN_5O_1.1.0 CH_3SOH. 0.2 H_2O$: C, 55.62; H, 4.75; N, 14.74; S, 6.75; Found: C, 55.65; H, 4.71; N, 14.73; S, 6.74.

Preparation of 8-[4-(4-chloro-phenyl)-piperazin-1-ylmethyl]-2,9-dihydro-1,2,7,9-tetraaza-phenalen-3-one, 12

Synthesized using 1-(4-chlorophenyl)-piperazine for General Procedure D. 23% overall yield for last two steps. A mesylate salt of 12 was prepared. MS (ES+): 396; $^1$H NMR (400 MHz, DMSO-$d_6$): 2.33 (s, 3H), 4.31 (s, 2H), 7.03 (d, J=9.3 Hz, 2H), 7.31 (d, J=9.3 Hz, 2H), 7.43 (d, J=8.5 Hz, 1H), 7.72 (d, J=8.5 Hz, 1H), 7.82 (t, J=7.9 Hz, 1H), 11.23 (s, br, 1H), 11.90 (s, 1H). Anal. Calcd. for $C_{20}H_{19}ClN_6O_1.1.0 CH_3SOH$: C, 51.37; H, 4.72; N, 17.12; S, 6.53; Found: C, 51.27; H, 4.91; N, 17.03; S, 6.48.

Preparation of 8-(4-phenyl-3,6-dihydro-2H-pyridin-1-ylmethyl)-2,9-dihydro-1,2,7,9-tetraaza-phenalen-3-one, 13

Synthesized using 4-phenyl-1,2,3,6-tetrahydro-pyridine for General Procedure D. 80% overall yield for last two steps. MS (ES+): 358; $^1$H NMR (400 MHz, DMSO-d$_6$): 2.56 (m, 2H), 2.78 (t, J=5.5 Hz, 2H), 3.25 (d, J=2.6 Hz, 2H), 3.47 (s, 2H), 6.19 (s, 1H), 7.23-7.27 (m, 1H), 7.24 (t, J=7.6 Hz, 2H), 7.45 (d, J=7.1 Hz, 2H), 7.51 (d, J=8.9 Hz, 1H), 7.62 (d, J=7.1 Hz, 1H), 7.75 (t, J=8.0 Hz, 1H), 11.27 (s, 1H), 11.78 (s, 1H). A mesylate salt of 13 was prepared. $^1$H NMR (400 MHz, DMSO-d$_6$): 2.34 (s, 3H), 2.84-2.88 (m, 2H), 3.65-3.69 (m, 2H), 4.13 (s, 2H), 4.37 (s, 2H), 6.21-6.25 (m, 1H), 7.32-7.44 (m, 4H), 7.53 (d, J=8.6 Hz, 2H), 7.72 (d, J=7.3 Hz, 1H), 7.82 (t, J=8.1 Hz, 1H), 11.30 (s, br, 1H), 11.93 (s, 1H). Anal. Calcd. for C$_{21}$H$_{19}$N$_5$O. 1.0 CH$_3$SOH. 0.4 H$_2$O: C, 57.35; H, 5.21; N, 15.20; S, 6.96; Found: C, 57.30; H, 5.16; N, 15.29; S, 7.10;

Preparation of 8-[(3,4-dichloro-benzylamino)-methyl]-2,9-dihydro-1,2,7,9-tetraaza-phenalen-3-one, 14

Synthesized using 3,4-dichlorobenzylamine for General Procedure D. 10% overall yield for last two steps. A mesylate salt of 14 was prepared. MS (ES+): 375; $^1$H NMR (300 MHz, DMSO-d$_6$): 2.33 (s, 3H), 4.06 (s, 2H), 4.33 (s, 2H), 7.39 (d, J=8.0 Hz, 1H), 7.53-7.57 (m, 1H), 7.69-7.88 (m, 4H), 11.31 (s, br, 1H), 11.91 (s, 1H).

Preparation of 8-{[2-(3-Fluoro-phenyl)-ethylamino]-methyl}-2,9-dihydro-1,2,7,9-tetraaza-phenalen-3-one, 15

Synthesized using 3-fluorophenethylamine for General Procedure D. 12% overall yield for last two steps. A mesylate salt of 15 was prepared. MS (ES+): 338; $^1$H NMR (300 MHz, DMSO-d$_6$): 2.34 (s, 3H), 3.02-3.08 (m, 2H), 3.34-3.38 (m, 2H), 4.14 (s, 2H), 7.08-7.18 (m, 3H), 7.37-7.44 (m, 2H), 7.71 (d, J=7.8 Hz, 1H), 7.82 (t, J=7.8 Hz, 1H), 11.92 11.35 (s, br, 1H), (s, 1H).

Preparation of 8-[(3-trifluoromethyl-benzylamino)-methyl]-2,9-dihydro-1,2,7,9-tetraaza-phenalen-3-one, 16

Synthesized using 3-(trifluoromethyl)benzylamine for General Procedure D. 14% overall yield for last two steps. A mesylate salt of 16 was prepared. MS (ES+): 374; $^1$H NMR (300 MHz, DMSO-d$_6$): 2.33 (s, 3H), 4.10 (s, 2H), 4.43 (s, 2H), 7.39 (d, J=7.6 Hz, 1H), 7.69-7.86 (m, 5H), 7.99 (s, 1H), 11.25 (s, br, 1H), 11.91 (s, 1H). Anal. Calcd. for C$_{19}$H$_{18}$F$_3$N$_5$O. 1.0 CH$_3$SOH. 1.0 H$_2$O: C, 46.82; H, 4.14; N, 14.37; S, 6.58; Found: C, 46.81; H, 4.17; N, 14.64; S, 6.35.

Preparation of 8-(1,4-dioxa-8-aza-spiro[4.5]dec-8-ylmethyl)-2,9-dihydro-1,2,7,9-tetraaza-phenalen-3-one, 17

Synthesized using 4-piperidone ethylene ketal for General Procedure D. 10% overall yield for last two steps. MS (ES−): 370; $^1$H NMR (300 MHz, DMSO-d$_6$): 1.69-1.71 (m, 4H), 2.57 (s, br, 4H), 3.35 (s, 2H), 3.87 (s, 4H), 7.51 (d, J=7.8 Hz, 1H), 7.62 (d, J=7.7 Hz, 1H), 7.74 (t, J=7.8 Hz, 1H), 11.23 (s, br, 1H), 11.76 (s, 1H). Anal. Calcd. for C$_{17}$H$_{19}$N$_5$O$_3$.0.2 H$_2$O: C, 59.19; H, 5.67; N, 20.30; Found: C, 59.03; H, 5.60; N, 20.63.

Preparation of 8-{[2-(3,4-dichloro-phenyl)-ethylamino]-methyl}-2,9-dihydro-1,2,7,9-tetraaza-phenalen-3-one, 18

Synthesized using 3,4-dichlorophenethylamine for General Procedure D. 17% overall yield for last two steps. A mesylate salt of 18 was prepared. MS (ES−): 387; $^1$H NMR (300 MHz, DMSO-d$_6$): 2.36 (s, 3H), 3.04 (t, J=8.2 Hz, 2H), 3.37 (t, J=8.1 Hz, 2H), 4.14 (s, 2H), 7.30-7.43 (m, 2H), 7.61-7.75 (m, 3H), 7.79-7.84 (m, 1H), 11.31 (s, br, 1H), 11.91 (s, 1H).

Preparation of 8-{[2-(3-trifluoromethyl-phenyl)-ethylamino]-methyl}-2,9-dihydro-1,2,7,9-tetraaza-phenalen-3-one, 19

Synthesized using 2-(3-Trifluoromethyl-phenyl)-ethylamine for General Procedure D. 39% overall yield for last two steps. A mesylate salt of 19 was prepared. MS (ES−): 387; $^1$H NMR (300 MHz, DMSO-d$_6$): 3.74 (s, 3H), 3.13 (t, J=8.1 Hz, 2H), 3.30 (t, J=8.2 Hz, 2H), 4.15 (s, 2H), 7.40-7.43 (m, 1H), 7.62-7.72 (m, 4H), 7.79-7.85 (m, 1H), 11.35 (s, br, 1H), 11.92 (s, 1H).

Preparation of 8-[(1-Aza-bicyclo[2.2.2]oct-3-ylamino)-methyl]-2,9-dihydro-1,2,7,9-tetraaza-phenalen-3-one, 20

Synthesized using (S)-(−)-3-aminoquinuclidine for General Procedure D. 23% overall yield for last two steps. A mesylate salt of 20 was prepared. MS (ES+): 325; $^1$H NMR (300 MHz, DMSO-d$_6$): 1.97-2.03 (m, 3H), 2.20-2.35 (m, 1H), 2.35-2.44 (m, 2H), 2.42 (s, 3H), 3.72-3.80 (m, 6H), 4.15-4.21 (m, 1H), 4.38 (s, 2H), 7.46 (d, J=7.6, 1H) 7.69-7.72 (m, 1H), 7.78-7.84 (m, 1H), 8.63 (s, br, 3H).

Preparation of 8-(4-ethyl-piperazin-1-ylmethyl)-2,9-dihydro-1,2,7,9-tetraaza-phenalen-3-one, 21

Synthesized using ethylpiperazine for General Procedure D. 35% overall yield for last two steps. A mesylate salt of 21 was prepared. MS (ES+): 313; $^1$H NMR (300 MHz, DMSO-d$_6$): 1.25, (t, J=7.4 Hz, 3H), 2.41 (s, 6H), 2.51-3.87 (m, 10H), 3.87 (s, 2H), 7.70 (d, J=8.0 Hz, 1H), 7.81 (d, J=7.9 Hz, 1H), 7.91 (t, J=8.1 Hz, 1H), 9.82 (s, 1H), 11.96 (s, 1H). $^{13}$C NMR (DMSO-d$_6$): 157.40, 155.99, 140.65, 135.96, 133.84, 126.72, 119.71, 118.65, 115.85, 56.09, 50.30, 49.05, 48.66, 8.51. Anal. Calcd. for C$_{16}$H$_{20}$N$_6$O. 2.0 CH$_3$SO$_3$H. 1.2 H$_2$O.: C, 40.84; H, 5.43; N, 15.79; Found: C, 41.09; H, 5.82; N, 15.97.

Preparation of 8-(4-methyl-piperazin-1-ylmethyl)-2,9-dihydro-1,2,7,9-tetraaza-phenalen-3-one, 22

Synthesized using methylpiperazine for General Procedure D. 29% overall yield for last two steps. A mesylate salt of 22 was prepared. MS (ES+): 299; $^1$H NMR (400 MHz, DMSO-d$_6$): 2.38 (s, 3H), 2.58-2.63 (m, 2H), 3.09-3.18 (m, 4H), 3.40-3.45 (m, 2H), 3.51 (s, 2H), 7.50 (d, J=7.8 Hz, 1H), 7.67 (d, J=7.8 Hz, 1H), 7.79 (t, J=7.8 Hz, 1H), 9.53 (s, br, 1H), 11.85 (s, 1H). Anal. Calcd. for C$_{15}$H$_{18}$N$_6$O. 1.15 CH$_3$SO$_3$H. 1.0 H$_2$O.: C, 45.44; H, 5.81; N, 19.69; S, 8.64; Found: C, 45.18; H, 5.88; N, 19.83; S, 8.68;

Preparation of 8-(4-benzyl-[1,4]diazepan-1-ylmethyl)-2,9-dihydro-1,2,7,9-tetraaza-phenalen-3-one, 23

Synthesized using 1-benzyl-[1,4]diazepane for General Procedure D. 24% overall yield for last two steps. MP: 140-

142° C.; MS (ES−): 387; $^1$H NMR (400 MHz, CDCl$_3$): 1.88 (m, 2H), 2.77 (m, 4H), 2.89 (m, 4H), 3.62 (s, 2H), 3.69 (s, 2H), 7.20-7.42 (m, 6H), 7.45 (s, br, 1H), 7.74 (t, J=7.8 Hz, 1H), 7.87 (d, J=7.6 Hz, 1H), 11.50 (s, br, 1H); Anal. Calcd. for C$_{22}$H$_{24}$N$_6$O. 1.35 H$_2$O.: C, 64.01; H, 6.52; N, 20.36; Found: C, 64.18; H, 6.59; N, 20.46.

An HCl salt of 23 was prepared: to a solution of 23 (0.5 g) in 20 mL of dioxane was bubbled HCl gas for 30 min. The solution was stirred at room temperature overnight. After filtration, the precipitate was washed with dioxane to afford 0.25 g (48%) of analytically pure off white solid, an HCl salt of 23. $^1$H NMR (400 MHz, D$_2$O): 2.08 (m, 2H), 3.36 (m, 4H), 3.56 (m, 4H), 4.04 (s, 2H), 4.24 (s, 2H), 7.02 (d, 1H), 7.20-7.35 (m, 5H); 7.36 (d, 1H), 7.45 (t, 1H); Anal. Calcd. for C$_{22}$H$_{24}$N$_6$O. 2.0HCl. 1.15 H$_2$O.: C, 54.81; H, 5.92; N, 17.43; Found: C, 54.81; H, 5.92; N, 17.36.

Preparation of 4-(3-oxo-2,9-dihydro-3H-1,2,7,9-tetraaza-phenalen-8-ylmethyl)-[1,4]diazepane-1-carboxylic Acid Tert-Butyl Ester, 24

Synthesized using [1,4]diazepane-1-carboxylic acid t-butyl ester for General Procedure D. 30% overall yield for last two steps. MP: 219-221° C.; MS (ES−): 397; $^1$H NMR (400 MHz, CDCl$_3$): 1.46 (s, 9H); 1.88 (m, 2H); 2.83 (m, 4H); 3.50 (m, 4H); 3.59 (s, 2H); 7.63 (m, 1H); 7.72-7.86 (m, 3H), 11.90 (s, br, 1H). Anal. Calcd. for C$_{20}$H$_{26}$N$_6$O$_3$.0.5 H$_2$O.: C, 58.95; H, 6.68; N, 20.62; Found: C, 58.83; H, 6.69; N, 20.60.

Preparation of 8-[4-(4-fluoro-benzyl)-[1,4]diazepan-1-ylmethyl]-2,9-dihydro-1,2,7,9-tetraaza-phenalen-3-one, 25

Synthesized using 1-(4-fluoro-benzyl)-[1,4]diazepane for General Procedure D. 35% overall yield for last two steps. MP: 163-165° C.; MS (ES−): 405; $^1$H NMR (400 MHz, CDCl$_3$): 1.87 (m, 2H), 2.72 (m, 4H), 2.88 (m, 4H), 3.63 (s, 2H), 3.65 (s, 2H), 6.99 (t, J=8.4 Hz, 2H), 7.30 (m, 3H) 7.61 (s, br, 1H), 7.78 (m, 1H); 7.93 (d, J=7.3 Hz 1H), 10.82 (s, br, 1H). Anal. Calcd. for C$_{22}$H$_{23}$N$_6$O. 1.5 H$_2$O.: C, 60.96; H, 6.05; N, 19.39; Found: C, 61.07; H, 5.97; N, 19.59.

A mesylate salt of 25 was prepared. $^1$H NMR (400 MHz, D$_2$O): 2.06 (m, 2H), 2.70 (s, 3H), 3.06 (m, 2H), 3.24 (m, 2H), 3.46 (m, 4H), 3.65 (s, 4H), 3.74 (s, 2H), 4.33 (s, 2H), 7.25 (m, 3H), 7.46 (m, 3H), 7.62 (t, J=8.4 Hz, 1H). Anal. Calcd. for C$_{22}$H$_{23}$FN$_6$O. 1.3 CH$_3$SO$_3$H. 0.5 C$_4$H$_8$O$_2$.2.0 H$_2$O.: C, 49.70; H, 5.97; N, 13.74; S, 6.82; Found: C, 49.40; H, 5.97; N, 13.37; S, 6.65.

Preparation of 8-[1,4]diazepan-1-ylmethyl-2,9-dihydro-1,2,7,9-tetraaza-phenalen-3-one, 26

Synthesized from compound 24. To a solution of 24 (1.5 g, 3.7 mmol) in 30 mL of CH$_2$Cl$_2$ was added 6 mL of TFA while stirring at room temperature. After 30 minutes, the solvents were evaporated and the residue was washed with acetonitrile to afford 1.0 g (90%) of analytically pure white solid. MP: 147-149° C.; MS (ES−): 297; $^1$H NMR (400 MHz, D$_2$O): 1.96 (m, 2H), 2.82 (t, 2H), 3.01 (t, 2H), 3.28 (t, 4H), 3.53 (s, 2H), 7.22 (d, 1H), 7.47 (d, 1H), 7.61 (t, 1H). Anal. Calcd. for C$_{15}$H$_{18}$N$_6$O. 1.1 CF$_3$CO$_2$H. 1.0 H$_2$O.: C, 46.76; H, 4.81; N, 19.02; Found: C, 46.64; H, 4.98; N, 19.02.

Preparation of 8-[4-(2-trifluoromethyl-benzoyl)-[1,4]diazepan-1-ylmethyl]-2,9-dihydro-1,2,7,9-tetraaza-phenalen-3-one, 27

Synthesized from compound 26. To a solution of compound 26 (0.2 g, 0.6 mmol) in 5 mL of CH$_2$Cl$_2$ was added 1 mmol of TEA and 0.8 mmol of 2-trifluoromethyl-benzoyl chloride. The reaction was stirred overnight at room temperature. After the solvents were evaporated, the residue was purified with semi-preparative HPLC to afford a solid (15% yield). MP: 140-142° C.; MS (ES−): 469; $^1$H NMR (400 MHz, CDCl$_3$): 1.92-2.10 (m, 2H), 2.91-3.10 (m, 4H), 3.36-3.44 (m, 2H), 3.64-3.74 (m, 2H), 3.93 (m, 2H), 7.38 (m, 1H), 7.57 (m, 3H), 7.79 (m, 2H), 7.93 (m, 1H). Anal. Calcd. for C$_{23}$H$_{21}$F$_3$N$_6$O$_2$.0.9HCl: C, 54.89; H, 4.39; N, 16.70; Found: C, 54.93; H, 4.43; N, 16.34.

Preparation of 8-[4-(3-chloro-benzoyl)-[1,4]diazepan-1-ylmethyl]-2,9-dihydro-1,2,7,9-tetraaza-phenalen-3-one, 28

Synthesized from compound 26. To a solution of compound 26 (0.2 g, 0.6 mmol) in 5 mL of CH$_2$Cl$_2$ was added 1 mmol of TEA and 0.8 mmol of 3-chloro-benzoyl chloride. The reaction was stirred overnight at room temperature. After the solvents were evaporated, the residue was purified with semi-preparative HPLC to afford a solid (16% yield). MP: 147-149° C.; MS (ES−): 436; $^1$H NMR (400 MHz, CDCl$_3$): 1.88-2.08 (m, 2H), 2.86-3.07 (m, 4H), 3.52-3.71 (m, 4H), 3.81-3.89 (m, 2H), 7.33-7.43 (m, 4H), 7.62 (d, 1H), 7.81 (t, 1H), 7.90 (t, 1H). Anal. Calcd. for C$_{22}$H$_{21}$ClN$_6$O$_2$.0.7H$_2$O: C, 54.89; H, 4.39; N, 16.70; Found: C, 54.93; H, 4.43; N, 16.34.

Preparation of 8-(4-pyridin-2-yl-piperazin-1-ylmethyl)-2,9-dihydro-1,2,7,9-tetraaza-phenalen-3-one, 30

Synthesized using 1-pyridin-2-yl-piperazine for General Procedure D. 20% overall yield for last two steps. A mesylate salt of 30 was prepared. MS (ES−): 360; $^1$H NMR (400 MHz, DMSO-d$_6$): 2.37 (s, 6H), 3.52 (s, br, 4H), 3.93 (s, br, 4H), 4.30 (s, 2H), 6.93 (t, J=6.6 Hz, 1H), 7.25 (d, J=8.6 Hz, 1H), 7.47 (d, J=7.8 Hz, 1H), 7.73 (d, J=7.8 Hz, 1H), 7.82-7.91 (m, 2H), 8.16-8.18 (m, 1H), 11.96 (s, 1H). Anal. Calcd. for C$_{19}$H$_{19}$N$_7$O. 1.9 CH$_3$SO$_3$H. 1.2 H$_2$O.: C, 44.38; H, 5.17; N, 17.33; S, 10.77; Found: C, 44.21; H, 5.19; N, 17.28; S, 10.68.

Preparation of 8-{[2-(2-fluoro-phenyl)-ethylamino]-methyl}-2,9-dihydro-1,2,7,9-tetraaza-phenalen-3-one, 31

Synthesized using 2-(2-fluoro-phenyl)-ethylamine for General Procedure D. 20% overall yield for last two steps. A mesylate salt of 31 was prepared. MS (ES−): 336; $^1$H NMR (400 MHz, DMSO-d$_6$): 2.41 (s, 5H), 3.02 (t, J=7.6 Hz, 2H), 3.32 (t, J=8.3 Hz, 2H), 4.16 (s, 2H), 7.19 (t, J=8.8 Hz, 2H), 7.32-7.35 (m, 2H), 7.42 (d, J=7.8 Hz, 1H), 7.71 (d, J=7.8 Hz, 1H), 7.82 (t, J=8.1 Hz, 1H), 9.10 (s, br, 1H), 11.92 (s, 1H). Anal. Calcd. for C$_{18}$H$_{16}$FN$_5$O. 1.75 CH$_3$SO$_3$H. 0.75 H$_2$O: C, 45.70; H, 4.76; N, 13.49; S, 10.81; Found: C, 45.45; H, 4.69; N, 13.42; S, 11.10.

Preparation of 8-[4-(4-fluoro-phenyl)-piperazin-1-ylmethyl]-2,9-dihydro-1,2,7,9-tetraaza-phenalen-3-one, 32

Synthesized using 4-(4-fluoro-phenyl)-piperazine for General Procedure D. 57% overall yield for last two steps. A mesylate salt of 32 was prepared. MS (ES−): 377; $^1$H NMR (400 MHz, DMSO-d$_6$): 2.40 (s, 5H), 3.45 (s, br, 4H), 3.59 (s, br, 4H), 4.37 (s, 2H), 7.03-7.15 (m, 4H), 7.44 (d, J=7.8 Hz, 1H), 7.72 (d, J=7.8 Hz, 1H), 7.83 (t, J=7.8 Hz, 1H), 9.8 (s, br, 1H), 11.94 (s, 1H). Anal. Calcd. for C$_{20}$H$_{19}$FN$_6$O. 1.65

CH₃SO₃H: C, 46.85; H, 5.01; N, 15.14; S, 9.53; Found: C, 46.74; H, 5.15; N, 15.14; S, 9.53.

Preparation of 8-{[2-(4-Fluoro-phenyl)-ethylamino]-methyl}-2,9-dihydro-1,2,7,9-tetraaza-phenalen-3-one, 33

Synthesized using 2-(4-fluoro-phenyl)-ethylamine for General Procedure D. 19% overall yield for last two steps. A mesylate salt of 33 was prepared. MS (ES−): 336; ¹H NMR (400 MHz, DMSO-d₆): 2.38 (s, 6H), 3.06-3.10 (m, 2H), 3.30-3.34 (m, 2H), 4.18 (s, 2H), 7.19-7.22 (m, 2H), 7.34-7.42 (m, 3H), 7.71 (d, J=8.6 Hz, 1H), 7.82 (t, J=7.8 Hz, 1H), 9.6 (s, br, 1H), 11.92 (s, 1H). Anal. Calcd. for C₁₈H₁₆FN₅O. 2.0 CH₃SO₃H: C, 45.36; H, 4.57; N, 13.22; S, 12.11; Found: C, 45.34; H, 4.58; N, 13.16; S, 11.88.

Preparation of 8-(4-acetyl-[1,4]diazepan-1-ylmethyl)-2,9-dihydro-1,2,7,9-tetraaza-phenalen-3-one, 34

Synthesized using [1,4]diazepane-1-yl-ethanone for General Procedure D. 16% overall yield for last two steps. MP: 191-193° C.; MS (ES−): 339; ¹H NMR (400 MHz, CDCl₃): 2.11 (s, 3H), 2.84-2.93 (m, 4H), 3.56-3.76 (m, 6H), 7.66 (m, 1H), 7.83-7.92 (m, 2H), 9.3 (s, br, 1H), 11.3 (s, br, 1H). Anal. Calcd. for C₁₇H₂₀N₆O₂.0.6H₂O: C, 58.14; H, 6.08; N, 23.93; Found: C, 58.09; H, 6.18; N, 24.08.

Preparation of 8-(phenethylamino-methyl)-2,9-dihydro-1,2,7,9-tetraaza-phenalen-3-one, 35

Synthesized using phenetyhlamine for General Procedure D. 29% overall yield for last two steps. A mesylate salt of 35 was prepared. MS (ES−): 358; ¹H NMR (400 MHz, DMSO-d₆): 2.32 (s, 3H), 3.00-3.04 (m, 2H), 3.31-3.36 (m, 2H), 4.15 (s, 1H), 7.27-7.42 (m, 6H), 7.71 (d, J=7.8 Hz, 1H), 7.82 (t, J=7.8 Hz, 1H), 9.70 (s, br, 1H), 11.92 (s, 1H). Anal. Calcd. for C₁₈H₁₇N₅O. 1.0 CH₃SO₃H. 1.8 H₂O: C, 50.95; H, 5.54; N, 15.64; S, 7.16; Found: C, 50.95; H, 5.54; N, 15.64; S, 7.16;

Preparation of 8-(4-phenyl-piperidin-1-ylmethyl)-2,9-dihydro-1,2,7,9-tetraaza-phenalen-3-one, 36

Synthesized using 4-phenyl-piperidine for General Procedure D. 33% overall yield for last two steps. MS (ES−): 318; ¹H NMR (400 MHz, DMSO-d₆): 1.87-1.93 (m, 4H), 2.37-2.46 (m, 2H), 2.56 (m, 1H), 3.10-3.14 (m, 2H), 3.54 (s, 2H), 7.17-7.34 (m, 5H), 7.56 (bs, 1H), 7.76 (t, J=7.8 Hz, 1H), 7.93 (d, J=7.8 Hz, 1H), 11.10 (s, br, 1H), 11.76 (s, 1H). A mesylate salt of 36 was prepared. ¹H NMR (400 MHz, D₂O): 2.08 (m, 4H), 2.95 (m, 1H), 3.34 (m, 2H), 3.84 (m, 2H), 4.23 (s, 2H), 7.21-7.39 (m, 6H), 7.59 (m, 1H), 7.70 (m, 1H). Anal. Calcd. for C₂₁H₂₁N₅O. 1.3 CH₃SO₃H. 0.5 H₂O: C, 54.29; H, 5.56; N, 14.19; S, 8.45; Found: C, 54.03; H, 5.65; N, 13.98; S, 8.64.

Preparation of 8-(1,3-dihydro-isoindol-2-ylmethyl)-2,9-dihydro-1,2,7,9-tetraaza-phenalen-3-one, 37

Synthesized using isoindoline for General Procedure D. 40% overall yield for last two steps. MS (ES−): 316; ¹H NMR (400 MHz, DMSO-d₆): 3.77 (s, 2H), 4.04 (s, 4H), 7.20-7.30 (m, 4H), 7.49 (d, J=7.8 Hz, 1H), 7.6 (d, J=7.8 Hz, 1H), 7.74 (t, J=7.8 Hz, 1H), 11.34 (s, br, 1H), 11.78 (s, 1H). A mesylate salt of 37 was prepared. ¹H NMR (400 MHz, DMSO-d₆): 2.34 (s, 3H), 4.64 (s, 2H), 4.87 (s, 4H), 7.39-7.46 (m, 5H), 7.72 (d, J=7.8 Hz, 1H), 7.83 (t, J=8.1 Hz, 1H), 11.30 (s, br, 1H), 11.95 (s, 1H). Anal. Calcd. for C₁₈H₁₅N₅O. 1.25 CH₃SO₃H. 2.0 H₂O: C, 48.83; H, 5.11; N, 14.79; S, 8.46; Found: C, 48.80; H, 5.11; N, 14.97; S 8.71.

Preparation of 8-(4-benzenesulfonyl-[1,4]diazepan-1-ylmethyl)-2,9-dihydro-1,2,7,9-tetraaza-phenalen-3-one, 38

Synthesized from compound 26. To a solution of 26 (0.2 g, 0.67 mmol) in 5 mL of CH₂Cl₂ was added TEA (2 mmol) and benzensulfonyl chloride (1 mmol). The mixture was stirred at room temperature over night. After the solvents were evaporated, the residue was poured into 10 mL of H₂O and the product was purified by preparative HPLC to afford analytically pure white solid (5% yield). MP: 265-268° C.; MS (ES−): 437; ¹H NMR (400 MHz, DMSO-d₆): 1.79 (m, 2H), 2.50 (m, 4H), 2.79 (m, 4H), 3.51 (s, 2H), 7.44 (d, 1H), 7.62-7.79 (m, 7H), 11.1 (s, br, 1H), 11.75 (s, 1H). Anal. Calcd. for C₂₁H₂₂N₆O₃S. 0.5 H₂O: C, 56.36; H, 5.18; N, 18.78; S, 7.17; Found: C, 56.44; H, 5.12; N, 19.00; S, 7.19.

A mesylate salt of 38 was prepared. MS (ES+): 439; ¹H NMR (400 MHz, D₂O): 2.18 (m, 2H), 2.35 (s, 6H), 3.36 (m, 2H), 3.65 (m, 6H), 4.3 (s, 2H), 7.24 (d, 1H), 7.51-7.71 (m, 7H). Anal. Calcd. for C₂₁H₂₂N₆O₃S. 1.8 CH₃SO₃H. 1.0 H₂O: C, 43.50; H, 5.00; N, 13.35; S, 14.26; Found: C, 43.61; H, 5.00; N, 13.15; S, 14.59.

Preparation of 8-(4-pyridin-4-yl-piperazin-1-ylmethyl)-2,9-dihydro-1,2,7,9-tetraaza-phenalen-3-one, 39

Synthesized using 1-(4-pyridyl)piperazine for General Procedure D. 10% overall yield for last two steps. MS (ES−): 360; ¹H NMR (400 MHz, DMSO-d₆): 2.80 (t, J=5.0 Hz, 4H), 3.61 (t, J=5.0 Hz, 4H), 3.99 (s, 2H), 6.83 (d, J=7.1 Hz, 2H), 7.42-7.45 (m, 1H), 7.73-7.81 (m, 2H), 8.26 (d, J=7.1 Hz, 2H), 11.20 (s, br, 1H), 11.90 (s, 1H). An HCl salt of 39 was prepared. ¹H NMR (400 MHz, D₂O): 2.74-2.77 (m, 4H), 3.43 (s, 2H), 3.35-3.69 (m, 4H), 6.93 (d, J=7.1 Hz, 2H), 7.13 (d, J=8.0 Hz, 1H), 7.37 (d, J=7.8 Hz, 1H), 7.58 (t, J=7.8 Hz, 1H), 7.92 (d, J=7.1 Hz, 2H). Anal. Calcd. for C₁₉H₁₉N₇O. 1.0 HCl. 2.5H₂O: C, 51.53; H, 5.69; N, 22.14; Cl, 8.00; Found: C, 51.46; H, 5.69; N, 21.90; Cl, 8.27.

Preparation of 8-(4-benzyl-piperazin-1-ylmethyl)-2,9-dihydro-1,2,7,9-tetraaza-phenalen-3-one, 40

Synthesized using 4-benzyl-piperazine for General Procedure D. 12% overall yield for last two steps. MS (ES−): 373; ¹H NMR (400 MHz, DMSO-d₆): 2.44 (s, br, 4H), 3.35 (s, br, 4H), 3.48 (s, 2H), 7.23-7.34 (m, 5H), 7.49 (d, J=8.8 Hz, 1H), 7.62 (d, J=7.8 Hz, 1H), 7.74 (t, J=7.8 Hz, 1H), 11.10 (s, br, 1H), 11.77 (s, 1H). An HCl salt of 40 was prepared. ¹H NMR (400 MHz, D₂O): 2.54-2.70 (m, 2H), 3.10-3.50 (m, 6H), 3.48 (s, 2H), 4.35 (s, 2H), 7.20 (d, J=8.1 Hz, 1H), 7.45 (t, J=7.8 Hz, 1H), 7.47-7.51 (m, 5H), 7.62 (t, J=8.1 Hz, 1H). Anal. Calcd. for C₂₁H₂₂N₆O. 1.0 HCl. 2.5H₂O: C, 55.32; H, 6.19; N, 18.43; Found: C, 55.54; H, 6.08; N, 18.32.

Preparation of 8-(4-methyl-[1,4]diazepan-1-ylmethyl)-2,9-dihydro-1,2,7,9-tetraaza-phenalen-3-one, 41

Synthesized using 1-methyl-[1,4]diazepane for General Procedure D. 24% overall yield for last two steps. MS (ES−): 311; ¹H NMR (400 MHz, DMSO-d₆): 1.75 (m, 2H), 2.26 (s, 3H), 2.55 (m, 4H), 2.79 (m, 4H), 3.48 (s, 2H), 7.52 (d, J=8.2

Hz, 1H), 7.64 (d, J=7.2 Hz, 1H), 7.75 (t, J=8.1 Hz, 1H), 11.55 (s, 1H). Anal. Calcd. for $C_{16}H_{20}N_6O$. 0.95 $H_2O$: C, 58.33; H, 6.70; N, 25.51; Found: C, 58.32; H, 6.65; N, 25.53.

Preparation of 8-[4-(1H-indol-3-yl)-piperidin-1-ylmethyl]-2,9-dihydro-1,2,7,9-tetraaza-phenalen-3-one, 42

Synthesized using 3-piperidin-4-yl-1H-indole for General Procedure D. 19% overall yield for last two steps. MS (ES−): 397; $^1$H NMR (400 MHz, DMSO-$d_6$): 1.83-1.94 (m, 4H), 2.31 (m, 2H), 2.50 (s, 2H), 2.79-2.99 (m, 3H), 6.96-7.09 (m, 3H), 7.32 (d, J=8.1 Hz, 1H), 7.54-7.63 (m, 3H), 7.75 (t, J=7.3 Hz, 1H), 10.79 (s, 1H), 11.80 (s, 1H). A mesylate salt of 42 was prepared. $^1$H NMR (400 MHz, DMSO-$d_6$): 2.15 (m, 4H), 2.32 (s, 3H), 3.11 (m, 1H), 3.52 (m, 2H), 3.73 (m, 2H), 4.29 (s, 2H), 7.10-7.18 (m, 3H), 7.36 (d, 1H); 7.46 (d, J=8.2 Hz, 1H), 7.69-7.83 (m, 3H), 10.91 (s, 1H), 11.93 (s, 1H). Anal. Calcd. for $C_{23}H_{22}N_6O$. 1.0$CH_3SO_3H$. 1.25$H_2O$: C, 55.23; H, 5.62; N, 16.91; S, 6.14; Found: C, 55.27; H, 5.53; N, 16.95; S, 6.00.

Preparation of 8-[(2-pyridin-4-yl-ethylamino)-methyl]-2,9-dihydro-1,2,7,9-tetraaza-phenalen-3-one, 43

Synthesized using 4-ethylamino-pyridine for General Procedure D. 10% overall yield for last two steps. An HCl salt of 43 was prepared. MS (ES−): 319; $^1$H NMR (400 MHz, $D_2O$): 3.28 (t, J=7.8 Hz, 2H), 3.53 (t, J=7.8 Hz, 2H), 4.09 (s, 2H), 7.02 (d, J=8.0 Hz, 1H), 7.35 (d, J=8.0 Hz, 1H), 7.52 (t, J=8.0 Hz, 1H), 7.70 (d, J=5.3 Hz, 2H), 8.52 (d, J=5.3 Hz, 2H). Anal. Calcd. for $C_{17}H_{16}N_6O$. 1.3 HCl. 2.6 $H_2O$. 0.1 $N_2H_4$: C, 47.52; H, 5.38; N, 20.27; Found: C, 47.12; H, 5.26; N, 20.67.

Preparation of 8-(3,4-dihydro-1H-isoquinolin-2-ylmethyl)-2,9-dihydro-1,2,7,9-tetraaza-phenalen-3-one, 44

Synthesized using 1,2,3,4-tetrahydro-isoquinoline for General Procedure D. 30% overall yield for last two steps. MS (ES−): 330; $^1$H NMR (400 MHz, DMSO-$d_6$): 2.81-2.90 (m, 4H); 3.52 (s, 2H), 3.72 (s, 2H), 7.05-7.25 (m, 4H), 7.51 (d, J=7.8 Hz, 1H), 7.63 (d, J=8.0 Hz, 1H), 7.74 (t, J=8.0 Hz, 1H), 11.30 (s, br, 1H), 11.91 (s, 1H). Anal. Calcd. for $C_{19}H_{17}N_5O$: C, 68.87; H, 5.17; N, 21.13; Found: C, 68.34; H, 5.19; N, 21.30.

A mesylate salt of 44 was prepared. MS (ES−): 330; $^1$H NMR (400 MHz, $D_2O$): 2.80 (s, 3H), 3.31 (t, 2H), 3.85 (m, 2H), 4.47 (s, 2H), 4.68 (s, 2H), 7.23 (d, J=7.8 Hz, 1H), 7.28-7.42 (m, 4H), 7.67 (d, J=8.0 Hz, 1H); 7.80 (t, J=7.9 Hz, 1H). Anal. Calcd. for $C_{19}H_{17}N_5O$. 1.12 $CH_3SO_3H$. 2.0 $H_2O$: C, 50.87; H, 5.41; N, 14.74; S, 7.56; Found: C, 50.89; H, 5.47; N, 14.84; S, 7.63.

Preparation of 8-(5,6-Dimethoxy-3,4-dihydro-1H-isoquinolin-2-ylmethyl)-2,9-dihydro-1,2,7,9-tetraaza-phenalen-3-one, 45

Synthesized using 5,6-dimethoxy-1,2,3,4-tetrahydro-isoquinoline for General Procedure D. 29% overall yield for last two steps. MS (ES−): 311; $^1$H NMR (400 MHz, DMSO-$d_6$): 2.79 (s, 4H), 3.49 (s, 2H), 3.61 (s, 2H), 3.67 (s, 3H), 3.70 (s, 3H), 6.69 (d, J=8.8 Hz, 1H), 7.48 (d, J=7.6 Hz, 1H), 7.63 (d, J=7.8 Hz, 1H), 7.74 (t, J=7.6 Hz, 1H), 11.55 (s, 1H). Anal. Calcd. for $C_{21}H_{21}N_5O_3$: C, 64.44; H, 5.41; N, 17.89; Found: C, 64.24; H, 5.43; N, 17.98.

A mesylate salt of 45 was prepared. MS (ES−): 330; $^1$H NMR (400 MHz, $D_2O$): 2.82 (s, 3H), 3.21 (t, 2H), 3.65-3.85 (m, 8H), 4.48 (s, 2H), 4.60 (s, 2H), 6.75 (s, 1H), 6.83 (s, 1H), 7.38 (d, 1H), 7.71 (d, 1H), 7.82 (t, 1H). Anal. Calcd. for $C_{21}H_{21}N_5O_3.1.18CH_3SO_3H$. 1.75 $H_2O$: C, 49.70; H, 5.49; N, 13.07; S, 7.03; Found: C, 49.77; H, 5.49; N, 13.17; S, 7.03.

Preparation of 8-[4-(3-Trifluoromethyl-benzenesulfonyl)-[1,4]diazepan-1-ylmethyl]-2,9-dihydro-1,2,7,9-tetraaza-phenalen-3-one, 46

Synthesized from compound 26. To a solution of 26 (0.2 g, 0.67 mmol) in 5 mL of $CH_2Cl_2$ was added TEA (2 mmol) and 3-trifluoromethyl-benzenesulfony chloride (1 mmol). The mixture was stirred at room temperature over night. After the solvents were evaporated, the residue was poured into 10 mL of $H_2O$ and the product was purified by preparative HPLC to afford analytically pure white solid (15% yield). MS (ES+): 507; $^1$H NMR (400 MHz, DMSO-$d_6$): 1.82 (m, 2H), 2.73-2.81 (m, 4H), 3.25-3.42 (m, 6H), 7.44 (d, J=7.8 Hz, 1H), 7.63 (d, J=7.2 Hz, 1H), 7.74 (t, J=7.8 Hz, 1H), 7.89 (t, J=8.2 Hz, 1H), 8.04-8.13 (m, 3H), 11.10 (s, br, 1H), 11.75 (s, 1H). Anal. Calcd. for $C_{22}H_{21}F_3N_6O_3S$. 1.1 $H_2O$: C, 50.21; H, 4.44; N, 15.97; S, 6.09; Found: C, 50.19; H, 4.54; N, 15.50; S, 5.97.

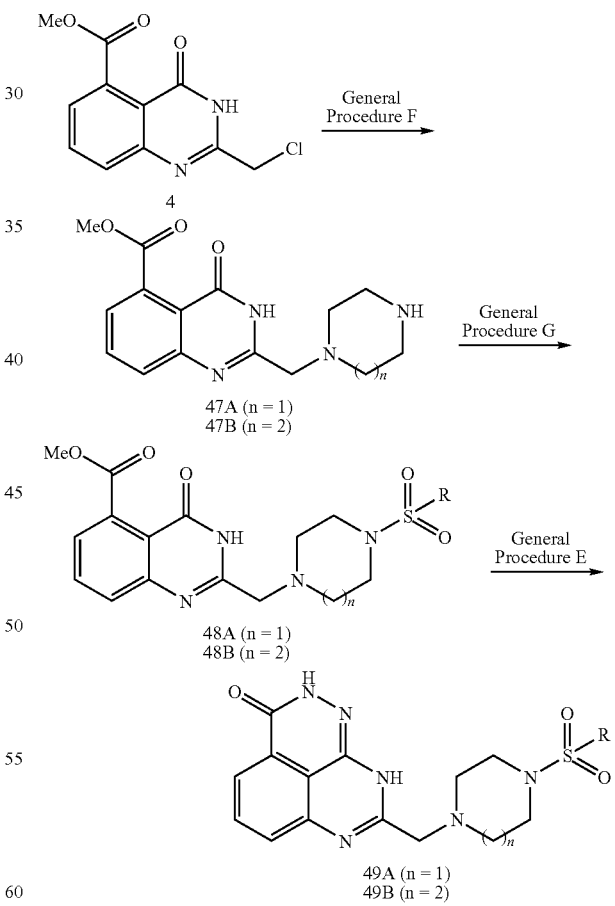

Scheme 2

General Procedure F: Preparation of Compounds 47A and 47B:

Displacement of the chloro group of compound 4 with piperazine or [1,4]diazepane using General procedure F provides the compound 47A or 47B. To a stirring solution of 4 (1 eq) in acetonitrile was added piperazine or [1,4]diazepane (large excess) under a blanket of nitrogen. The solution was allowed to stir overnight and then evaporated to dryness. The crude material was purified via silica plug with 9:1 dichloromethane:methanol to afford a white solid, 4-Oxo-2-piperazin-1-ylmethyl-3,4-dihydro-quinazoline-5-carboxylic acid methyl ester, 47A or 2-[1,4]diazepan-1-ylmethyl-4-oxo-3,4-dihydro-quinazoline-5-carboxylic acid methyl ester, 47B.

General Procedure G: Preparation of Compounds 48A and 48B:

A reaction of amine 47A or 47B with various sulfonyl chloride yields sulfonyl amide 48A or 48B. To a stirring solution of 47A or 47B (1.0 eq) in pyridine was added various sulfonyl chloride (1.1 eq). The reaction was allowed to stir overnight and then was evaporated to dryness. The residue was then extracted with dichloromethane and washed with brine. The product was evaporated to dryness and used without further purification.

General Procedure E: Preparation of compounds 49A and 49B:

A 2,9-dihydro-1,2,7,9-tetraaza-phenalen-3-one ring can be formed by condensation of the compound 48A or 48B with hydrazine. To a solution of the compounds 6 in absolute ethanol is added excess anhydrous hydrazine at room temperature. The solution is refluxed for overnight and cooled to room temperature. Ice-cold water is added and white solid is separated. The solid is collected by vacuum filtration and washed with water and small amount of methanol to give white solid products 6 in 40-90% of yield. An example was given in the preparation of compounds 49A and 49B.

Example 2

Preparation of 8-[4-(4-methoxy-benzenesulfonyl)-piperazin-1-ylmethyl]-2,9-dihydro-1,2,7,9-tetraaza-phenalen-3-one, 50

To a stirring solution of 4 (2.2 g, 8.73 mmol, 1 eq) in 200 mL of acetonitrile was added piperazine (14 g, 0.162 mol, large excess) under a blanket of nitrogen. The solution was allowed to stir overnight and then evaporated to dryness. The crude material was purified via silica plug with 9:1 dichloromethane:methanol to afford 2.0 g of a fluffy white solid, 4-Oxo-2-piperazin-1-ylmethyl-3,4-dihydro-quinazoline-5-carboxylic acid methyl ester, 47A. MS (ES−): 301; $^1$H NMR (400 MHz, DMSO-$d_6$): 2.40-2.43 (m, 4H), 2.69-2.72 (m, 4H), 3.41 (s, 2H), 3.83 (s, 3H), 7.44 (d, J=7.2 Hz, 1H), 7.74 (d, J=8.2 Hz, 1H), 7.82 (t, J=7.8 Hz, 1H).

To a stirring solution of 47A (170 mg, 0.56 mmol, 1 eq) in 5 mL of pyridine was added 4-methoxybenzene sulfonyl chloride (130 mg, 0.62 mmol, 1.1 eq) resulting in a bright yellow solution. The reaction was allowed to stir overnight and then was evaporated to dryness. The waxy residue was then extracted with dichloromethane and washed with brine. The crude material was dissolved in 10 mL of EtOH and 5 mL of hydrazine monohydrate (large excess). This solution was refluxed overnight resulting in a heavy white precipitate which was filtered, washed with ethyl ether and dried to give an off white solid. This solid was then purified via chromatography to afford 112 mg of analytically pure compound 50. A mesylate salt of 50 was prepared. 8% overall yield for last three steps. MS (ES+): 455; $^1$H NMR (400 MHz, DMSO-$d_6$): 2.34 (s, 3H), 3.19 (bs, 4H), 3.44 (bs, 4H), 3.89 (s, 3H), 4.20 (s, 2H), 7.25 (d, J=9.0 Hz, 2H), 7.72 (d, J=7.8 Hz, 1H), 7.70-7.83 (m, 4H), 11.20 (s, br, 1H), 11.93 (s, 1H). Anal. Calcd. for $C_{21}H_{22}N_6O_4S$. 1.5 $CH_3SO_3H$. 3.0 $H_2O$. 1.0 $N_2H_4$: C, 41.20; H, 5.29; N, 13.24; S, 12.22; Found: C, 41.07; H, 5.09; N, 13.53; S, 12.62.

The following compounds were synthesized from the similar procedures of preparation of compound 50, using the appropriate corresponding sulfonyl chloride.

Preparation of 8-[4-(3-fluoro-benzenesulfonyl)-piperazin-1-ylmethyl]-2,9-dihydro-1,2,7,9-tetraaza-phenalen-3-one, 51

Synthesized using 3-fluoro-benzenesulfonyl chloride and compound 47A for General Procedure G. A mesylate salt of 51 was prepared. 35% overall yield for last three steps. MS (ES−): 441; $^1$H NMR (400 MHz, DMSO-$d_6$): 2.31 (s, 3H), 3.25 (bs, 4H), 3.39 (bs, 4H), 4.15 (s, 2H), 7.42 (d, J=7.8 Hz, 1H), 7.65-7.71 (m, 4H), 7.78-7.82 (m, 2H), 11.78 (s, 1H). Anal. Calcd. for $C_{20}H_{19}N_6O_3S$. 1.25 $CH_3SO_3H$. 2.4 $H_2O$: C, 42.43; H, 4.87; N, 13.87; S, 11.91; Found: C, 42.13; H, 4.79; N, 13.48; S, 11.89.

Preparation of 8-[4-(toluene-4-sulfonyl)-piperazin-1-ylmethyl]-2,9-dihydro-1,2,7,9-tetraaza-phenalen-3-one, 52

Synthesized using toluene-4-sulfonyl chloride and compound 47A for General Procedure G. A mesylate salt of 52 was prepared. 38% overall yield for last three steps. MS (ES−): 438; $^1$H NMR (400 MHz, DMSO-$d_6$): 2.36 (s, 3H), 2.45 (s, 3H), 3.20 (bs, 4H), 3.46 (bs, 4H), 4.22 (s, 2H), 7.43 (d, J=7.8 Hz, 1H), 7.54 (d, J=7.8 Hz, 2H), 7.68-7.81 (m, 4H), 11.90 (s, 1H). Anal. Calcd. for $C_{21}H_{22}N_6O_3S$. 1.3 $CH_3SO_3H$. 4.0 $H_2O$: C, 42.25; H, 5.58; N, 13.22; S, 11.61; Found: C, 42.63; H, 5.53; N, 13.40; S, 11.90.

Preparation of 8-(4-benzenesulfonyl-piperazin-1-ylmethyl)-2,9-dihydro-1,2,7,9-tetraaza-phenalen-3-one, 53

Synthesized using benzensulfonyl chloride and compound 47A for General Procedure G. A mesylate salt of 53 was prepared. 30% overall yield for last three steps. MS (ES−): 438; $^1$H NMR (400 MHz, DMSO-$d_6$): 2.70 (s, 3H), 3.36 (bs, 4H), 3.51 (bs, 4H), 4.14 (s, 2H), 7.11 (d, J=8.0 Hz, 1H), 7.40-7.70 (m, 7H), 11.90 (s, 1H). Anal. Calcd. for $C_{20}H_{20}N_6O_3S$. 1.2 $CH_3SO_3H$. 2.5$H_2O$. 0.08 $N_2H_4$: C, 43.36; H, 5.17; N, 14.67; S, 12.01; Found: C, 43.00; H, 5.17; N, 15.05; S, 12.40.

Preparation of 8-[4-(3-trifluoromethyl-benzenesulfonyl)-piperazin-1-ylmethyl]-2,9-dihydro-1,2,7,9-tetraaza-phenalen-3-one, 54

Synthesized using 3-trifluoro-benzensulfonyl chloride and compound 47A for General Procedure G. A mesylate salt of 54 was prepared. 15% overall yield for last three steps. MS (ES−): 438; $^1$H NMR (400 MHz, DMSO-$d_6$): 2.32 (s, 3H), 3.26-3.35 (m 8H), 4.10 (s, 2H), 7.43 (d, J=8.0 Hz, 1H), 7.69-7.80 (m, 2H), 7.98-8.26 (m, 4H), 11.92 (s, 1H)

Anal. Calcd. for $C_{21}H_{19}F_3N_6O_3S$. 1.3 $CH_3SO_3H$. 2.0$H_2O$: C, 40.99; H, 4.35; N, 12.86; S, 11.29; Found: C, 40.71; H, 4.60; N, 12.68; S, 11.50.

Preparation of 8-[4-(4-chloro-benzenesulfonyl)-piperazin-1-ylmethyl]-2,9-dihydro-1,2,7,9-tetraaza-phenalen-3-one, 55

Synthesized using 4-chlorobenzensulfonyl chloride and compound 47A for General Procedure G. A mesylate salt of 55 was prepared. 15% overall yield for last three steps. MS (ES−): 458; $^1$H NMR (400 MHz, DMSO-d$_6$): 2.31 (s, 3H), 3.18 (bs, 4H), 3.40 (bs, 4H), 3.98 (s, 2H), 7.43 (d, J=7.7 Hz, 1H), 7.68-7.84 (m, 5H), 11.90 (s, 1H).
Anal. Calcd. for $C_{20}H_{19}ClN_6O_3S \cdot 1.3 CH_3SO_3H \cdot 2.0 H_2O$: C, 41.27; H, 4.59; N, 13.56; S, 11.90; Found: C, 41.07; H, 4.66; N, 13.30; S, 11.89.

Preparation of 8-[4-(4-fluoro-benzenesulfonyl)-piperazin-1-ylmethyl]-2,9-dihydro-1,2,7,9-tetraaza-phenalen-3-one, 56

Synthesized using 4-fluorobenzensulfonyl chloride and compound 47A for General Procedure G. An HCl salt of 56 was prepared. 42% overall yield for last three steps. MS (ES−): 441; $^1$H NMR (400 MHz, DMSO-d$_6$): 2.31 (s, 3H), 3.18 (bs, 4H), 3.40 (bs, 4H), 3.98 (s, 2H), 7.43 (d, J=7.8 Hz, 1H), 7.68-7.84 (m, 5H), 11.90 (s, 1H).

Preparation of 8-[4-(4-isopropyl-benzenesulfonyl)-piperazin-1-ylmethyl]-2,9-dihydro-1,2,7,9-tetraaza-phenalen-3-one, 57

Synthesized using 4-isopropylbenzensulfonyl chloride and compound 47A for General Procedure G. A mesylate salt of 57 was prepared. 22% overall yield for last three steps. MS (ES−): 465; $^1$H NMR (400 MHz, DMSO-d$_6$): 1.26 (d, J=6.8 Hz, 6H), 2.33 (s, 3H), 3.01-3.05 (m, 1H), 3.16-3.32 (m, 10H), 7.41 (d, J=8.1 Hz, 1H), 7.59 (d, J=8.6 Hz, 2H), 7.68-7.80 (m, 4H), 11.89 (s, 1H). Anal. Calcd. for $C_{23}H_{26}N_6O_3S \cdot 1.35 CH_3SO_3H \cdot 1.75 H_2O \cdot 0.1 N_2H_4$: C, 46.35; H, 5.64; N, 13.76; S, 11.94; Found: C, 46.01; H, 5.62; N, 13.80; S, 12.33.

Preparation of 8-[4-(4-tert-butyl-benzenesulfonyl)-piperazin-1-ylmethyl]-2,9-dihydro-1,2,7,9-tetraaza-phenalen-3-one, 58

Synthesized using 4-tertbutylbenzensulfonyl chloride and compound 47A for General Procedure G. A mesylate salt of 58 was prepared. 23% overall yield for last three steps. MS (ES−): 480; $^1$H NMR (400 MHz, DMSO-d$_6$): 1.25 (s, 9H), 2.21 (s, 3H), 3.05-3.15 (m, 8H), 3.99 (bs, 2H), 7.32 (d, J=8.1 Hz, 1H), 7.59-7.72 (m, 6H), 11.81 (s, 1H). Anal. Calcd. for $C_{24}H_{28}N_6O_3S \cdot 1.5 CH_3SO_3H \cdot 2.75 H_2O$: C, 45.42; H, 5.90; N, 12.46; S, 11.89; Found: C, 45.23; H, 5.76; N, 12.84; S, 12.17.

Preparation of 8-[4-(4-isopropyl-benzenesulfonyl)-[1,4]diazepan-1-ylmethyl]-2,9-dihydro-1,2,7,9-tetraaza-phenalen-3-one, 59

Synthesized using 4-isopropylbenzensulfonyl chloride and compound 47B for General Procedure G. 22% overall yield for last two steps. MS (ES−): 479; $^1$H NMR (400 MHz, DMSO-d$_6$): 1.23 (d, 6H), 1.79 (m, 2H), 2.40-2.55 (m, 4H), 2.71-2.90 (n 4H), 3.00 (m, 1H), 3.48 (s, 2H), 7.48 (m, 3H), 7.73 (m, 4H), 11.80 (s, 1H). Anal. Calcd. for $C_{24}H_{28}N_6O_3S$: C, 59.98; H, 5.87; N, 17.49; S, 6.67; Found: C, 60.02; H, 5.85; N, 17.55; S, 6.52.

Preparation of 8-[4-(4-chloro-benzenesulfonyl)-[1,4]diazepan-1-ylmethyl]-2,9-dihydro-1,2,7,9-tetraaza-phenalen-3-one, 60

Synthesized using 4-chloro-benzenesulfony chloride and compound 47B for General Procedure G. 8% overall yield for last three steps. MS (ES−): 472; $^1$H NMR (400 MHz, DMSO-d$_6$): 1.80 (m, 2H), 2.73-2.78 (m, 4H), 3.50 (m, 4H), 3.69 (s, 2H), 7.45 (d, J=8.2 Hz, 1H), 7.71-7.83 (m, 6H), 10.95 (s, br, 1H), 11.76 (s, 1H). A mesylate salt of 60 was prepared. $^1$H NMR (400 MHz, D$_2$O): 1.92 (m, 2H), 2.73 (s, 5H), 3.50-3.77 (m, 8H), 4.36 (s, 2H), 7.49 (d, J=7.2 Hz, 1H), 7.75 (t, J=8.1 Hz, 2H), 7.78-7.93 (m 4H). Anal. Calcd. for $C_{21}H_{21}ClN_6O_3S \cdot 1.61 CH_3SO_3H$: C, 39.57; H, 4.99; N, 12.25; S, 12.20; Found: C, 39.50; H, 5.29; N, 12.57; S, 12.47.

Preparation of 8-[4-(3-fluoro-benzenesulfonyl)-[1,4]diazepan-1-ylmethyl]-2,9-dihydro-1,2,7,9-tetraaza-phenalen-3-one, 61

Synthesized using 3-fluoro-benzenesulfony chloride and compound 47B for General Procedure G. 16% overall yield for last two steps. MS (ES+): 457; $^1$H NMR (400 MHz, DMSO-d$_6$): 1.79 (m, 2H), 2.70-2.81 (m, 4H), 3.26-3.40 (m, 4H), 3.48 (s, 2H), 7.45 (d, J=7.3 Hz, 1H); 7.55-7.74 (m, 6H), 11.10 (s, br, 1H), 11.75 (s, 1H). Anal. Calcd. for $C_{21}H_{21}FN_6O_3S \cdot 1.15 H_2O$: C, 52.85; H, 4.92; N, 17.61; S, 6.72; Found: C, 52.88; H, 4.93; N, 17.43; S, 6.48.

Preparation of 8-[4-(4-methoxy-benzenesulfonyl)-1-[1,4]diazepan-1-ylmethyl]-2,9-dihydro-1,2,7,9-tetraaza-phenalen-3-one, 62

Synthesized using 4-methoxy-benzenesulfonyl chloride and compound 47B for General Procedure G. 21% overall yield for last two steps. MS (ES+): 469; $^1$H NMR (400 MHz, DMSO-d$_6$): 1.78 (m, 2H), 2.72-2.79 (m, 4H), 3.30-3.39 (m, 4H), 3.48 (s, 2H), 3.84 (s, 3H), 7.14 (d, J=8.2 Hz, 2H), 7.48 (d, J=8.1 Hz, 1H), 7.63 (d, J=7.2 Hz, 1H); 7.09-7.22 (m, 3H), 11.10 (s, br, 1H), 11.80 (s, 1H). Anal. Calcd. for $C_{22}H_{24}N_6O_4S \cdot 1.0 H_2O$: C, 54.31; H, 5.39; N, 17.27; S, 6.59; Found: C, 54.38; H, 5.34; N, 17.28; S, 6.19.

Preparation of 8-[4-(4-tert-butyl-benzenesulfonyl)-[1,4]diazepan-1-ylmethyl]-2,9-dihydro-1,2,7,9-tetraaza-phenalen-3-one, 63

Synthesized using 4-t-butyl-benzenesulfony chloride and compound 47B for General Procedure G. 14% overall yield for last two steps. MS (ES−): 493; $^1$H NMR (400 MHz, DMSO-d$_6$): 1.31 (s, 9H), 1.79 (m, 2H), 2.73-2.86 (m, 4H), 3.26-3.41 (m, 4H), 3.48 (s, 2H), 7.45 (d, J=8.6 Hz, 1H), 7.62-7.76 (m, 6H), 11.20 (s, br, 1H), 11.80 (s, 1H). Anal. Calcd. for $C_{25}H_{30}N_6O_3S$: C, 60.71; H, 6.11; N, 16.99; S, 6.48; Found: C, 60.78; H, 6.10; N, 17.08; S, 6.36.

Preparation of 8-[4-(4-amino-benzenesulfonyl)-[1,4]diazepan-1-ylmethyl]-2,9-dihydro-1,2,7,9-tetraaza-phenalen-3-one, 64

Synthesized using 4-nitro-benzenesulfony chloride and compound 47B for General Procedure G. 14% overall yield for last two steps. MS (ES−): 452; $^1$H NMR (400 MHz, DMSO-d$_6$): 1.76 (m, 2H), 2.71-2.79 (m, 4H), 3.21-3.31 (m, 4H), 3.46 (s, 2H), 6.01 (s, 2H), 6.64 (d, J=8.6 Hz, 2H), 7.39 (d, J=8.6 Hz, 2H), 7.48 (d, J=8.0 Hz, 1H), 7.63 (d, J=7.9 Hz, 1H), 7.74 (t, J=7.8 Hz, 1H), 11.10 (s, br, 1H), 11.75 (s, 1H). Anal.

Calcd. for $C_{21}H_{23}N_7O_3S$. 0.5 $H_2O$: C, 54.53; H, 5.23; N, 21.20; S, 6.93; Found: C, 54.50; H, 5.24; N, 20.84; S, 6.74.

Preparation of 8-[4-(biphenyl-4-sulfonyl)-[1,4]diazepan-1-ylmethyl]-2,9-dihydro-1,2,7,9-tetraaza-phenalen-3-one, 65

Synthesized using biphenyl-4-sulfony chloride and compound 47B for General Procedure G. 10% overall yield for last two steps. MS (ES–): 513; $^1$H NMR (400 MHz, DMSO-$d_6$): 1.82 (m, 2H), 2.73-2.83 (m, 4H), 3.29-3.41 (m, 4H), 3.48 (s, 2H), 7.47-7.53 (m, 4H), 7.62 (d, J=8.1 Hz, 1H), 7.68-7.78 (m, 3H), 7.82-7.93 (m, 4H), 11.00 (s, br, 1H), 11.75 (s, 1H). Anal. Calcd. for $C_{27}H_{26}N_6O_3S$. 2.3$H_2O$: C, 58.32; H, 5.55; N, 15.11; S, 5.77; Found: C, 58.24; H, 4.89; N, 15.10; S, 5.79.

Preparation of 8-[4-(4-amino-benzenesulfonyl)-piperazin-1-ylmethyl]-2,9-dihydro-1,2,7,9-tetraaza-phenalen-3-one, 66

Synthesized using 4-nitrobenzene sulfonyl chloride and compound 47A for General Procedure G. A mesylate salt of 66 was prepared. 35% overall yield for last three steps. MS (ES–): 438; $^1$H NMR (400 MHz, DMSO-$d_6$): 2.32 (s, 3H), 3.13 (bs, 4H), 3.42 (bs, 4H), 4.18 (s, 2H), 6.71 (d, J=8.8 Hz, 2H), 7.40-7.43 (m, 3H), 7.70-7.80 (m, 2H), 11.20 (s, br, 1H), 11.92 (s, 1H). Anal. Calcd. for $C_{20}H_{21}N_7O_3S$. 1.3 $CH_3SO_3H$. 2.75 $H_2O$: C, 41.67; H, 5.20; N, 15.97; S, 12.01; Found: C, 41.76; H, 5.25; N, 15.92; S, 12.22.

Scheme 3

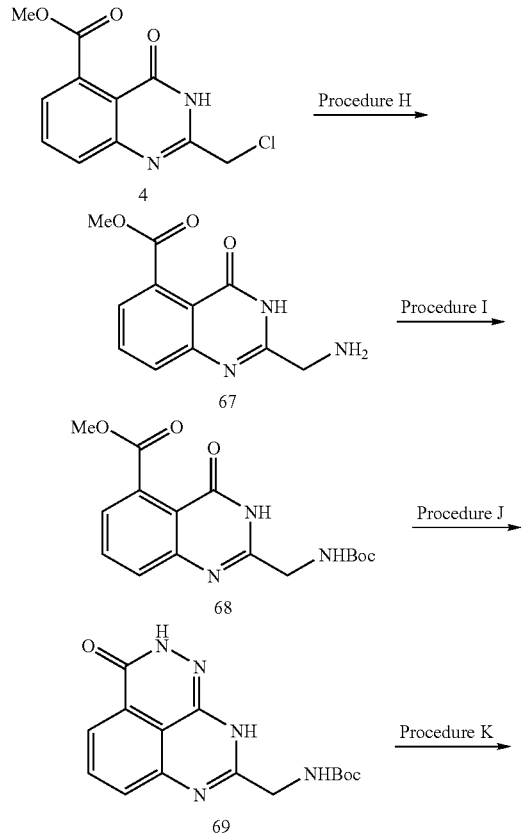

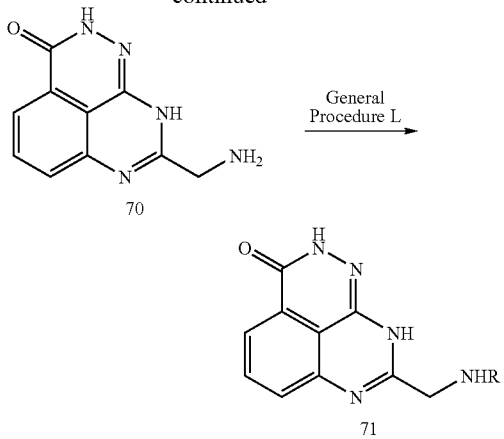

General Procedure L to prepare compounds 71. To a stirring solution of 70 (1.0 eq) in THF under nitrogen was added TEA (1 mL, excess) and either sulfonyl chloride or acid chloride (1.2 eq). The reaction was allowed to stir for four hours after which time it was evaporated and extracted with $CH_2Cl_2$/$H_2O$, dried and condensed. Crude material was further purified via column chromatography using 9:1 $CH_2Cl_2$/MeOH to afford analytically pure products 71.

Example 3

Preparation of (3-oxo-2,9-dihydro-3H-1,2,7,9-tetraaza-phenalen-8-ylmethyl)-carbamic Acid tert-butyl Ester, 69

Procedure H to prepare 2-aminomethyl-4-oxo-3,4-dihydro-quinazoline-5-carboxylic acid methyl ester, 67. To a solution of 25 mL of 7N $NH_3$ (large excess) in MeOH at 0° C. was added compound 4 (1.0 g, 4.0 mmol) in a sealed tube. The mixture was then heated to 60° C. for 4 hours. The mixture was evaporated to dryness, dissolved and re-evaporated in 2×50 mL of $CH_2Cl_2$. Product was used as is without further purification.

Procedure I to prepare 2-(tert-butoxycarbonylamino-methyl)-4-oxo-3,4-dihydro-quinazoline-5-carboxylic acid methyl ester, 68. To a solution of 50 mL $CH_2Cl_2$ of with 2 mL of TEA (excess), catalytic DMAP and compound 67 (from Procedure H) was added boc anhydride (2.6 g, 3 eq) at room temperature. Reaction was allowed to stir for 60 minutes, during which time all solids went into solution. The solution was evaporated to dryness and purified via column chromatography using $CH_2Cl_2$ and 5% MeOH to afford 0.5 g of analytically pure compound, 68.

Procedure J to prepare 69. 5 g of compound 68 was dissolved in 10 mL of hydrazine monohydrate and 25 mL of ethanol. The mixture was refluxed for four hours until no starting material was detected by TLC. Reaction was cooled, poured over 100 mL of cold water and extracted with 2×25 mL of EtOAc. Organic layers were dried with brine and then magnesium sulfate. Purified via column chromatography using 9:1 $CH_2Cl_2$/MeOH to afford 2.7 g of analytically pure compound 69. MS (ES–): 314; $^1$H NMR (400 MHz, $CDCl_3$): 1.45 (s, 9H), 3.90 (s, 2H), 6.15 (bs, 1H), 6.94-7.30 (m, 3H), 12.38-12.43 (m, br, 2H). Anal. Calcd. for $C_{15}H_{17}N_5O_3$.0.2 $H_2O$: C, 56.49; H, 5.50; N, 21.96; Found: C, 56.61; H, 5.60; N, 21.85.

Preparation of 8-aminomethyl-2,9-dihydro-1,2,7,9-tetraaza-phenalen-3-one, 70

Procedure K to prepare 70. 250 mg of compound 69 was dissolved in 10 mL of $CH_2Cl_2$ along with 4 mL of TFA. The reaction was allowed to stir at room temperature overnight resulting in a heavy white precipitate, which was filtered off and washed with $CH_2Cl_2$ and dried under vacuum to afford a quantitative yield of analytically pure material, a TFA salt of compound 70. MS (ES+): 216; $^1$H NMR (400 MHz, $D_2O$): 3.97 (s, 2H), 6.91 (d, J=8.2 Hz, 1H), 7.23 (d, J=7.8 Hz, 1H), 7.43 (t, J=8.0 Hz, 1H). Anal. Calcd. for $C_{10}H_9N_5O$. 1.3 $CF_3COOH$. 0.2 $H_2O$: C, 41.27; H, 2.86; N, 19.10; Found: C, 41.00; H, 3.04; N, 19.25.

Preparation of 4-methyl-N-(3-oxo-2,9-dihydro-3H-1,2,7,9-tetraaza-phenalen-8-ylmethyl)-benzenesulfonamide, 72

Synthesized using 4-methylbenzene sulfonyl chloride and compound 70 for General Procedure L. 20% yield for compound 72. MS (ES−): 368; $^1$H NMR (400 MHz, $CDCl_3$): 2.27 (s, 3H), 3.93 (s, 2H), 7.28-7.43 (m, 3H), 7.67-7.78 (m, 4H), 11.43 (s, 1H), 11.83 (s, 1H). Anal. Calcd. for $C_{17}H_{15}N_5O_3S$: C, 55.27; H, 4.09; N, 18.96; S, 8.68; Found: C, 54.93; H, 4.09; N, 18.63; S, 8.33.

Preparation of N-(3-oxo-2,9-dihydro-3H-1,2,7,9-tetraaza-phenalen-8-ylmethyl)-benzenesulfonamide, 74

Synthesized using benzene sulfonyl chloride and compound 70 for General Procedure L. 25% yield for compound 74. MS (ES−): 354; $^1$H NMR (400 MHz, $CDCl_3$): 3.95 (d, J=5.0 Hz, 2H), 7.44 (d, J=7.8 Hz, 1H), 7.45-7.60 (m, 3H), 7.67-7.77 (m, 2H), 7.91-7.93 (m, 2H), 8.24 (t, J=8.8 Hz, 1H), 11.24 (s, 1H), 11.83 (s, 1H). Anal. Calcd. for $C_{16}H_{13}N_5O_3S$. 1.0 $H_2O$: C, 51.47; H, 4.05; N, 18.76; S, 8.59; Found: C, 51.17; H, 4.20; N, 18.73; S, 8.31.

Preparation of N-(3-oxo-2,9-dihydro-3H-1,2,7,9-tetraaza-phenalen-8-ylmethyl)-acetamide, 75

Synthesized using acetic anhydride and compound 70 for General Procedure L. 22% yield for compound 75. MS (ES−): 256; $^1$H NMR (400 MHz, DMSO-$d_6$): 1.91 (s, 3H), 4.05 (s, 2H), 7.32 (d, J=8.1 Hz, 1H), 7.49-7.81 (m, 2H), 8.40 (t, J=8.3 Hz, 1H). 11.25 (s, 1H), 11.75 (s, 1H). Anal. Calcd. for $C_{12}H_{11}N_5O_2$.0.5 $H_2O$: C, 54.13; H, 4.54; N, 26.30; Found: C, 54.14; H, 4.52; N, 26.00.

Preparation of 4-nitro-N-(3-oxo-2,9-dihydro-3H-1,2,7,9-tetraaza-phenalen-8-ylmethyl)-benzamide, 76

Synthesized using 4-nitro-benzoyl chloride and compound 70 for General Procedure L. 25% yield for compound 76. MS (ES−): 363; $^1$H NMR (400 MHz, $CDCl_3$): 3.99 (s, 2H), 7.18-7.20 (m, 1H), 7.34-7.38 (m, 1H), 7.75-7.90 (m, 2H), 8.20-8.32 (m, 2H), 8.40-8.48 (m, 3H).

In vitro PARP Inhibitory Potency—$IC_{50}$

A convenient method to determine $IC_{50}$ of a PARP inhibitor compound is a PARP assay using purified recombinant human PARP from Trevigan (Gaithersburg, Md.), as follows: The PARP enzyme assay is set up on ice in a volume of 100 microliters consisting of 100 mM Tris-HCl (pH 8.0), 1 mM $MgCl_2$, 28 mM KCl, 28 mM NaCl, 3.0 µg/ml of DNase I-activated herring sperm DNA (Sigma, Mo.), 30 micromolar [$^3$H]nicotinamide adenine dinucleotide (62.5 mci/mmole), 15 micrograms/ml PARP enzyme, and various concentrations of the compounds to be tested. The reaction is initiated by adding enzyme and incubating the mixture at 25° C. After 2 minutes of incubation, the reaction is terminated by adding 500 microliters of ice cold 30% (w/v) trichloroacetic acid. The precipitate formed is transferred onto a glass fiber filter (Packard Unifilter-GF/C) and washed three times with 70% ethanol. After the filter is dried, the radioactivity is determined by scintillation counting. The compounds of this invention were found to have potent enzymatic activity in the range of a few nanomolar to 20 micromolar in $IC_{50}$ in this inhibition assay.

Using the PARP assay described above, approximate IC50 values were obtained for the following compounds:

TABLE I

| Compound | Structure | IC50 nM |
|---|---|---|
| 7 | 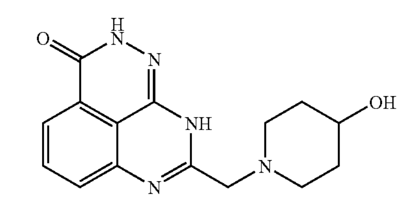 | 35 |
| 8 | 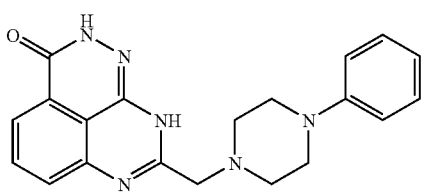 | 23 |

TABLE I-continued

| Compound | Structure | IC50 nM |
|---|---|---|
| 9 | 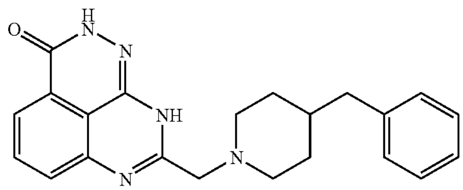 | 35 |
| 10 | 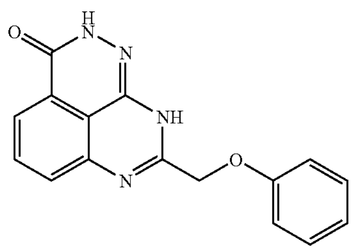 | 19 |
| 11 | 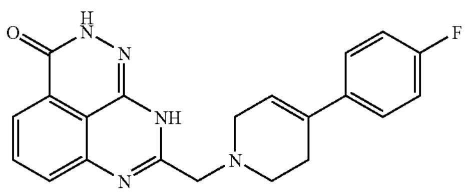 | 6 |
| 12 | 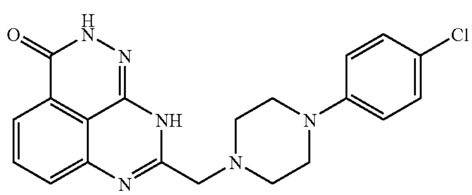 | 9 |
| 13 | 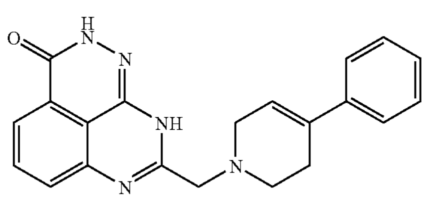 | 12 |
| 14 | 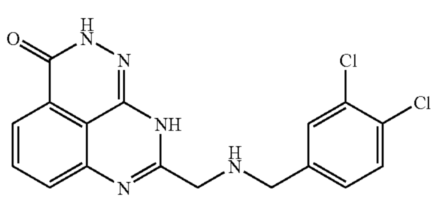 | 18 |
| 15 | 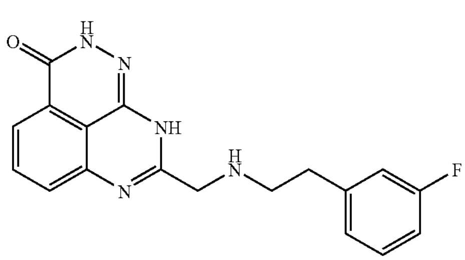 | 32 |

TABLE I-continued

| Compound | Structure | IC50 nM |
|---|---|---|
| 16 | 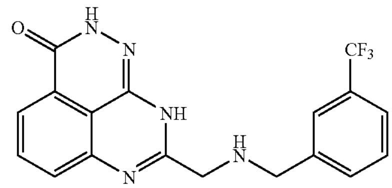 | 21 |
| 17 | 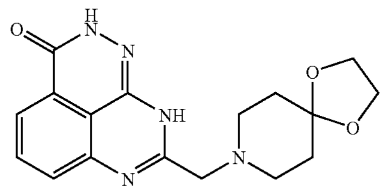 | 20 |
| 18 | 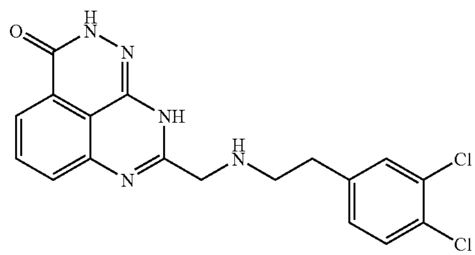 | 17 |
| 19 | 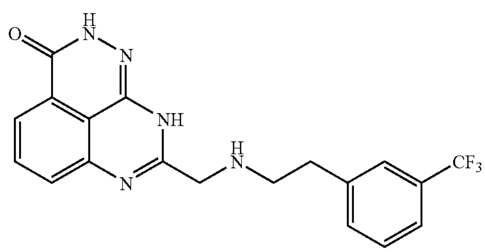 | 18 |
| 20 | 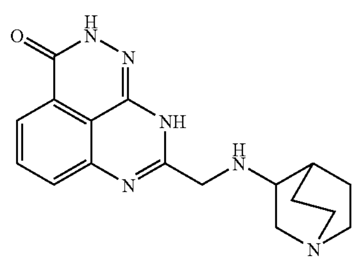 | 35 |
| 21 | 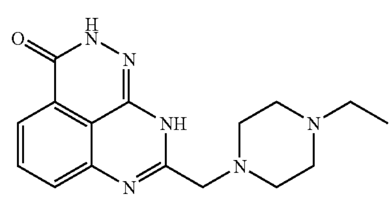 | n/a |
| 22 | 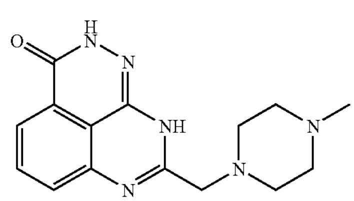 | 35 |

TABLE I-continued

| Compound | Structure | IC50 nM |
|---|---|---|
| 23 | 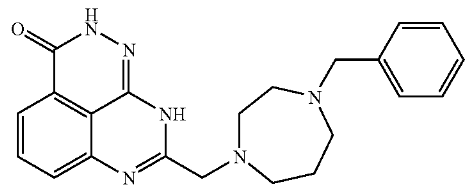 | 39 |
| 24 | 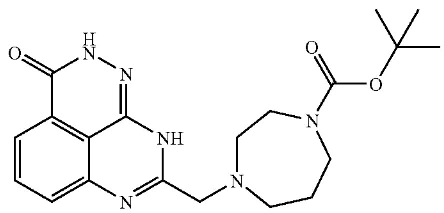 | 51 |
| 25 | 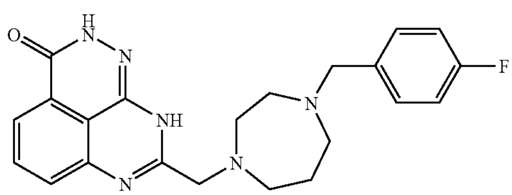 | 26 |
| 26 | 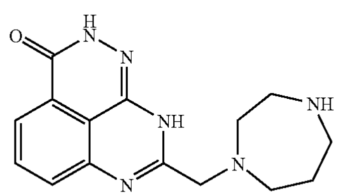 | 41 |
| 27 | 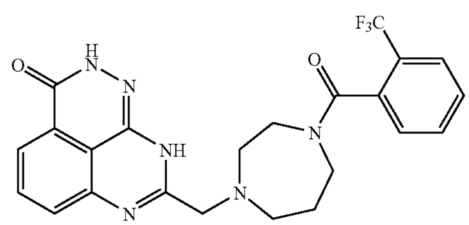 | 43 |
| 28 | 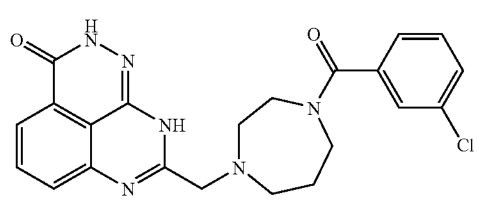 | 29 |
| 30 | 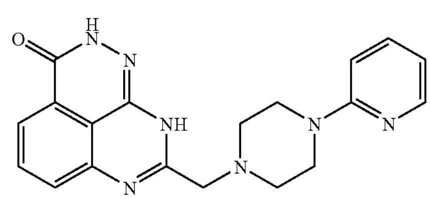 | 13 |

TABLE I-continued

| Compound | Structure | IC50 nM |
|---|---|---|
| 31 | 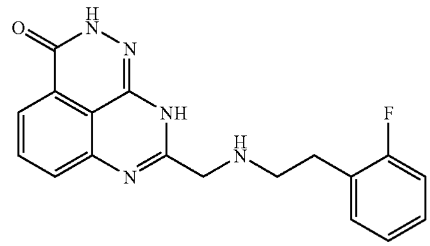 | 28 |
| 32 | 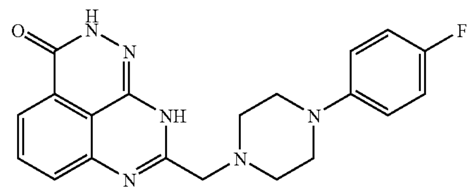 | 31 |
| 33 | 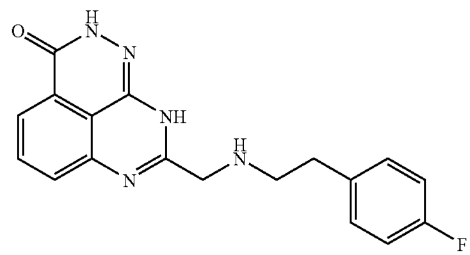 | n/a |
| 34 | 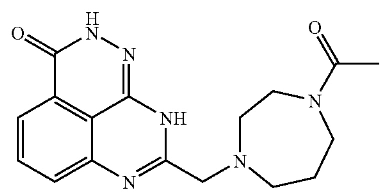 | 49 |
| 35 | 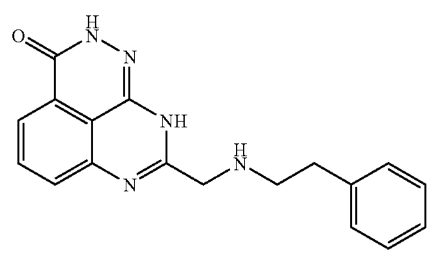 | 44 |
| 36 | 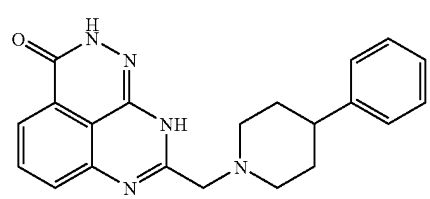 | 19 |
| 37 | 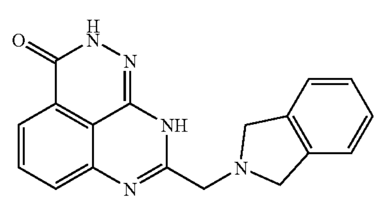 | 12 |

TABLE I-continued

| Compound | Structure | IC50 nM |
|---|---|---|
| 38 | 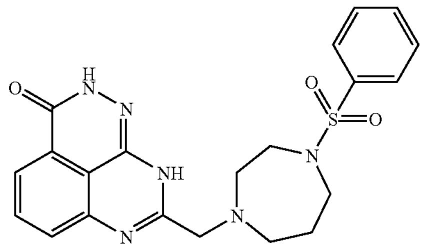 | 20 |
| 39 | 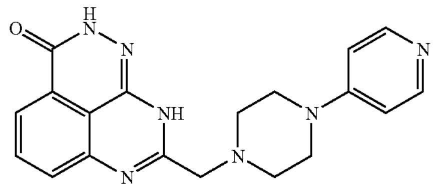 | 15 |
| 40 | 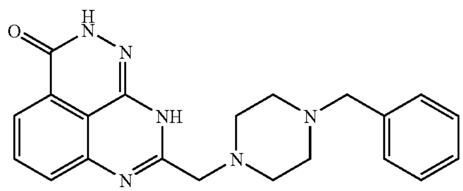 | 39 |
| 41 | 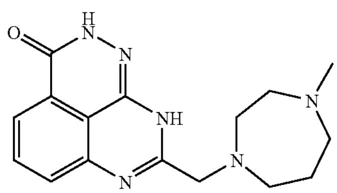 | 42 |
| 42 | 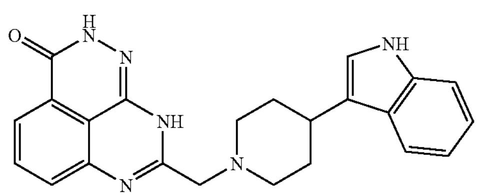 | 13 |
| 43 | 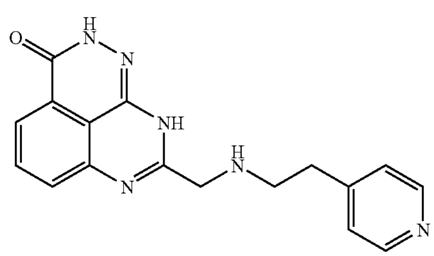 | 38 |
| 44 | 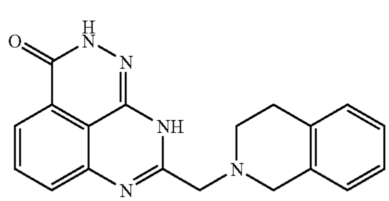 | 21 |

TABLE I-continued

| Compound | Structure | IC50 nM |
|---|---|---|
| 45 | 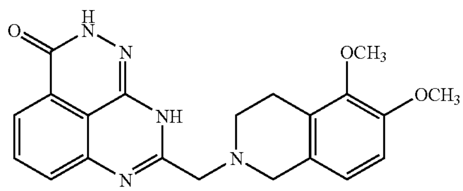 | 49 |
| 46 | 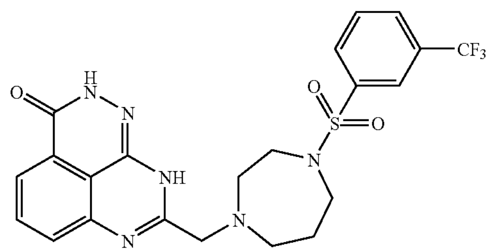 | 11 |
| 50 | 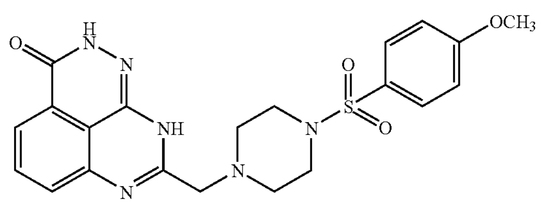 | 52 |
| 51 | 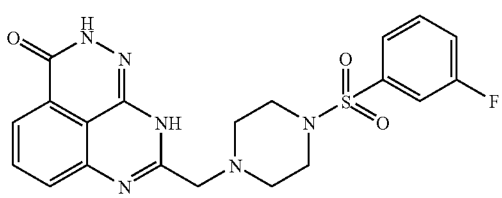 | 15 |
| 52 | 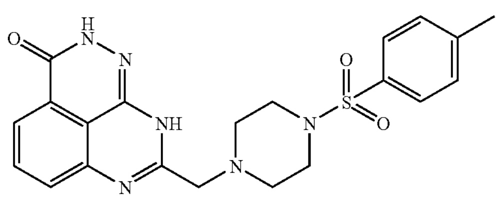 | 21 |
| 53 | 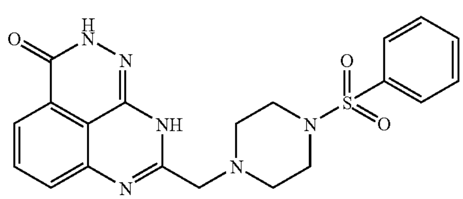 | 23 |
| 54 | 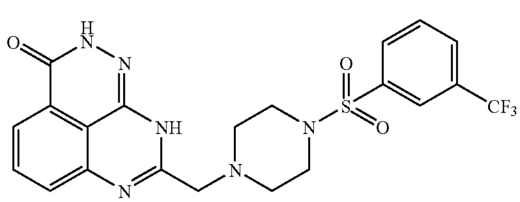 | 14 |

TABLE I-continued

| Compound | Structure | IC50 nM |
|---|---|---|
| 55 | 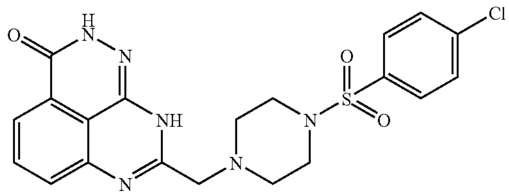 | 18 |
| 56 | 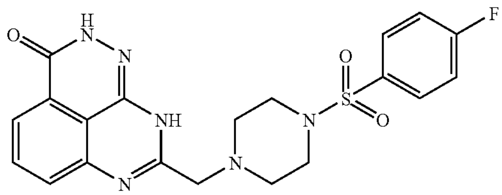 | 27 |
| 57 | 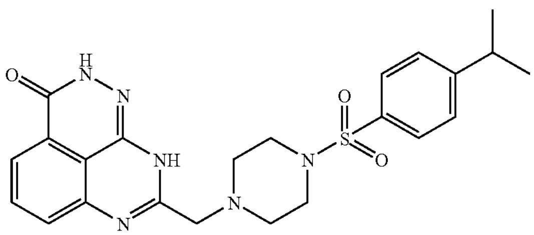 | 17 |
| 58 | 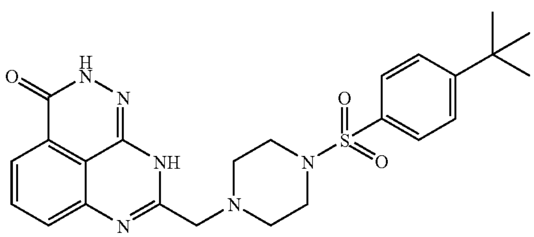 | 13 |
| 59 | 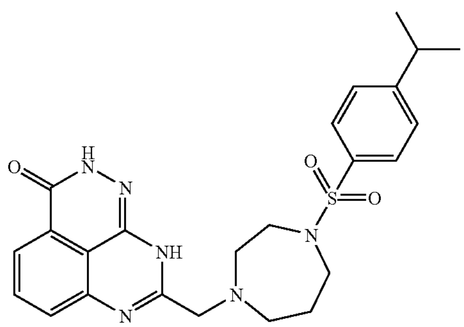 | 23 |
| 60 | 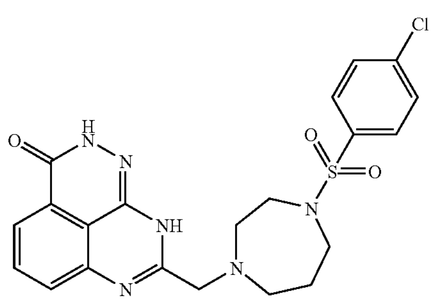 | 24 |

TABLE I-continued

| Compound | Structure | IC50 nM |
|---|---|---|
| 61 | 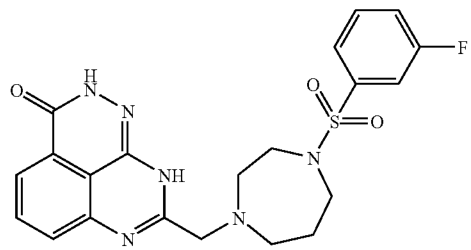 | 27 |
| 62 | 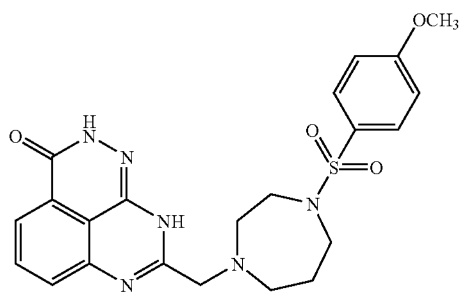 | 22 |
| 63 | 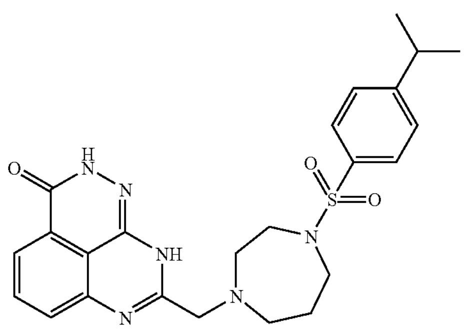 | 19 |
| 64 | 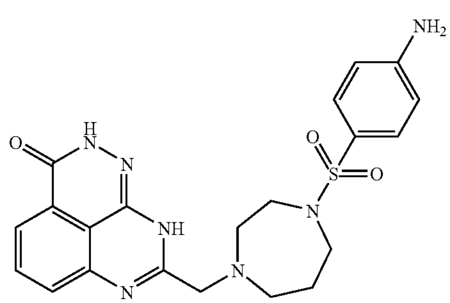 | 15 |
| 65 | 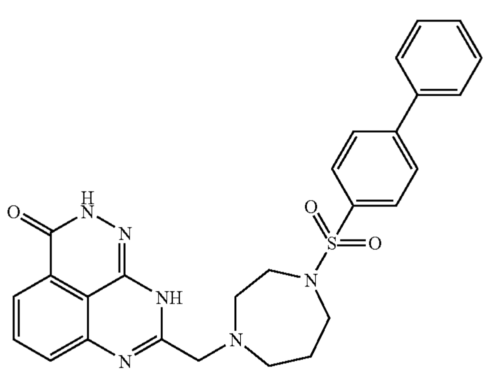 | 22 |

TABLE I-continued

| Compound | Structure | IC50 nM |
|---|---|---|
| 66 | 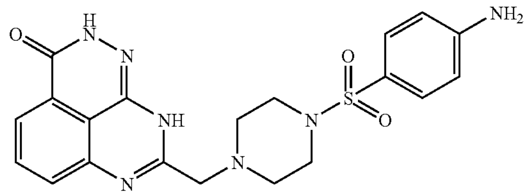 | 45 |
| 69 | 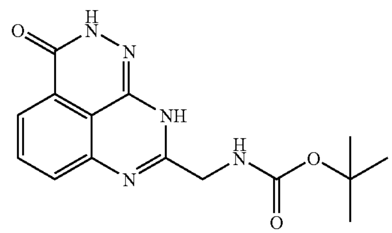 | 47 |
| 72 | 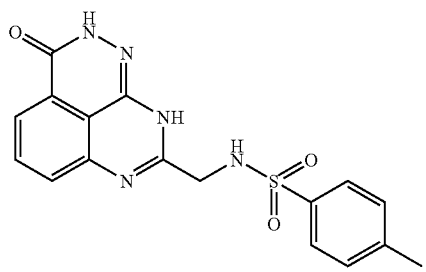 | 171 |
| 74 | 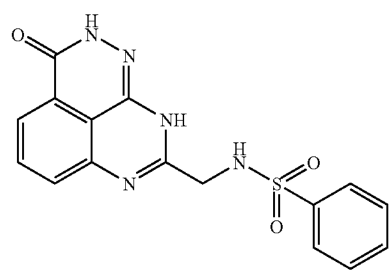 | 23 |
| 75 | 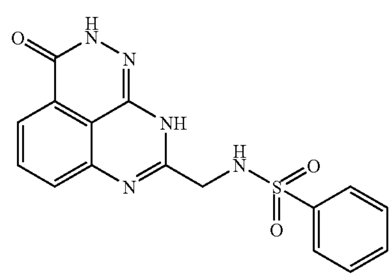 | 30 |
| 76 | 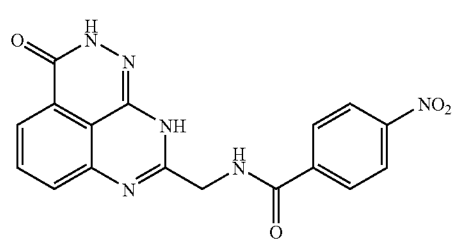 | 10 |

Efficacy In Vivo for Compound 13
1) Mouse Intracranial Model of B16 Melanoma:

The murine melanoma cell line B16 of C57BL/6J ($H-2^b/H-2^b$) origin was cultured in RPMI-1640 containing 10% fetal calf serum (Invitrogen, Milan, Italy), 2 mM L-glutamine, 100 units/ml penicillin and 100 μg/ml streptomycin (Flow Laboratories, Mc Lean, Va.), at 37° C. in a 5% $CO_2$ humidified atmosphere. TMZ was provided by Schering-Plough Research Institute (Kenilworth, N.J.). Compound 13 was dissolved in 70 mM PBS without potassium.

For intracranial transplantation, cells ($10^4$ in 0.03 ml of RPMI-1640) were injected intracranially (ic) through the center-middle area of the frontal bone to a 2 mm depth, using a 0.1 ml glass microsyringe and a 27-gauge disposable needle. Murine melanoma B16 cells ($10^4$) were injected ic into male B6D2F1 (C57BL/6×DBA/2) mice. Before tumor challenge, animals were anesthetized with ketamine (100 mg/kg) and xylazine (5 mg/kg) in 0.9% NaCl solution (10 ml/kg/ip). Histological evaluation of tumor growth in the brain was performed 1-5 days after tumor challenge, in order to determine the timing of treatment.

The compound 13 was administered per os 15 min before TMZ. Control mice were always injected with drug vehicles. In tumor-bearing mice treatment started 48 h after challenge, when tumor infiltration in the surrounding brain tissue was histologically evident. Mice were treated with compound 13 by oral gavage once a day for five days, at the doses of 10 mg/kg.

In tumor-bearing mice, treatment started on day 2 after challenge, when tumor infiltration in the surrounding brain tissue was histologically evident. Mice were treated daily with compound 13 plus TMZ for 5 days and monitored for mortality for 90 days. Median survival times (MST) were determined and the percentage of increase in lifespan (ILS) was calculated as: $\{[MST (days) of treated mice/MST (days) of control mice]-1\} \times 100$. Efficacy of treatments was evaluated by comparing survival curves between treated and control groups.

All procedures involving mice and care were performed in compliance with national and international guidelines (European Economy Community Council Directive 86/109, OLJ318, Dec. 1, 1987 and NIH Guide for care and use of laboratory animals, 1985).

Survival curves were generated by Kaplan-Meier product-limit estimate and statistical differences between the various groups (8 animals/group) were evaluated by log-rank analysis with Yates correction (software Primer of Biostatistics, McGraw-Hill, New York, N.Y.). Statistical significance was determined at a p=0.05 level. Differences were considered statistically significant when P<0.05.

The results indicate oral administration of 10 mg/kg compound 13 significantly increased the survival time of mice treated with compound 13+TMZ combination and was significantly higher than that observed in animals receiving TMZ as single agent (P<0.0001). No significant differences in survival times were observed between control and TMZ treated groups (FIG. 1).

2) Intracranial Xenograft Model of SJGBM2 Glioma in Mice:

The compound 13 was tested in the intracranial xenograft model of SJGBM2 glioma in mice (Tentori, et al. Clin. Cancer Reser. 2003, 9, 5370). For this purpose compound 13 was given once at 15 min pre-TMZ at 10 mg/kg, po.

Figure 2:
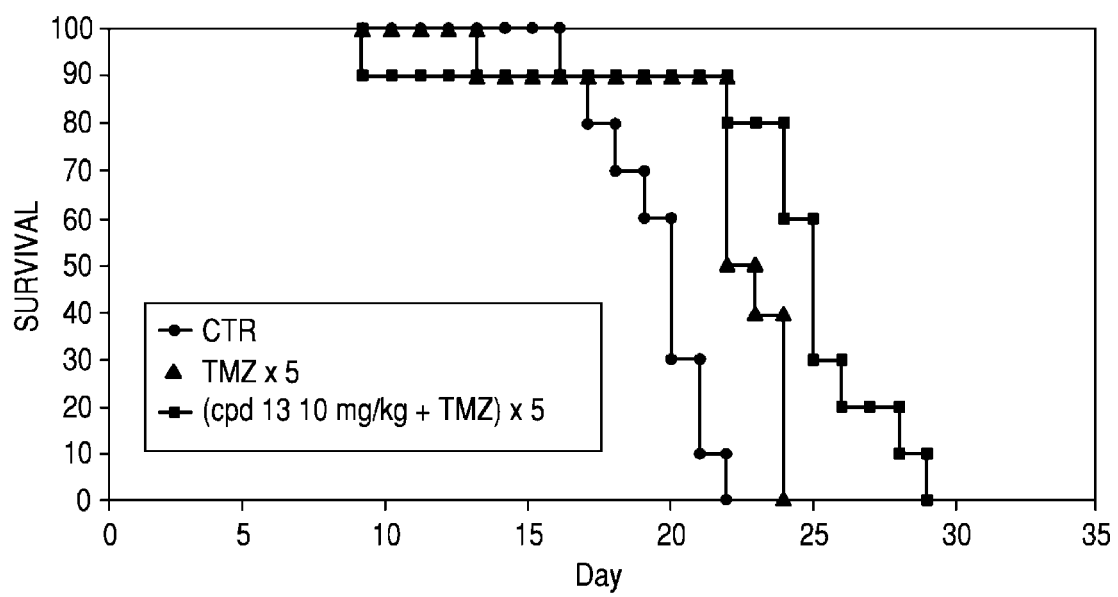
FIG. 2.—The oral administration of PARP-1 inhibitor Compound 13+TMZ demonstrating the enhanced survival in the intracranial SJGBM glioma model.

A dose of 10 mg/kg compound 13 was found to be efficacious (FIG. 2). Its combination with TMZ increased MTS from 22.5 d (TMZ alone) to 25 d (P=0.002).

Figure 3:
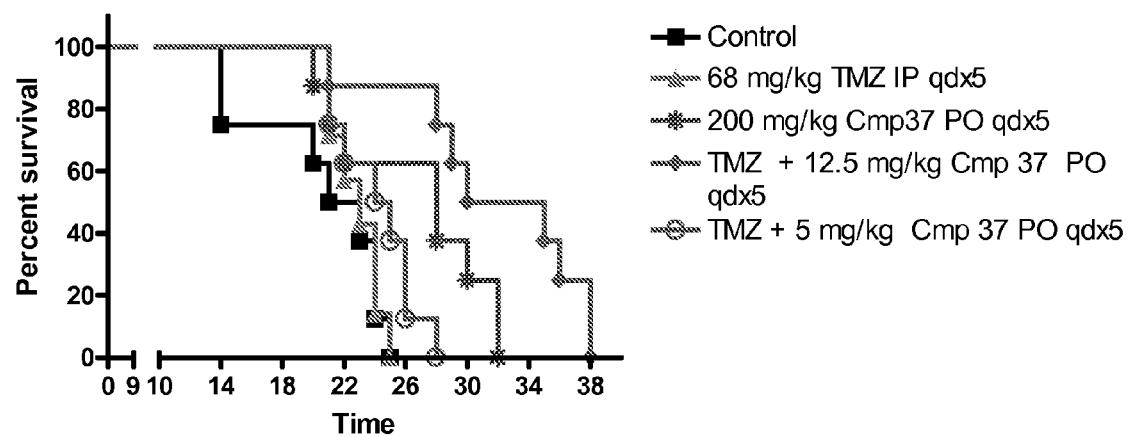
FIG. 3.—The oral administration of PARP-1 inhibitor Compound 37+TMZ demonstrating the enhance survival of mice bearing the B16 melanoma model.

Efficacy In Vivo for Compound 37
1) Mouse Intracranial Model of B16 Melanoma:

The experiment was performed as described above for Compound 13. It was investigated whether oral administration of Compound 37 (5 mg/kg or 12.5 mg/kg), might increase the efficacy of TMZ against B16 melanoma growing at the CNS site. In mice bearing B16 melanoma, the results indicated that the mean survival time of the groups treated with Compound 37 12.5 mg/kg+TMZ combination was significantly higher than that observed in animals receiving TMZ as single agent (FIG. 3).

Figure 4:
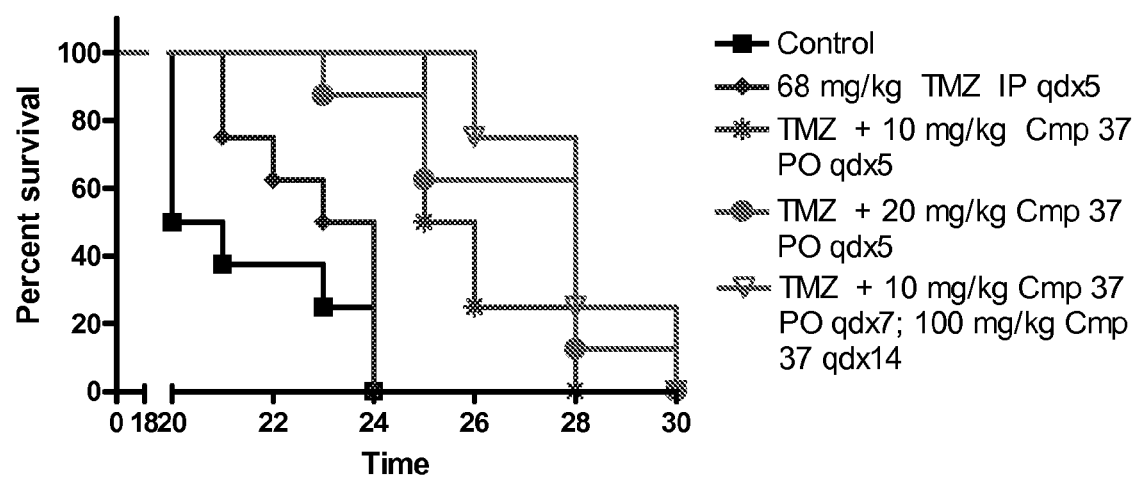
FIG. 4.—The oral administration of PARP-1 inhibitor Compound 37+TMZ demonstrating the enhanced survival in the intracranial SJGBM glioma model.

2) Intracranial Xenograft Model of SJGBM2 Glioma in Mice:

The efficacy of Compound 37 was then investigated using an orthotopic model of a human glioblastoma multiforme xenograft (SJGBM2) in nude mice. The response of SJGBM2 to TMZ, used as single agent or in combination with Compound 37 (10 mg/kg or 20 mg/kg) for five days or in combination with Compound 37 (MGI25036) 10 mg/kg for five days followed by a 14-day treatment with Compound 37 100 mg/kg as single agent, is shown in FIG. 4. The results indicate that oral administration of Compound 37 (10 mg/kg or 20 mg/kg)+TMZ significantly prolonged survival of tumor bearing mice with respect to controls or to animals treated with TMZ. It should be noted that in this tumor model TMZ was ineffective. Treatment with 10 mg/kg Compound 37+TMZ for five days followed by a high dose of Compound 37 (100 mg/kg) for 14 days significantly increased animal survival with respect to 10 mg/kg Compound 37+TMZ for five days.

3) Enhancement of Radiation Treatment of Head and Neck Squamous Cell Carcinoma

Figure 5:
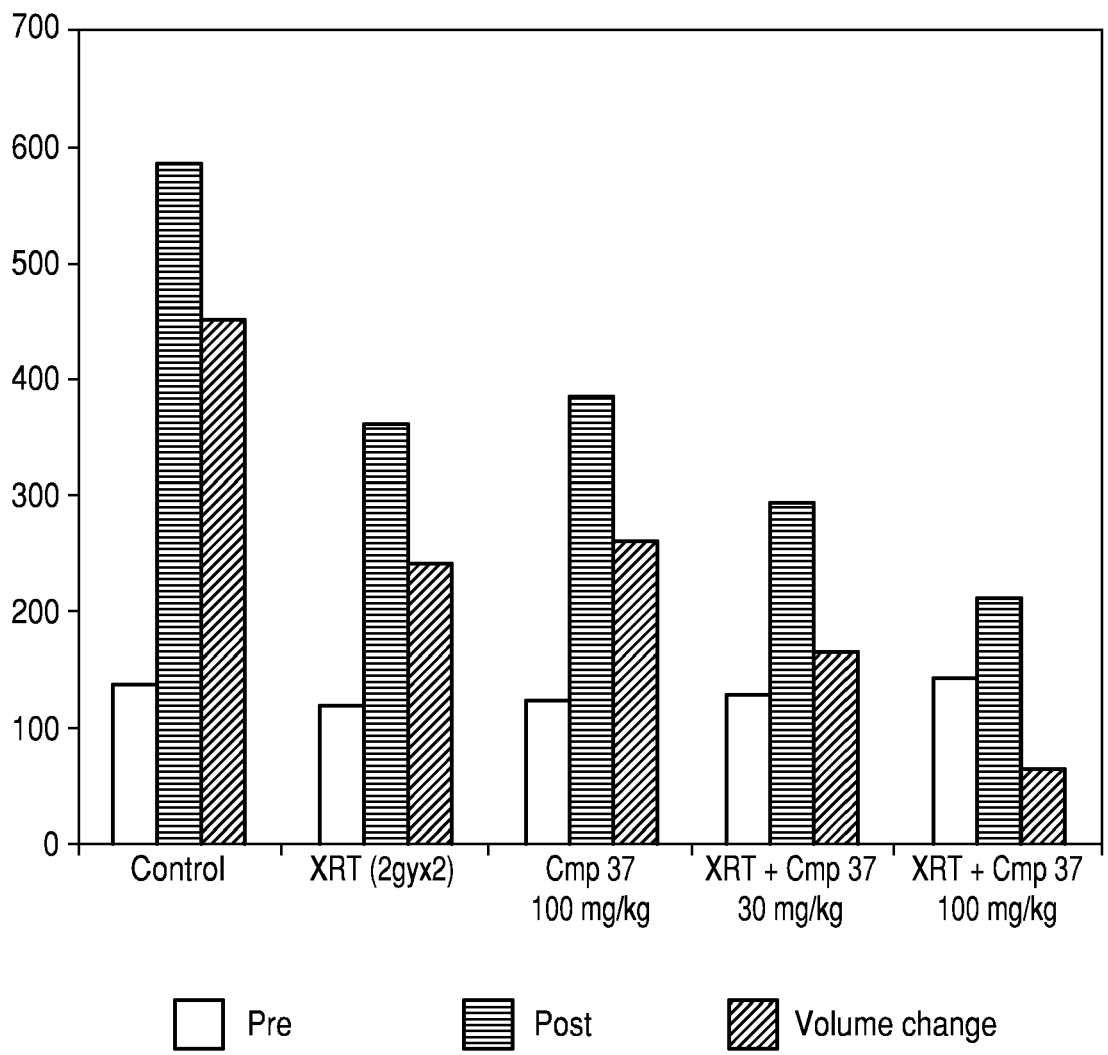
FIG. 5.—The oral administration of PARP-1 inhibitor Compound 37+radiation demonstrating inhibition of tumor growth in the model of head and neck cancer.
Figure 6:
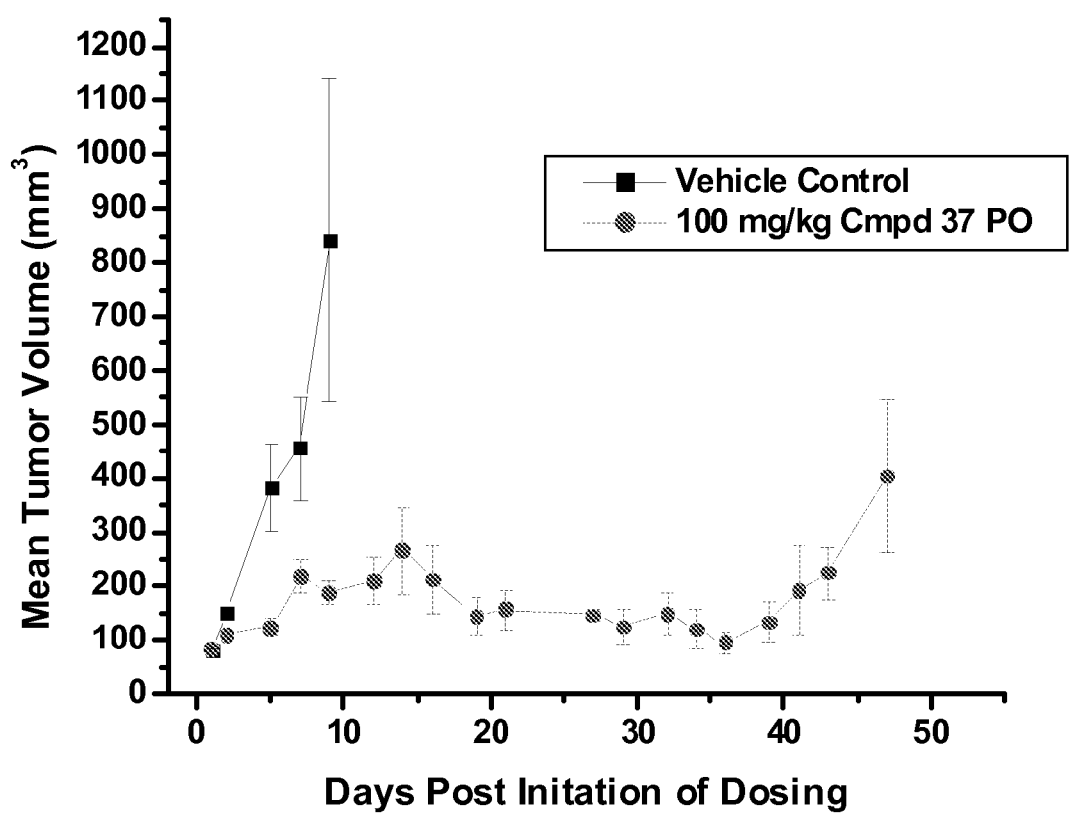
FIG. 6.—The oral administration of PARP-1 inhibitor Compound 37 demonstrating inhibition of growth of BRCA1 mutant tumors

Human HNSCC cell line JHU012 was used, having been previously genetically characterized and originally derived at the Johns Hopkins University Head and Neck Laboratories from human tumor explants. The cell line was maintained in RPMI 1640 medium with 10% fetal bovine serum and 1% penicillin/streptomycin at 5% $CO_2$ in 37° C. humidified incubators. Experiments were performed on 6-week-old male BALB/c nude mice nu/nu. The animals were randomly divided into the following treatment groups: Group 1—controls, Group 2—Radiation alone (2 Gray (gy)/day for 2 days), Group 3—100 mg/kg Compound 37 alone orally (PO) qdx17, Group 4—30 mg/kg Compound 37 PO+Radiation, Group 5—100 mg/kg Compound 37 PO+Radiation, with each group consisting of 8 mice. Mice were anesthetized by intraperitoneal injection of 3-5 mL tribromoethanol. Tumors were established at the right flank by subcutaneous injection of $1\times10^7$ cells. Fourteen days post cell injection tumors were surgically exposed and measured in 3 dimensions using calipers. Compound 37 was then dosed orally in treatment Groups 3-5. In Groups 4 and 5, animals received Compound 37 15 minutes prior to radiation (2 gy/day for 2 days). At day 31 post tumor cell inoculation, tumors were again surgically exposed and measured in 3 dimensions using calipers A significant inhibition of tumor growth was observed in Group 5 treated with 100 mg/kg orally administered Compound 37+Radiation (tumor volume at end of experiment=209.04 $mm^3$) compared to the control Group 1 (tumor volume at end of experiment=585.9 $mm^3$ p<0.01). (FIG. 5) Compound 37 at 30 mg/kg in combination with radiation had no significant effect on tumor growth inhibition compared to radiation alone (FIG. 5). In addition, 100 mg/kg Compound 37 PO qdx17 alone had no significant effect on tumor growth inhibition compared to vehicle controls (FIG. 5). This indicates an enhanced effect when the higher dose of Compound 37 was combined with radiation as opposed to either treatment modality alone.

4) Effect of Compound 37 on Tumor Growth in Mice Bearing BRCA-1 Deficient Tumors $1 \times 10^6$ BRCA-1 null cells were injected subcutaneously on the right flank of female nu/nu mice (6-7 weeks old; Harlan Sprague Dawley, Indianapolis Ind.). After approximately 10-14 days, the tumors were approximately 100 mm$^3$. Mice were sorted into groups so that mean tumor size was similar among groups with minimum standard deviations. Dosing started the day after sorting and tumor volume was monitored three times per week. Tumors were measured in two diameters and volume calculated by $(l \times w)^2/2$. Mice were removed from the study when tumors reached 1500 mm$^3$. "Time to Endpoint" or TTE (the number of days it takes for the tumor to reach 1500 mm$^3$ or greater) is the endpoint of the study. Compound 37 was weighed out every 2-3 days and solubilized in sterile bottled water (J. T. Baker, Ultrapure Bioreagent 4221-02) to 10 mg/ml. The compound was dosed orally, daily for 28 days from start of the study day 1. A positive control was utilized, using a well known PARP inhibitor shown to be effective as a stand alone agent in the BRCA models (Bryant et al). The positive control agent was dosed at 25 mg/kg IP qdx5 from start of experiment. 100 mg/kg Compound 37 was effective in significantly retarding tumor growth in the BRCA-1 null model both times tested. When the dosing of Compound 37 was stopped at day 28, the tumors start to grow approximately 10-14 days later. Compound 37 not only significantly delayed tumor growth compared to vehicle controls but also delayed tumor growth compared to the positive control ($p<0.05$) in both experiments.

A study was conducted to compare the bioavailablity and brain plasma levels of various mammals administered with the disclosed compounds and a similar prior art compound. The prior art compound has the following formula:

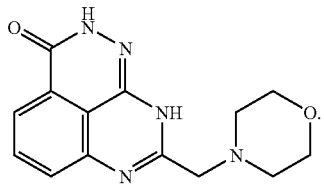

The comparative study was conducted as follows:

PARP inhibitors in water solutions were dosed either by bolus (<1 min) intravenous injection, or by oral gavage. For dogs, intravenous and oral dosing was performed in a crossover design with a one-week washout period between dose routes. The screening dose was 30 mg/kg for each compound. For mice, three animals per time point were sacrificed by $CO_2$ asphyxia and blood collected by cardiac puncture. For rats and dogs, serial blood samples were taken at various time points from the indicated number of animals. For rats, the volume of blood sampled was immediately replaced with 2× volume of 1:1 donor rat blood:heparinized saline. The blood samples were transferred to heparinized containers, briefly mixed, and stored on ice until centrifugation to prepare plasma. The plasma was transferred to fresh containers and stored at $\leq -70°$ C. until bioanalysis. In some cases brains or tumor tissue were collected after sacrifice and stored at $\leq -70°$ C. until bioanalysis.

Plasma samples were processed by precipitation with acetonitrile, evaporation and reconstitution. Brain and tumor tissue samples were homogenized with phosphate buffered saline, pH 7.4, precipitated with acetonitrile, followed by evaporation and reconstitution. The reconstituted samples were analyzed vs. matrix calibration standards by LC-MS/MS. The bioanalytical method performance was verified by the performance of quality control samples. Generally, the plasma lower limit of quantitation was 5 ng/mL. Tissue lower limits of quantitation depended on the degree of dilution during homogenization, but usually were 15 to 20 ng/g.

Plasma, brain, and tumor concentration data were processed by noncompartmental pharmacokinetic analysis using WinNonlin Professional Version 4.1. AUC was calculated using the Linear/Log rule. Time points for the Lambda Z phase were selected by visual inspection. The slopes of terminal phases were calculated by unweighted linear regression.

Selective PARP inhibitors were tested for basic plasma and tissue pharmacokinetic properties in mice, rats, and dogs. After assessment, this family compounds appear to be orally bioavailable in all species and to penetrate brain and tumor tissue. Table 1 summarizes the oral bioavailability (PO) for compounds 8, 13, 36 and 37 and the comparative compound in mice and rats and brain/plasma ratio (B/P) for these five compounds in mice and rats.

The results of the comparative study are summarized in Table II. The results show that while the prior art compound has good bioavailability the prior art compound has a ratio of brain to plasma levels that is very low. Unexpectedly, the disclosed compounds of Formula (I) have a good ratio of brain to plasma level compared to the prior art compound. These results show the disclosed compounds are unexpectedly available to the central nervous system where needed for therapeutic benefit as compared to the prior art compound.

Table II. Comparison of Bioavailabity (PO) and Ratio of Brain to Plasma levels (B/P) for selected compounds of Formula (I) relative to a related prior art compound.

| Compound | PO in mice | B/P in mice | PO in rats | B/P in rats |
|---|---|---|---|---|
| 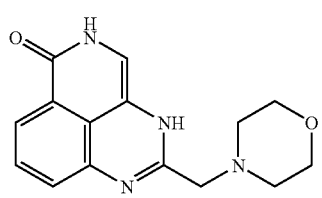 Comparative Compound | 77% | <5% | 77% | <5% |

-continued

| Compound | PO in mice | B/P in mice | PO in rats | B/P in rats |
|---|---|---|---|---|
| 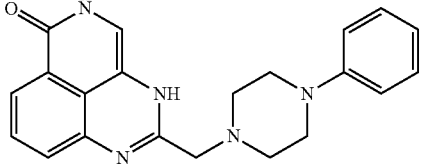 8 | 49% | 49% | 58% | 40% |
| 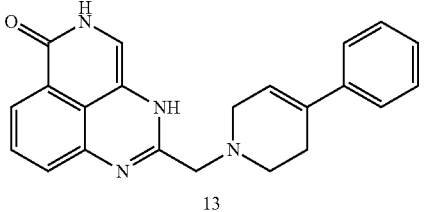 13 | 61% | 46% | 51% | 42% |
| 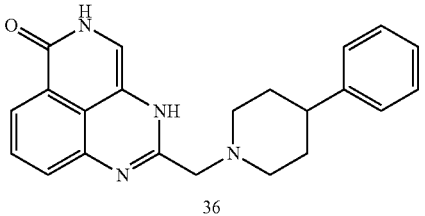 36 | 75% | 30-64% | 50% | 71-117% |
| 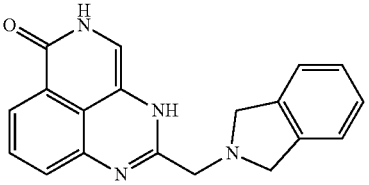 37 | 81% | 26% | 45% | 36% |

The invention being thus described, it will be obvious that the same may be varied in many ways. Such variations are not to be regarded as a departure from the spirit and scope of the invention, and all such modifications are intended to be included within the scope of the following claims.

INCORPORATION BY REFERENCE

All publications, patents, and pre-grant patent application publications cited in this specification are herein incorporated by reference, and for any and all purposes, as if each individual publication or patent application were specifically and individually indicated to be incorporated by reference. In the case of inconsistencies the present invention will prevail.

The invention claimed is:

1. The compound 37

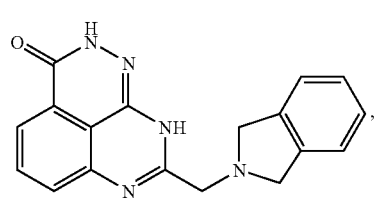

or a pharmaceutically acceptable salt or ester thereof.

2. A compound of claim 1, wherein the compound is a pharmaceutically acceptable salt or ester of compound 37.

3. A compound of claim 1, wherein the compound is a pharmaceutically acceptable salt of compound 37.

4. A compound of claim 3, wherein the pharmaceutically acceptable salt is the salt of an organic acid.

5. The compound

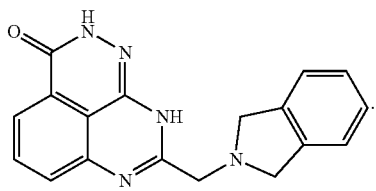

37

6. A pharmaceutical composition comprising the compound of claim 1, and a pharmaceutically acceptable carrier.

7. A pharmaceutical composition comprising the compound of claim 2, and a pharmaceutically acceptable carrier.

8. A pharmaceutical composition comprising the compound of claim 3, and a pharmaceutically acceptable carrier.

9. A pharmaceutical composition comprising the compound of claim 4, and a pharmaceutically acceptable carrier.

10. A pharmaceutical composition comprising the compound of claim 5, and a pharmaceutically acceptable carrier.

11. The pharmaceutical composition of claim 6, further comprising a chemotherapeutic agent selected from the group consisting of temozolomide, adriamycin, camptothecin, carboplatin, cisplatin, daunorubicin, docetaxel, doxorubicin, interferon-alpha, interferon-beta, interferon-gamma, interleukin 2, irinotecan, paclitaxel, topotecan, a taxoid, dactinomycin, danorubicin, 4'-deoxydoxorubicin, bleomycin, pilcamycin, mitomycin, neomycin, gentamycin, etoposide, 4-OH cyclophosphamide, a platinum coordination complex, and mixtures thereof.

12. The pharmaceutical composition of claim 11, wherein said chemotherapeutic agent is temozolomide, or a salt thereof.

* * * * *